United States Patent
Won et al.

(10) Patent No.: US 10,618,998 B2
(45) Date of Patent: Apr. 14, 2020

(54) POLY(ALKYLENE CARBONATE)-BASED AMPHIPHILIC BLOCK COPOLYMERS AND METHODS OF USE THEREOF

(71) Applicant: Purdue Research Foundation, West Lafayette, IN (US)

(72) Inventors: You-Yeon Won, West Lafayette, IN (US); Seunggweon Hong, Daejeon (KR); Hoyoung Lee, Daejeon (KR); Jaeyoung Park, Daejeon (KR); Jaewon Lee, Richland, WA (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 15/526,424

(22) PCT Filed: Nov. 12, 2015

(86) PCT No.: PCT/US2015/060430
§ 371 (c)(1),
(2) Date: May 12, 2017

(87) PCT Pub. No.: WO2016/077614
PCT Pub. Date: May 19, 2016

(65) Prior Publication Data
US 2017/0320992 A1    Nov. 9, 2017

Related U.S. Application Data

(60) Provisional application No. 62/078,738, filed on Nov. 12, 2014.

(51) Int. Cl.
*A61K 49/22* (2006.01)
*C08F 293/00* (2006.01)
*C08G 64/18* (2006.01)

(52) U.S. Cl.
CPC ........ *C08F 293/005* (2013.01); *A61K 49/223* (2013.01); *C08G 64/18* (2013.01)

(58) Field of Classification Search
None
See application file for complete search history.

(56) References Cited

U.S. PATENT DOCUMENTS

| | | | | |
|---|---|---|---|---|
| 5,702,717 | A * | 12/1997 | Cha | A61K 9/0024 424/424 |
| 2011/0218127 | A1* | 9/2011 | Allen | C08G 64/0208 507/219 |
| 2012/0129797 | A1* | 5/2012 | Akala | A61K 31/337 514/34 |

OTHER PUBLICATIONS

Sujith S., et al., "A Highly Active and Recyclable Catalytic System for CO2/Propylene Oxide Copolymerization." Angew. Chem. Int. Ed. 2008, 47, 7306-7309.

S. Peng, et al., "Thermal degradation kinetics of uncapped and end-capped poly(propylene carbonate)." Polymer Degradation and Stability 80 (2003) 141-147.

(Continued)

*Primary Examiner* — James W Rogers
(74) *Attorney, Agent, or Firm* — Purdue Research Foundation; Liang Zeng Yan

(57) ABSTRACT

This invention provides poly(alkylene carbonate)-based amphiphilic block copolymers, compositions comprising the same, e.g., micelles, and methods of use thereof. This invention further provides methods for preparing the poly (alkylene carbonate)-based amphiphilic block copolymers of the invention.

3 Claims, 45 Drawing Sheets

(56) References Cited

OTHER PUBLICATIONS

E. Uzunlar, et al., "Thermal and photocatalytic stability enhancement mechanism of poly(propylene carbonate) due to Cu(I) impurities." Polymer Degradation and Stability 97 (2012) 1829e1837.
N. Deshpande, et al., "Molecular ultrasoundimaging:currentstatusand futuredirections." Clinical Radiology65(2010)567e581.
H.S. Min, et al., "Gas-generating polymeric microspheres for long-term and continuous in vivo ultrasound imaging." Biomaterials 33 (2012) 936e944.
T.J. Spencer, et al., "Decomposition of poly(propylene carbonate) with UV sensitive iodonium salts." Polymer Degradation and Stability 96 (2011) 686e702.
Y. Won, et al., "Cryogenic Transmission Electron Microscopy (Cryo-TEM) of Micelles and Vesicles Formed in Water by Poly-(ethylene oxide)-Based Block Copolymers." J. Phys. Chem. B 2002, 106, 3354-3364.
S.C. Owen, et al., "Polymeric micelle stability." Nano Today (2012) 7, 53-65.

* cited by examiner

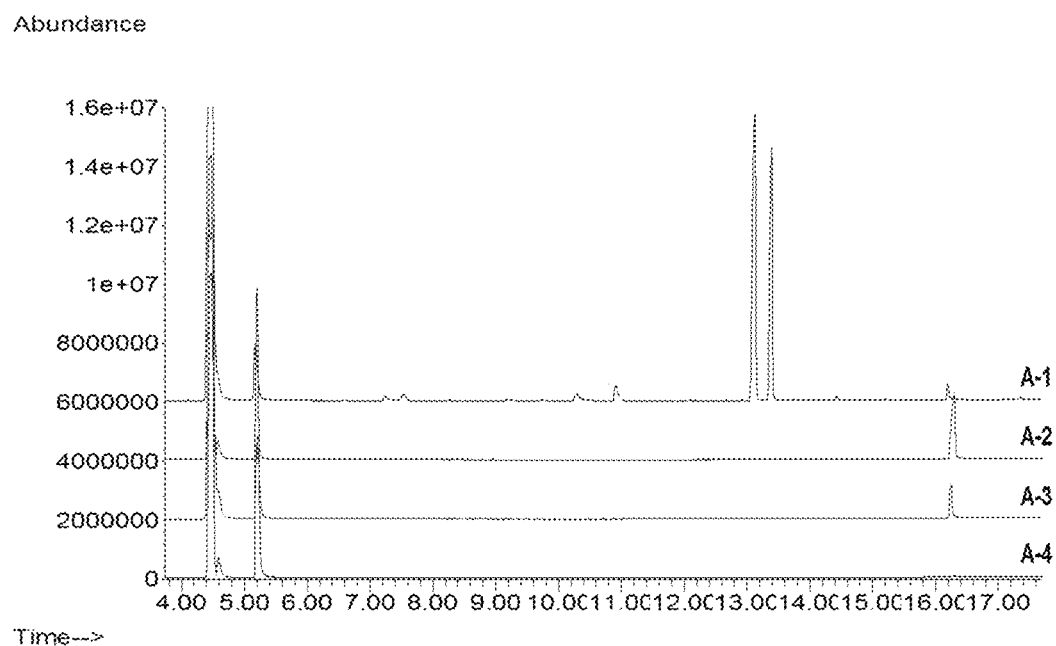
Figure 15 (1)
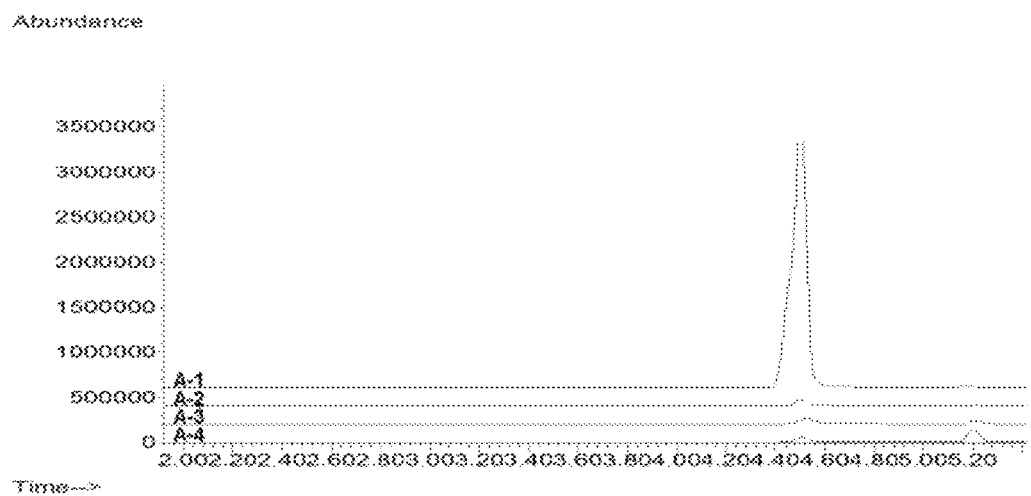
Figure 15 (2)

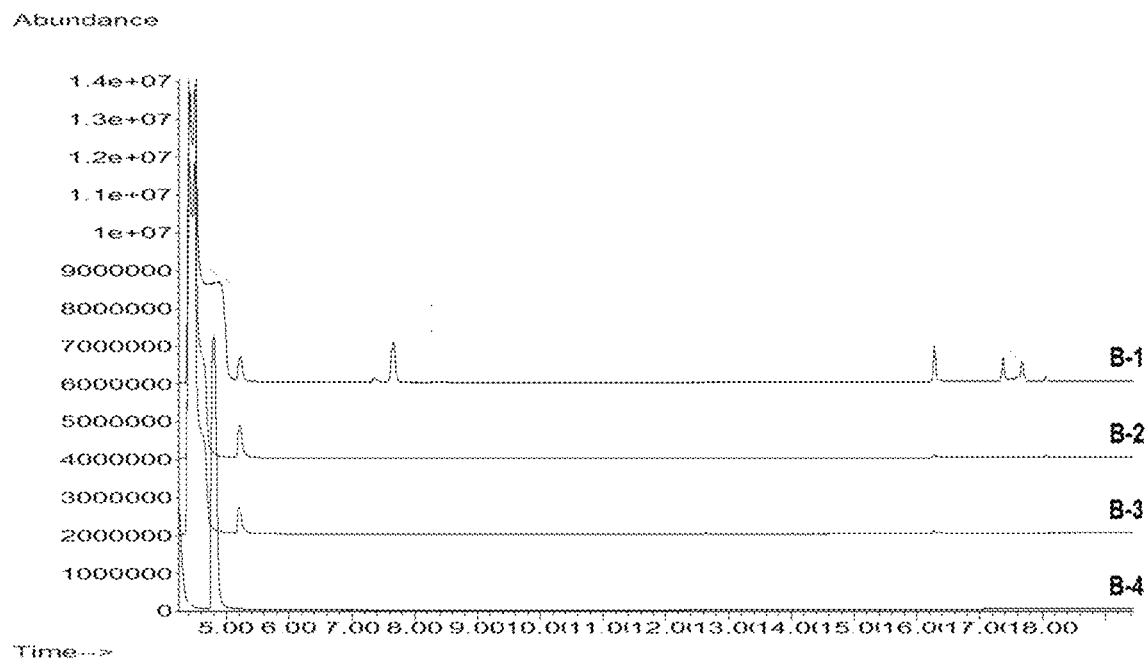
Figure 15 (3)
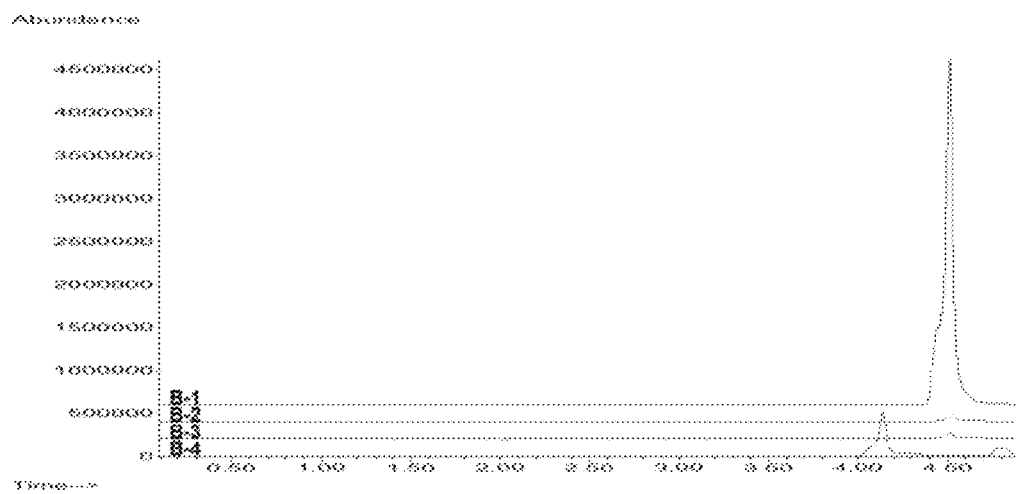
Figure 15 (4)

(A)
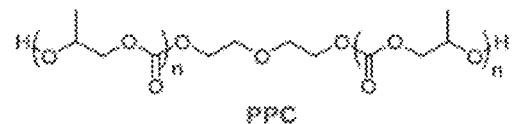
PPC
(B)
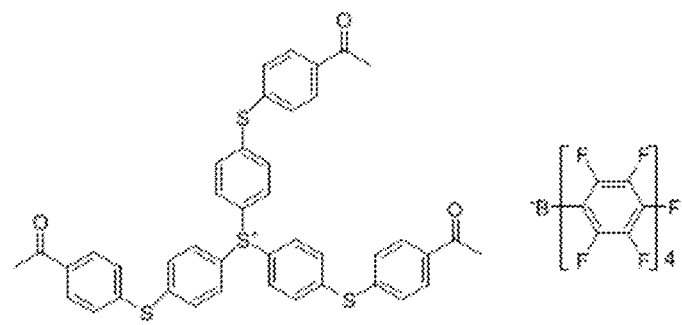
PAG 290
(C)
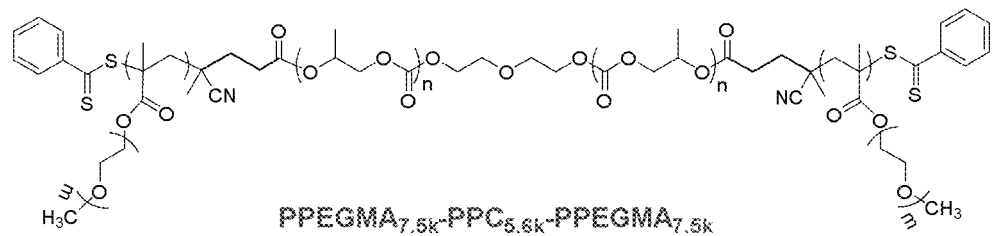
PPEGMA$_{7.5k}$-PPC$_{5.6k}$-PPEGMA$_{7.5k}$
Figure 16

(A)
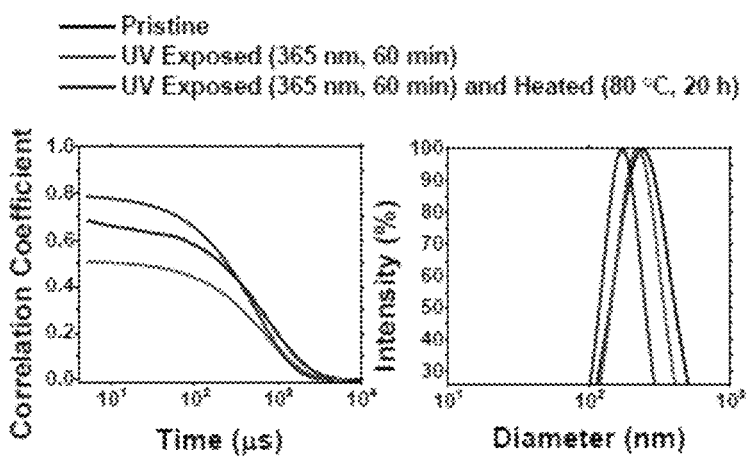
(B)
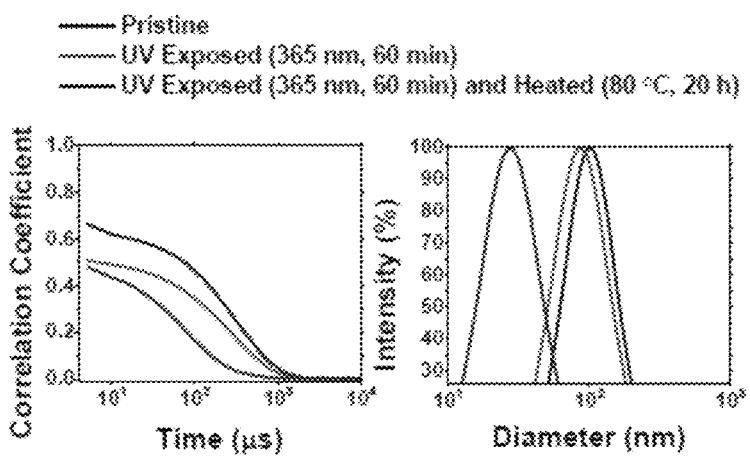
Figure 24

| Polymer ID | GCG2 | GCG3 | GCG4 | GCG5 | GCG6 |
|---|---|---|---|---|---|
| RAFT Initiator | CPCP-PPG6.6k-CPCP | | | | CPCP-PPG2.0k-CPCP |
| CPCP end functionality (%) | 81 | 76 | | | 100 |
| Hydrophilic monomer | Poly(ethylene glycol) methyl ether methacrylate (PEGMA, $M_n$ = 476) | | | | |
| [AIBN] (% of [CPCP]) | 20 | 10 | | 20 | |
| [PEGMA] in THF (M) | 0.2 | 2 | | >1 | >2 |
| $W_{PEGMA}$ (target value) | 30% | 50% | 70% | 60% | 70% |
| Reaction temperature (°C) | 70 | 90 | | | |
| Target yield (g) | 1.0 | 1.0 | 2.0 | 2.0 | 2.0 |
| Expected dispersion morphology | Vesicle | Cylinder | Sphere | Sphere | Sphere |

Figure 27

*Surfactant Packing*

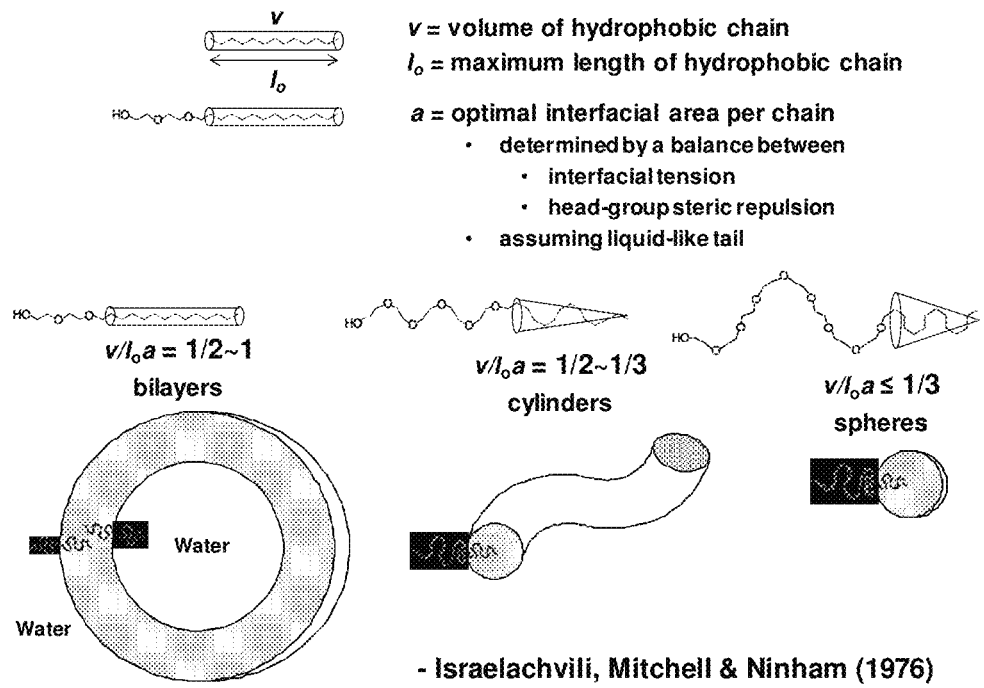

- Israelachvili, Mitchell & Ninham (1976)

Figure 28

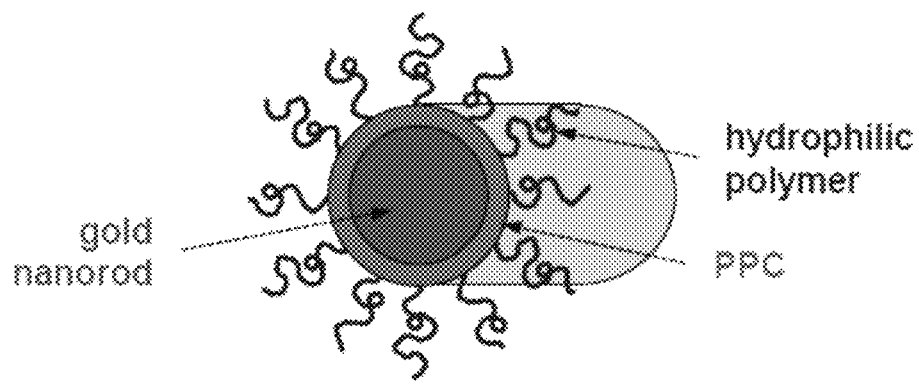
Figure 35
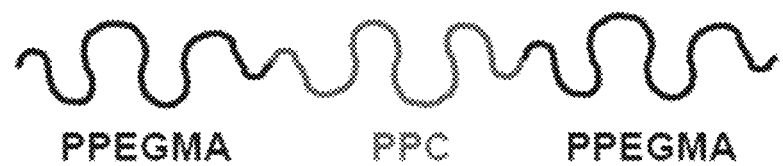
Figure 36
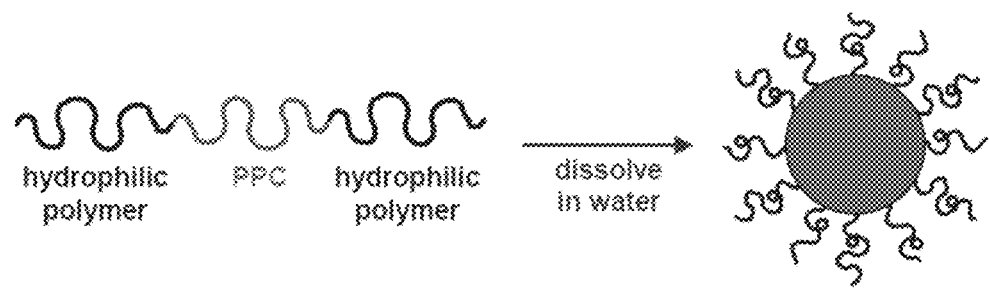
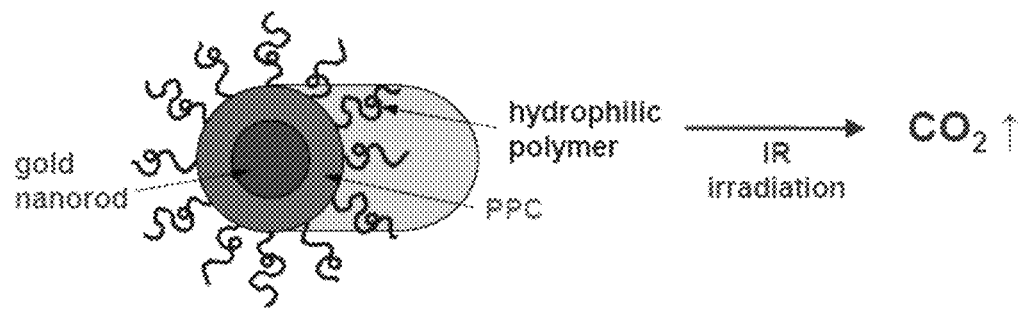
Figure 37

| Polymer ID | 140203A | 140203B | 140210 | 140217 | 140221 |
|---|---|---|---|---|---|
| RAFT initiator | CPCP-PPC$_{5.0k}$-CPCP | | | | CPCP-PPC$_{2.0k}$-CPCP |
| CPCP end functionality (%) | 78 | | | | 100 |
| Hydrophilic monomer | Poly(ethylene glycol) methyl ether methacrylate (PEGMA, M$_n$ = 476) | | | | |
| [AIBN] (% of [CPCP]) | 20 | 10 | 20 | N/A | |
| [PEGMA] in THF (M) | 0.2 | 2 | >1 | >2 | |
| Reaction temperature (°C) | 70 | 90 | | | |
| PPC:PPEGMA weight ratio (target value) | 30:70 | 60:50 | 30:70 | 40:60 | 30:70 |
| PPC:PPEGMA weight ratio (measured value) | 37:63 | 63:37 | 40:60 | 55:45 | 36:64 |
| Yield (g) | 0.25 | 0.62 | 0.97 | 1.11 | 1.0 |
| Polydispersity index (PDI) | 1.42 | 1.52 | 1.42 | 1.44 | 1.47 |

Figure 38

| Polymer ID | 140416 | 140418 | 140425 A | 140425 B | 140519 A | 140519 B | 140612 A | 140612 B | 140617 |
|---|---|---|---|---|---|---|---|---|---|
| RAFT initiator | CPCP-PPC$_{5.0k}$-CPCP | | | | | | | | |
| CPCP end functionality (%) | 73 | 82 | 73 | 72 | 82* | | | | |
| Hydrophilic monomer | Poly(ethylene glycol) methyl ether methacrylate, PEGMA (M$_n$=476) | | | | | | | | |
| [AIBN] (% of [CPCP]) | 20* | | | | | | | | |
| [PEGMA] in THF (M) | 2* | | | | | | | | |
| Reaction temperature (°C) | 90* | | | | | | | | |
| PPC:PEGMA weight ratio (target value) | 25:75 | 40:60 | 50:50 | 30:70 | 35:65 | 35:65 | 40:60 | 40:60 | |
| PPC:PPEGMA weight ratio (measured value) | 42:58 | 28:72 | 60:40 | 85:15 | 34:66 | 65:35 | 84:16 | 80:20 | 69:31 |
| Yield (g) | 1.68 | 2.63 | 2.39 | 2.16 | 2.34 | 1.85 | 1.10 | 1.48 | 2.23 |
| Polydispersity index (PDI) | 1.28 | 1.45 | 1.35 | 1.42 | 1.35 | 1.38 | 1.39 | 1.48 | 1.46 |

Figure 39

| Polymer ID | 140816 | 140823A | 140823B | 140912 | 140913 |
|---|---|---|---|---|---|
| RAFT initiator | CPCP-PPC$_{5.8k}$-CPCP | | | | |
| CPCP end functionality (%) | 66 | 70 | 81 | 81 | 81 |
| Hydrophilic monomer | Poly(ethylene glycol) methyl ether methacrylate (PEGMA, $M_n$ = 476) | | | | |
| [AIBN] (% of [CPCP]) | 10 | | | | |
| [PEGMA] in THF (M) | 1.48 | 0.74 | 0.37 | 0.74 | 0.39 |
| Reaction temperature (°C) | 70 | | | | |
| PPC:PPEGMA weight ratio (target value) | 30:70 | 50:50 | 60:40 | 60:40 | 50:50 |
| PPC:PPEGMA weight ratio (measured value) | 29:72 | 53:48 | 58:42 | 61:39 | 51:49 |
| Yield (g) | 2.12 | 1.53 | 1.41 | 2.07 | 2.57 |
| Polydispersity index (PDI) | 1.36 | 1.37 | 1.40 | 1.33 | 1.29 |

Figure 44

| Polymer ID | | 140418 | 140519A | 140416 | 140217 | 140425A | 140519B | 140221 |
|---|---|---|---|---|---|---|---|---|
| PPC:PEGMA weight ratio | | 28:72 | 34:66 | 42:58 | 55:45 | 60:40 | 65:35 | 36:64 |
| $M_n$ (g/mol) | | 20,063 | 16,398 | 13,418 | 10,191 | 9,405 | 8,587 | 7,854 |
| Time after dissolution at 25 °C (days) | 1 | 66.9 | 782.1 | 49.7 | 1292.4 | 61.9 | 1042.5 | 28.6 |
| | 2 | 54.4 | 633.6 | 44.2 | 1164.5 | 54.6 | 1316.1 | 38.8 |
| | 3 | 53.1 | 629.1 | 42.5 | 985.4 | 50.9 | 1570.7 | 22.4 |
| | 6 | 43.5 | 376.1 | 38.2 | 903.9 | 47.3 | 1275.2 | 32.6 |
| | 8 | 49.3 | 251.4 | 38.5 | 930.3 | 48.9 | 1466.9 | 31.5 |
| | 13 | 38.5 | 202 | 38.1 | 876.6 | 42.3 | 1342.4 | 23.5 |
| | 16 | 41.4 | 174.6 | 35.7 | 932.5 | 43.2 | 1270.4 | 37.9 |
| | 20 | 39.7 | 155.6 | 35.2 | 839.5 | 42.7 | 958.7 | 38.6 |
| | 24 | 39.3 | 150.5 | 33.6 | 744.9 | 41.2 | 788.3 | 35.4 |
| Time after dissolution at 50°C (days) | 1 | 53.5 | 80.8 | 34.2 | | 36.5 | 92.2 | |
| | 2 | 31.9 | 75.1 | 35.2 | | 37.2 | 82.2 | |
| | 3 | 31.1 | 68.1 | 31.2 | | 35.6 | 81.3 | |
| | 6 | 30.8 | 52.8 | 28.1 | | 38.1 | 73.3 | |
| | 8 | 28.6 | 43.9 | 26 | | 33 | 69.1 | |
| | 13 | 24.2 | 35.4 | 28.5 | | 30.5 | 68.2 | |
| | 16 | 27.7 | 25 | 24.5 | | 28.5 | 65.6 | |
| | 20 | 26.4 | 32.7 | 25.7 | | 27.7 | 61.3 | |
| | 24 | 29.2 | 33.8 | 31.2 | | 30.6 | 65.5 | |

Figure 45

| Polymer ID | | 140816 | 140823A | 140823B |
|---|---|---|---|---|
| PPC:PEGMA weight ratio | | 28:72 | 52:48 | 58:42 |
| $M_n$ (g/mol) | | 20,063 | 11,628 | 9,851 |
| Time after dissolution at 25 °C (days) | 1 | 35.9 | 95.9 | 1117.2 |
| | 2 | 36 | 93.3 | 1436.5 |
| | 3 | 32.3 | 87.8 | 1540.1 |
| | 4 | 33.9 | 81.7 | 1557.7 |
| | 5 | 32.2 | 80.4 | 1795.2 |
| | 6 | 29.1 | 73.8 | 1564.9 |
| | 7 | 31.1 | 69.9 | 2358.6 |
| | 8 | 30.6 | 69.7 | 1578.8 |
| | 9 | 30.3 | 68.1 | 1347.6 |
| | 10 | 29.1 | 66.4 | 1672 |
| | 13 | 27 | 60.5 | 1216.3 |

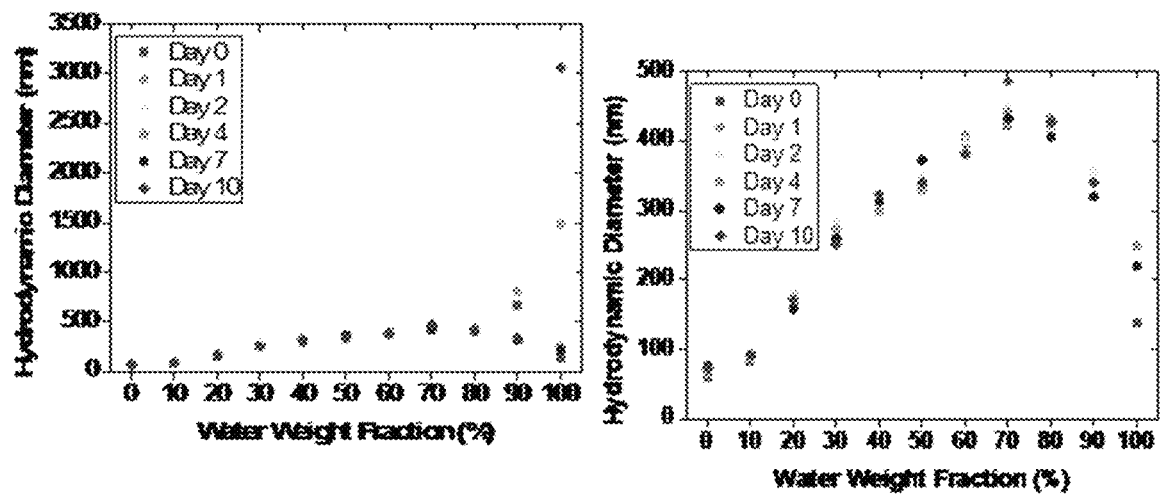

Figure 70

| Trial No. | Polymer Used | GNR Purification Procedure | Water:DMF Weight Ratio at Solvent Exchange | Hydrodynamic Diameter of BCP-Encapsulated GNRs in the Water/DMF Mixture Immediately after Solvent Exchange (nm) | Hydrodynamic Diameter of BCP-Encapsulated GNRs in Water at Day 0, i.e., immediately after Dialysis (nm) |
|---|---|---|---|---|---|
| 1 | 140816 (PPC:PPEGMA = 28:72 by weight, $M_n$ = 20.1 kg/mol) | As-synthesized | 40:60 | 84 | 83 |
| 2 | | Precipitated | 40:60 | 203 | 200 |
| 3 | | Precipitated + Centrifuged | 45:55 | 338 | 247 |
| 4 | 140823A (PPC:PPEGMA = 52:48 by weight, $M_n$ = 11.6 kg/mol) | As-synthesized | 35:65 | 63 | 60 |
| 5 | | Precipitated | 35:65 | 210 | 93 |
| 6 | | Precipitated + Centrifuged | 35:65 | 40 | 69 |
| 7 | 140823B (PPC:PPEGMA = 58:42 by weight, $M_n$ = 9.9 kg/mol) | As-synthesized | 40:60 | 90 | 73 |
| 8 | | Precipitated | 40:60 | TBD | TBD |
| 9 | | Precipitated + Centrifuged | 40:60 | 33 | 82 |

Figure 71

POLY(ALKYLENE CARBONATE)-BASED AMPHIPHILIC BLOCK COPOLYMERS AND METHODS OF USE THEREOF

CROSS-REFERENCE TO RELATED APPLICATIONS

The present application is a national stage entry under 35 U.S.C. § 371 of International Application No. PCT/US2015/060430, filed on Nov. 12, 2015, which claims priority under 35 U.S.C. § 119(e) to U.S. Provisional Application Ser. No. 62/078,738, filed on Nov. 12, 2014, the contents of which are hereby incorporated by reference in its entirety into this disclosure.

FIELD OF THE INVENTION

The present invention relates to poly(alkylene carbonate)-based amphiphilic block copolymers, to compositions comprising the same, e.g., micelles, and to methods of use thereof.

BACKGROUND OF THE INVENTION

Poly(alkylene carbonate) materials, such as poly(propylene carbonate), have been recognized as a promising material for pharmaceutical and biomedical applications due to their biodegradable and biocompatible nature. One biomedical application of these materials is their ability to release gas upon decomposition. Such materials can then be bound to a target site within a patient body and triggered to release gas bubbles. The released gas can be identified by various imaging techniques, for example, by ultrasound. Using such procedure, the location of the target site can be determined as it is correlated to the gas producing region. Further, treatment of the target site can be pursued based on the established coordinates of the site.

The gas release temperature must be biocompatible and this temperature range limits the gas releasing materials that can be used. The gas releasing materials should be stable in aqueous environment in order to be transported through the body. The amount of gas formed upon triggering of the material should be high enough for sensing the gas by an imaging tool.

Poly(propylene carbonate) (PPC) can produce $CO_2$ as its thermal degradation byproduct. However, for production of $CO_2$ from bulk PPC, the thermal degradation process occurs at temperatures greater than about 200° C. Further, bulk PPC is not water-soluble. Additionally, the gas generated inside the PPC bulk may diffuse away to a surrounding aqueous solution. Thus, PPC was not considered to be useful as a $CO_2$-generating material for use as a contrast agent in medical imaging and treatment.

SUMMARY OF THE INVENTION

It is one aspect of this invention that features the utility of a block copolymer (BCP) comprising poly(propylene carbonate) (PPC) in biomedical imaging and related applications.

In another aspect, the present invention provides a block copolymer comprising hydrophilic polymer segment A and a poly(alkylene carbonate) segment B.

In some embodiments, the poly(alkylene carbonate) is poly(propylene carbonate) (PPC). In some embodiments, the hydrophilic polymer is poly(poly(ethylene glycol) methyl ether methacrylate) (PPEGMA).

In another aspect, this invention provides a micelle comprising a block copolymer, wherein the block copolymer comprises a hydrophilic polymer segment A and a poly(alkylene carbonate) segment B. In some embodiments, the hydrophilic segment comprises PPEGMA. In other embodiments, the poly(alkylene carbonate) segment is PPC.

In another aspect, this invention provides a method of preparing a micelle comprising a block copolymer and a photoacid generator (PAG), the method comprising:
co-dissolving a block copolymer and PAG in an organic solvent to form a solution;
dialyzing, or directly mixing, the solution against deionized water;
optionally adding water to adjust micelle concentration.

In some embodiments, the block copolymer comprises a hydrophilic polymer segment A and a poly(alkylene carbonate) segment B. In some embodiments, the hydrophilic segment comprises PPEGMA and the poly(alkylene carbonate) segment comprising PPC. In some embodiments, the PAG comprises tris ([4-([4-acetylphenyl]sulfanyl)phenyl]) sulfanium tetrakis (pentafluorophenyl) borate.

In another aspect, this invention provides a method for target site imaging, the method comprising:
delivering a micelle comprising BCP and PAG to a target site;
irradiating or heating said micelle using radiation in the infrared (IR)/near-IR range;
imaging gas bubbles released from the BCP upon irradiation or heating;
wherein the BCP comprising a poly(alkylene carbonate) segment (B) and a hydrophilic segment (A).

The details of one or more embodiments of the invention are set forth in the accompanying the description below. Other features, objects, and advantages of the invention will be apparent from the description and drawings, and from the claims.

BRIEF DESCRIPTION OF THE DRAWINGS

FIG. 15 depicts GC/MS traces of the gas-phase degradation products of the (1) UV-exposed, (2) UV-unexposed PPC/PAG 290 mixtures (both prepared using GBL as the casting solvent), and (3) GBL-cast and (4) non-cast pure PPC controls. The thermal degradation reactions were performed under either (A) dried or (B) hydrated conditions by heating the samples at 80° C. for 20 hours in a closed chamber filled with air at atmospheric pressure. Concentration values in the y-axis represent relative abundances in arbitrary units, and time in units of minutes along the horizontal axis.

FIG. 16 shows chemical structures of (A) the dihydroxyl poly(propylene carbonate) (PPC), (B) the photoacid generator, BASF Irgacure PAG 290, and (C) the poly(poly(ethylene glycol) methyl ether methacrylate)-poly(propylene carbonate)-poly(poly(ethylene glycol) methyl ether methacrylate) (PPEGMA-PPC-PPEGMA) triblock copolymer.

FIG. 24 depicts dynamic light scattering (DLS) data for the PAG 290-containing PPEGMA-PPC-PPEGMA micelles under three different conditions: before exposure to UV light, after exposure to UV irradiation (365 nm, 20 mW/cm$^2$, 60 minutes) with no heating, and after exposure to UV irradiation (365 nm, 20 mW/cm$^2$, 60 minutes) and heating at 80° C. for 20 hours. The PAG 290-containing polymer micelles were prepared by solvent exchange using either (A) GBL or (B) DMF as the initial co-dissolution solvent.

FIG. 27 shows polymer properties

FIG. 28 shows surfactant packing geometries

FIG. 35 shows the concept of gold nanorods (GNR's) encapsulated into PPEGMA-PPC-PPEGMA micelles.

FIG. 36 depicts a scheme of a tri-block copolymer of the form A-B-A comprising PPEGMA-PPC-PPEGMA (PPEGMA=A and PPC=B).

FIG. 37 shows the formation of micelles or nanoparticles by dissolving a tri-block copolymer comprising PPC and hydrophilic segments in water. The figure further demonstrates the scheme for $CO_2$ release upon heating of a gold nanorod coated by a polymer comprising PPC and hydrophilic segment.

FIG. 38 depicts a summary of RAFT polymerization conditions and molecular characteristics of PPEGMA-PPC-PPEGMA triblock copolymers.

FIG. 39 depicts a summary of RAFT polymerization conditions and molecular characteristics of PPEGMA-PPC-PPEGMA triblock copolymers.

FIG. 44 depicts a summary of RAFT polymerization conditions and molecular characteristics of PPEGMA-PPC-PPEGMA triblock copolymers synthesized.

FIG. 45 shows the hydrodynamic diameters (nm) of particles formed in water by PPEGMA-PPC-PPEGMA polymers (2.0 wt. %) via direct hydration.

FIG. 70 depicts hydrodynamic diameters.

FIG. 71 depicts a summary of conditions used for encapsulation of GNRs in PPEGMA-PPC-PPEGMA micelles.

Figure 1:
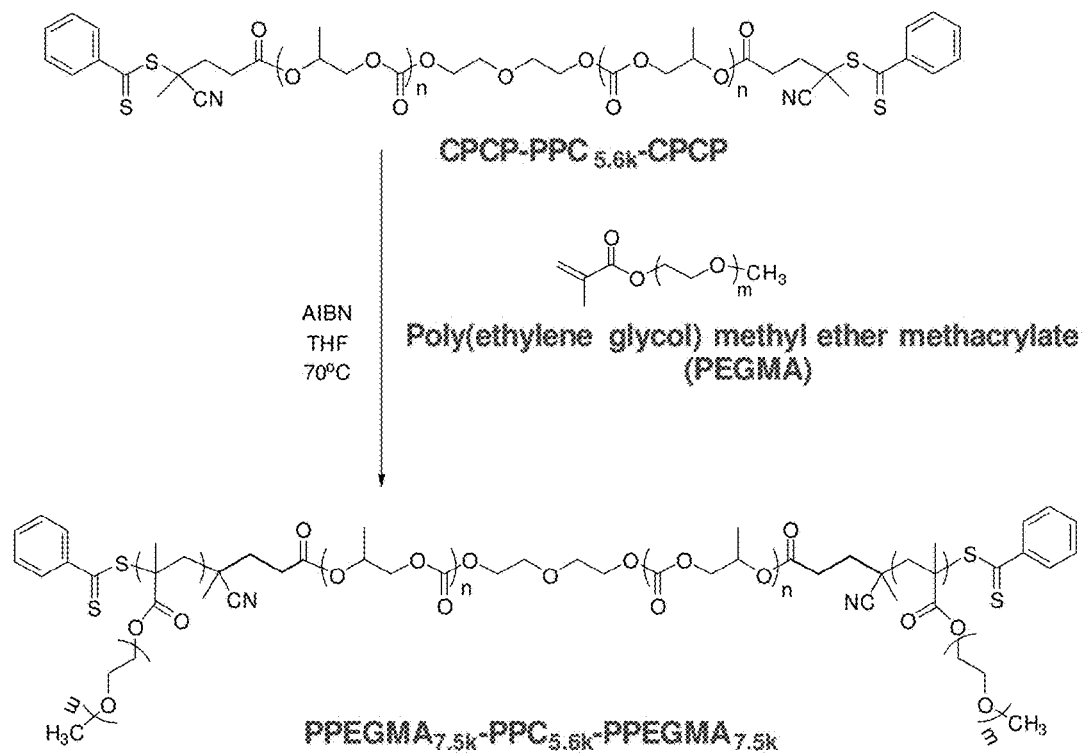
FIG. 1 depicts a synthesis route for the preparation of PPEGMA-PPC-PPEGMA tri-block copolymers via RAFT polymerization of PEGMA using dithioester-functionalized PPC as the macroinitiator.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one aspect, this invention features the utility of a block copolymer comprising poly(propylene carbonate) (PPC) in biomedical imaging and related applications.

In another aspect, this invention provides a block copolymer comprising hydrophilic polymer segment A and a poly(alkylene carbonate) segment B.

In some embodiments, the poly(alkylene carbonate) is poly(propylene carbonate) (PPC). In some embodiments, the hydrophilic polymer is poly(poly(ethylene glycol) methyl ether methacrylate) (PPEGMA).

In some embodiments, the block copolymers of the present invention comprise di-block copolymers. In some embodiments, the block copolymers of the invention comprise tri-block copolymers. In other embodiments, di-block copolymers of the invention comprise two polymeric chains attached to each other at one end. In some embodiments, tri-block copolymers comprise a central polymeric chain attached to a second polymer chain at its first end and further attached to a third polymer chain at its second end.

In some embodiments, the block copolymer comprises a di-block copolymer, a tri-block copolymer, or a combination thereof. In some embodiments, the block copolymer is a tri-block copolymer in the form of A-B-A. In certain embodiments, A represents the hydrophilic segment (e.g., PPEGMA) and B represents PPC. In other embodiments, the block copolymer is a di-block copolymer in the form of A-B. In some embodiments, A represents PPEGMA and B represents PPC.

In some embodiments, the block copolymers of the invention comprise linear polymers. In some embodiments, the polymers of the invention are star polymers. In some embodiments, the linear block copolymers comprise two or more polymer chains in sequence. In other embodiments, the star block copolymer comprises more than two linear block copolymers attached at a common branch point.

The block copolymers of the present invention are useful in many applications where a number of different polymers are connected together to yield a material with hybrid properties. For example, attachment of a water soluble polymer to a water insoluble polymer forms an amphiphilic copolymer that may form micelles in solution. Potential applications of such material include drug encapsulants, surfactants, emulsifiers, detergents, wetting/foaming agents, viscosity modification agents, and dispersants.

In some embodiments, the block copolymer is described as a polymeric chain comprising "A" units (components) and "B" units (components). For example, the block copolymer of the present invention can be a di-block copolymer represented in the form of A-B. In another embodiment, the block copolymer of the present invention is a tri-block copolymer in the form of A-B-A. In another embodiment, the block copolymer of the present invention is a tri-block copolymer in the form of B-A-B. In another embodiment, one component polymer (e.g., polymer A) of the block copolymer of this invention is ionic. In some embodiments, the block copolymer of this invention is amphiphilic.

In some embodiments, the "A" component is selected from the group consisting of water-compatible polymer materials. The water-compatible polymer materials include, but are not limited to, poly(poly(ethylene glycol) methyl ether methacrylate) (PPEGMA) (nonionic), poly(acrylic acid) (anionic), poly(methacrylic acid) (anionic), poly(carboxyethyl(or propyl) acrylate) (anionic), poly(carboxyethyl (or propyl) methacrylate) (anionic), poly(sulfopropyl(or ethyl) acrylate) (anionic), poly(sulfopropyl(or ethyl) methacrylate) (anionic), poly(styrene sulfonate) (anionic), poly (2-(dimethylamino)ethyl(or propyl) acrylate) (and its quarternized product) (cationic), poly(2-(dimethylamino)ethyl (or propyl) methacrylate) (and its quarternized product) (cationic), poly(2(or 4)-vinyl pyridine) (and its quarternized product) (cationic), poly(ethylenimine) (cationic), poly(N-isopropylacrylamide) (nonionic), poly(N,N-dimethylacrylamide) (nonionic), and poly(ethyl(or methyl) oxazoline) (nonionic).

In some embodiments, the "A" component is poly(poly (ethylene glycol) methyl ether methacrylate) (PPEGMA). In some embodiments, the "A" component is poly(acrylic acid), poly(methacrylic acid), poly(carboxyethyl acrylate), or poly(carboxypropyl acrylate). In other embodiments, the "A" component is poly(carboxyethyl methacrylate), poly(carboxypropyl methacrylate), poly(sulfopropyl acrylate), poly(sulfoethyl acrylate), poly(sulfopropyl methacrylate), poly(sulfoethyl methacrylate), or poly(styrene sulfonate). In certain embodiments, the "A" component is poly(2-(dimethylamino)ethyl(or propyl) acrylate) (and its quaternized product), poly(2-(dimethylamino)ethyl(or propyl) methacrylate) (and its quaternized product), or poly(2(or 4)-vinyl pyridine) (and its quaternized product). In some embodiments, the "A" component is poly(ethylenimine), poly(N-isopropylacrylamide), poly(N,N-dimethylacrylamide), or poly(ethyl(or methyl) oxazoline).

In some embodiments, the "B" component is selected from the group consisting of poly(alkylene carbonate) materials. The "B" component materials include, but are not limited to, poly(propylene carbonate) (PPC), poly(ethylene carbonate), poly(butylene carbonate), poly(pentylene carbonate), poly(hexylene carbonate), poly(octylene carbonate), and poly(dodecylene carbonate). In some embodiments, the "B" component is poly(propylene carbonate) (PPC). In other embodiments, the "B" component is poly(ethylene carbonate), poly(butylene carbonate), poly(pentylene carbonate), poly(hexylene carbonate), poly(octylene carbonate), or poly(dodecylene carbonate).

In some embodiments, polymer A comprises PPEGMA and polymer B comprises PPC. By way of example, poly(poly(ethylene glycol) methyl ether methacrylate)-poly(propylene carbonate)-poly(poly(ethylene glycol) methyl ether methacrylate) (PPEGMA-PPC-PPEGMA) triblock copolymers have been synthesized.

In some embodiments, polymer A and polymer B or a combination thereof are chosen such as to exhibit substantially longer half-lives in blood following intravenous injection. Such polymers may also increase the compound's solubility in aqueous solution, eliminate aggregation, enhance the physical and chemical stability of a polymer-coated nanoparticle and greatly reduce the immunogenicity of the coated nanoparticles. Thus, the desired in vivo biological activity may be achieved by the administration of such polymers or a composition comprising the polymer, e.g., the micelle of the present invention.

In some embodiments, the block copolymer is PPEGMA-PPC-PPEGMA. In other embodiments, the average weight molecular weight of PPEGMA is from about 500 Da to about 500,000 Da. In some embodiments, the average weight molecular weight of PPEGMA is from about 144 Da to about 500,000 Da. In some embodiments, the average weight molecular weight of PPEGMA is from about 250 Da to about 250,000 Da. In some embodiments, the average weight molecular weight of PPEGMA is from about 500 Da to about 250,000 Da. In other embodiments, the average weight molecular weight of PPEGMA is from about 500 Da to about 100,000 Da. In certain embodiments, the average weight molecular weight of PPEGMA is from about 500 Da to about 75,000 Da. In some embodiments, the average weight molecular weight of PPEGMA is from about 500 Da to about 50,000 Da. In other embodiments, the average weight molecular weight of PPEGMA is from about 1,000 Da to about 250,000 Da. In some embodiments, the average weight molecular weight of PPEGMA is from about 5,000 Da to about 250,000 Da. In some embodiments, the average weight molecular weight of PPEGMA is from about 10,000 Da to about 250,000 Da. In certain embodiments, the average weight molecular weight of PPEGMA is from about 50,000 Da to about 250,000 Da. In other embodiments, the average weight molecular weight of PPEGMA is from about 75,000 Da to about 250,000 Da. In some embodiments, the average weight molecular weight of PPEGMA is from about 100,000 Da to about 250,000 Da. In some embodiments, the average weight molecular weight of PPEGMA is from about 50,000 Da to about 100,000 Da.

In some embodiments, the average weight molecular weight of PPC is from 500 Da to about 500,000 Da. In some embodiments, the average weight molecular weight of PPC is from 200 Da to about 500,000 Da. In other embodiments, the average weight molecular weight of PPC is from 500 Da to about 250,000 Da. In some embodiments, the average weight molecular weight of PPC is from 500 Da to about 100,000 Da. In other embodiments, the average weight molecular weight of PPC is from 500 Da to about 50,000 Da. In some embodiments, the average weight molecular weight of PPC is from 500 Da to about 10,000 Da. In certain embodiments, the average weight molecular weight of PPC is from 10,000 Da to about 500,000 Da. In some embodiments, the average weight molecular weight of PPC is from 50,000 Da to about 500,000 Da. In other embodiments, the average weight molecular weight of PPC is from 100,000 Da to about 500,000 Da. In certain embodiments, the average weight molecular weight of PPC is from 50,000 Da to about 100,000 Da.

In some embodiments, the PPC-type ("B") component of the block copolymer can range from 5 to 95 percent by weight from the total weight of the polymer. For example, in some embodiments, the PPC-type ("B") component of the block copolymer can range from 10 to 95 percent by weight from the total weight of the polymer. In other embodiments, the PPC-type ("B") component of the block copolymer can range from 25 to 95 percent by weight from the total weight of the polymer. In some embodiments, the PPC-type ("B") component of the block copolymer can range from 50 to 95 percent by weight from the total weight of the polymer. In certain embodiments, the PPC-type ("B") component of the block copolymer can range from 75 to 95 percent by weight from the total weight of the polymer. In some embodiments, the PPC-type ("B") component of the block copolymer can range from 5 to 75 percent by weight from the total weight of the polymer. In other embodiments, the PPC-type ("B") component of the block copolymer can range from 5 to 50 percent by weight from the total weight of the polymer. In certain embodiments, the PPC-type ("B") component of the block copolymer can range from 5 to 25 percent by weight from the total weight of the polymer. In some embodiments, the PPC-type ("B") component of the block copolymer can range from 25 to 75 percent by weight from the total weight of the polymer. In other embodiments, the PPC-type ("B") component of the block copolymer can range from 25 to 50 percent by weight from the total weight of the polymer.

In some embodiments, the overall molecular weight of the block copolymer can range from 1,000 g/mol to 1,000,000 g/mol. In some embodiments, the overall molecular weight of the block copolymer can range from 1,000 g/mol to 750,000 g/mol. In some embodiments, the overall molecular weight of the block copolymer can range from 1,000 g/mol to 500,000 g/mol. In other embodiments, the overall molecular weight of the block copolymer can range from 1,000 g/mol to 250,000 g/mol. In some embodiments, the overall molecular weight of the block copolymer can range from 5,000 g/mol to 1,000,000 g/mol. In other embodiments, the overall molecular weight of the block copolymer can range from 10,000 g/mol to 1,000,000 g/mol. In some embodiments, the overall molecular weight of the block copolymer can range from 50,000 g/mol to 1,000,000 g/mol.

In some embodiments, the overall molecular weight of the block copolymer can range from 100,000 g/mol to 1,000,000 g/mol. In certain embodiments, the overall molecular weight of the block copolymer can range from 500,000 g/mol to 1,000,000 g/mol. In some embodiments, the overall molecular weight of the block copolymer can range from 10,000 g/mol to 500,000 g/mol.

In some embodiments, the block copolymer is linked to the surface of a nanoparticle. The block copolymer comprises a hydrophobic part ("A") and a hydrophilic part ("B"). In some embodiments, the hydrophilic part is selected so as to render the nanoparticle soluble in an aqueous solution. In some embodiments, the hydrophobic part is selected so as to enable $CO_2$ evolution from the polymer. In other embodiments, the hydrophobic part is selected so as to enable bonding between the hydrophilic part of the block copolymer and a nanoparticle. In some embodiments, the PPC (hydrophobic) part of the block copolymer is attached to a nanoparticle and the PPEGMA (hydrophilic) part is exposed to the environment. Such a novel amphiphilic BCP structure is biocompatible.

In some embodiments, polymer A and polymer B are hydrophilic. In some embodiments, polymer A is hydrophilic and polymer B is hydrophobic. In some embodiments, the hydrophilicity level of polymers A and B is designed so that polymer A will provide solubility in aqueous solutions and in the blood stream, and will be located on the outer surface of the micelle, the polymeric particle, or the polymer-coated nanoparticle. In some embodiments, the hydrophilicity level of polymers A and B is designed so that polymer B will bind to the surface of the nanoparticle, or will provide the inner portion of a micelle or of another polymeric particle. In some embodiments, polymers A and B are non-toxic. In some embodiments, polymers A and B are biocompatible and biodegradable. In some embodiments, polymer A and polymer B or a combination thereof are nonionic. In another embodiment, polymer A and polymer B are ionic.

Micelles of the Invention

In another aspect, this invention provides a composition comprising a block copolymer, wherein the block copolymer comprising poly(alkylene carbonate) segment B and a hydrophilic segment A. In some embodiments, the composition is in the form of micelle. In some embodiments, poly(alkylene carbonate) segment comprises PPC. In some embodiments, the hydrophilic segment comprises PPEGMA. In some embodiments, the hydrophilic segment comprises PPEGMA and the poly(alkylene carbonate) segment is PPC. In some embodiments, the composition of the present invention comprises, in addition to the block copolymer, a carrier or diluent known in the art.

In another aspect, this invention provides a micelle comprising a block copolymer, wherein the block copolymer comprising poly(alkylene carbonate) segment B and a hydrophilic segment A. In some embodiments, poly(alkylene carbonate) segment comprises PPC. In some embodiments, the hydrophilic segment comprises PPEGMA. In some embodiments, the hydrophilic segment comprises PPEGMA and the poly(alkylene carbonate) segment is PPC. In some embodiments, the micelle further comprises a photoacid generator (PAG). Exemplary photoacid generators include, but are not limited to, BASF non-ionic photoacid generators (e.g., Irgacure PAG 103, Irgacure PAG 121, Irgacure PAG 203, CGI 725, and CGI 1907), BASF ionic photoacid generators (e.g., Irgacure 250, Irgacure PAG 290, and GSID26-1), (tert-butoxycarbonylmethoxynaphthyl)-diphenylsulfonium triflate (Sigma-Aldrich), bis(4-tert-butylphenyl)iodonium triflate (Sigma-Aldrich), N-hydroxynaphthalimide triflate (Sigma-Aldrich), diphenyliodonium perfluoro-1-butanesulfonate (Sigma-Aldrich), tris(4-tert-butylphenyl)sulfonium perfluoro-1-butanesulfonate (Sigma-Aldrich), N-hydroxynaphthalimide perfluoro-1-butanesulfonate (Midori Kagaku Co.), 4-methylphenyl[4-(1-methylethyl)phenyl]iodonium tetrakis (pentafluorophenyl)borate (Rhodia), tris(4-tert-butylphenyl)sulfonium tetrakis-(pentafluorophenyl)borate (Rhodia), triphenylsulfonium tetrakis-(pentafluorophenyl)borate (Rhodia), bis(4-tert-butylphenyl)iodonium p-toluenesulfonate (Sigma-Aldrich), diphenyliodomium 9,10-dimethoxyanthracene-2-sulfonate (Sigma-Aldrich), Ciba non-ionic photoacid generator, bis(4-tert-butylphenyl)iodonium tris(perfluoromethanesulfonyl)methide (3M Corporation), bis(4-tert-butylphenyl)iodonium bis(perfluorobutanesulfonyl)imide (3M Corporation), and bis(4-tert-butylphenyl)iodonium perfluoro-1-octanesulfonate (Midori Kagaku Co.).

In some embodiments, the PAG is tris ([4-([4-acetylphenyl]sulfanyl)phenyl]) sulfanium tetrakis (pentafluorophenyl) borate.

In some embodiments, the block copolymer is a tri-block copolymer in the form of A-B-A, wherein A represents PPEGMA and B represents PPC and wherein the PAG comprises tris ([4-([4-acetylphenyl]sulfanyl)phenyl]) sulfanium tetrakis (pentafluorophenyl) borate. In some embodiments, the block copolymer of the micelle is a di-block copolymer in the form of A-B, wherein A represents PPEGMA and B represents PPC.

In some embodiments, the micelle is formed in an aqueous media, e.g., water.

In some embodiments, the micelle degrades at a temperature of from about 40° C. to about 80° C. In other embodiments, the micelle degrades at a temperature of from about 40° C. to about 85° C. In other embodiments, the micelle degrades at a temperature of from about 40° C. to about 90° C. In certain embodiments, the micelle degrades at a temperature of from about 50° C. to about 70° C.

In some embodiments, the micelle releases gas when degrading. In certain embodiments, the micelle releases $CO_2$ when degrading.

In some embodiments, the micelle further comprises a Lewis or Brönsted acid. In some embodiments, the acid is generated in the presence of a photo-acid generator, for example, a photoacid generator as described herein.

In some embodiments, the micelles of the invention comprise di-block copolymers. In some embodiments, the micelles of this invention comprise tri-block copolymers. In some embodiments, the micelles of this invention are stable in water. In some embodiments, the micelles of this invention are stable in aqueous solutions. In some embodiments, the micelles comprise PPC-PPEGMA di-block copolymers. In some embodiments, the micelles comprise PPEGMA-PPC-PPEGMA tri-block copolymers.

In some embodiments, the micelles are spherical. In some embodiments, the diameter of the micelles is about 40 nm. In some embodiments, the diameter of the micelles ranges from about 10 to about 1,000 nm. In some embodiments, the diameter of the micelles ranges from about 10 to about 500 nm. In some embodiments, the diameter of the micelles ranges from about 10 to about 100 nm. In other embodiments, the diameter of the micelles ranges from about 25 to about 1,000 nm. In some embodiments, the diameter of the micelles ranges from about 40 to about 1,000 nm. In other embodiments, the diameter of the micelles ranges from about 40 to about 250 nm. In certain embodiments, the diameter of the micelles ranges from about 40 to about 100 nm. In some embodiments, the diameter of the micelles ranges from about 40 to about 75 nm. In certain embodiments, the diameter of the micelles ranges from about 25 to about 75 nm.

In another aspect, this invention provides methods of preparing micelles. In some embodiments, this present invention provides a method of preparation of a micelle comprising a block copolymer, wherein the block copolymer comprises poly(alkylene carbonate) segment B and a hydrophilic segment A.

In some embodiments, this invention provides a method of preparing a micelle comprising a block copolymer, wherein the block copolymer comprises PPC. In some embodiments, this invention provides a method of preparing a micelle comprising a block copolymer, wherein the block copolymer comprises PPEGMA.

In some embodiments, this invention provides a method of preparing a micelle comprising a block copolymer, wherein the block copolymer comprises PPEGMA and PPC. In some embodiments, the block copolymer is a tri-block copolymer in the form of A-B-A, wherein A represents PPEGMA and B represents PPC. In some embodiments, the micelle prepared by methods of the invention further comprises a photoacid generator (PAG). In some embodiments, the PAG is tris ([4-([4-acetylphenyl]sulfanyl)phenyl]) sulfanium tetrakis (pentafluorophenyl) borate.

In some embodiments, this invention provides a method of preparing a micelle comprising a PPC-PPEGMA block copolymer and PAG, the method comprising:
co-dissolving PPEGMA-PPC-PPEGMA tri-block copolymer and PAG in an organic solvent to form a solution;
dialyzing, or directly mixing, said solution against an aqueous media, such as deionized water;
optionally adding water to adjust micelle concentration.

In some embodiments, the PAG is Irgacure® PAG 290 (BASF). In some embodiments, the organic solvent comprises gamma-butyrolactone (GBL). In other embodiments, the organic solvent comprises N,N-dimethylformamide (DMF).

In some embodiments, the weight ratio of PPC:PAG is from about 99.99:0.01 to about 80:20. In some embodiments, the weight ratio of PPC:PAG is from about 99.50:0.50 to about 80:20. In other embodiments, the weight ratio of PPC:PAG is from about 99.00:1.00 to about 80:20. In some embodiments, the weight ratio of PPC:PAG is from about 98.00:2.00 to about 80:20. In other embodiments, the weight ratio of PPC:PAG is from about 97.00:3.00 to about 80:20. In certain embodiments, the weight ratio of PPC:PAG is from about 96.00:4.00 to about 80:20. In other embodiments, the weight ratio of PPC:PAG is from about 95.00:5.00 to about 80:20. In some embodiments, the weight ratio of PPC:PAG is from about 94.00:6.00 to about 80:20. In some embodiments, the weight ratio of PPC:PAG is from about 93.00:7.00 to about 80:20. In other embodiments, the weight ratio of PPC:PAG is 92.00:8.00. In some embodiments, the weight ratio of PPC:PAG is from about 91.00:9.00 to about 80:20. In certain embodiments, the weight ratio of PPC:PAG is from about 90.00:10.00 to about 80:20. In some embodiments, the PPC concentration in the micelle solution is about 5 mg/mL.

Polymer-encapsulated Nanoparticles

In some embodiments, this invention provides a polymer-coated nanoparticle wherein the nanoparticle coating comprises a block copolymer, wherein the block copolymer comprises a poly(alkylene carbonate) segment (B) and a hydrophilic segment (A). In some embodiments, this invention provides a polymer-coated nanoparticle comprising a block copolymer, wherein the block copolymer comprises a PPC segment (B). In some embodiments, this invention provides a polymer-coated nanoparticle comprising a block copolymer, wherein the block copolymer comprises a PPEGMA segment (A).

In some embodiments, this invention provides a polymer-coated nanoparticle comprising a block copolymer, wherein the block copolymer comprises PPEGMA and PPC. In some embodiments, the polymer-coated nanoparticle further comprises a photoacid generator (PAG). In some embodiments, the PAG is located in the polymeric coating of the nanoparticle. In some embodiments, the PAG is located within the hydrophobic portion of the BCP. In some embodiments, the PAG is located within the PPC portion of the block copolymer.

In some embodiments, the block copolymer coating of the nanoparticle is a tri-block copolymer in the form of A-B-A, wherein A represents PPEGMA and B represents PPC and wherein the PAG comprises tris ([4-([4-acetylphenyl]sulfanyl)phenyl]) sulfanium tetrakis (pentafluorophenyl) borate (PAG 290).

In some embodiments, the nanoparticle coating further comprises an acid. In some embodiments, the acid in the polymer coating is generated in the presence of PAG.

In some embodiments, this invention provides a block copolymer (BCP) encapsulated metallic or metal oxide nanoparticle wherein said block-copolymer is amphiphilic.

In some embodiments, the metallic or metal oxide nanoparticle is the core and the block copolymer is the shell of the BCP-encapsulated metallic or metal oxide nanoparticle. In some embodiments, the BCP is adhered to the surface of the nanoparticle. In some embodiments, the BCP forms a layer surrounding the nanoparticle. In some embodiments, the BCP forms micelles within which the nanoparticle resides.

Methods of the Invention

In some embodiments, this invention provides a method for target site imaging, the method comprising:
delivering a micelle comprising BCP and PAG to a target site;
irradiating or heating said micelle using radiation in the IR/near-IR range;
imaging gas bubbles released from the BCP upon heating; wherein the BCP comprising a poly(alkylene carbonate) segment (B) and a hydrophilic segment (A);

In some embodiments, heating comprises irradiating using IR/near-IR radiation. In some embodiments, heating is induced by applying a magnetic field. In some embodiments, imaging comprises ultrasound imaging. In some embodiments, imaging comprises IR imaging. In some embodiments, imaging comprises MRI. In some embodiments, imaging comprises X-ray CT.

In some embodiments, the gas bubbles are released at a temperature of from about 40° C. to about 60° C. In other embodiments, the gas bubbles are released at a temperature of from about 40° C. to about 70° C. In some embodiments, the gas bubbles are released at a temperature of from about 40° C. to about 80° C. In some embodiments, the gas bubbles are released at a temperature of from about 40° C. to about 85° C. In some embodiments, the gas bubbles are released at a temperature of from about 40° C. to about 90° C. In certain embodiments, the gas bubbles are released at a temperature of from about 40° C. to about 50° C. In some embodiments, the gas bubbles are released at a temperature of from about 50° C. to about 60° C. In some embodiments, the gas bubbles are released at a temperature of from about 50° C. to about 70° C.

In some embodiments, target site imaging, for example, tumor imaging, refers to the imaging of a target site and usually imaging of the surroundings of the site.

In another aspect, this invention provides a method for tumor targeting, the method comprising:
a) administering to a subject a composition comprising a block copolymer of the present invention; and
b) allowing the composition to reach and to adhere to a tumor.

In some embodiments, this invention provides a method of tumor imaging, the method comprising:
a) administering to a subject a composition comprising a block copolymer of the present invention;
b) allowing the composition to reach and to adhere to a tumor;
c) imaging the subject;
wherein the imaging results in an image and wherein the image exhibits the adhered composition or the location thereof, thereby indicating the location of the tumor.

In some embodiments, the imaging method is magnetic resonance imaging (MRI). In some embodiments, imaging comprises ultrasound imaging. In some embodiments, imaging comprises IR imaging. In some embodiments, imaging comprises X-ray CT.

In some embodiments, the composition is in the form of a micelle. In other embodiments, the composition is a nanoparticle comprising the block copolymer of the present invention.

These nanoparticles have significant potential as agents capable of targeting tumor cells, of rendering these tumor cells visible by means of magnetic resonance imaging (MRI), and of facilitating non-invasive thermal destruction of the tumor cells.

In some embodiments, the tumor can be in deep tissue. In some embodiments, the deep tissue is at a distance ranging from 2 cm to 4 cm, or ranging from 2 cm to 6 cm, or ranging from 1 cm to 5 cm from an external surface of the body of said subject. In another embodiment, the tumor is a non-deep tissue. For example, the methods of this invention destruct tumors in tissues below 1.0 cm depth from the surface of the skin. In another embodiment, the methods of this invention destruct tumors in tissues ranging from 0 cm to 6 cm from an external surface of the body of said subject.

As used herein, the term "tumor targeting" refers to the ability of a substance, a material, a particle, a polymer, or a micelle of the invention to identify a tumor and to adhere to a tumor. Tumor targeting refers to the selective binding or adhesion of the targeting agent to a tumor, while ideally no or little binding to non-tumor cells is observed.

The BCP-encapsulated nanoparticles of the invention provide efficient imaging agents. The BCP-encapsulated nanoparticles of the invention can be used for targeted MRI/hyperthermia theranosis (i.e., therapy and diagnosis). The BCP-encapsulated nanoparticles of the invention can efficiently function as whole body MRI contrast agents. The BCP-encapsulated nanoparticles of the invention can be used as contrast agents for MRI of specific organs. The BCP-encapsulated nanoparticles of the invention can be effective theranosis agents enabling non-invasive MRI identification and hyperthermia treatment of tumors.

Processes of the Invention

In some embodiments, this invention provides a method of preparing poly(poly(ethylene glycol) methyl ether methacrylate)-poly(propylene carbonate)-poly(poly(ethylene glycol) methyl ether methacrylate) (PPEGMA-PPC-PPEGMA) triblock copolymers. In some embodiments, the tri-block copolymer is synthesized by Reversible Addition-Fragmentation Chain-Transfer (RAFT) polymerization of methacrylate-type PPEGMA monomers using dihydroxyl end-functional PPC as the starting material. In some embodiments, the di-block copolymer is synthesized by Reversible Addition-Fragmentation Chain-Transfer (RAFT) polymerization of methacrylate-type PPEGMA monomers using monohydroxyl end-functional PPC as the starting material. In some embodiments, other PPC-based amphiphilic block copolymers are synthesized similarly by RAFT. In another embodiment, instead of RAFT, the Atom Transfer Radical Polymerization (ATRP) technique, or any suitable variation of the "Controlled/Living Radical Polymerization" method, is used for the syntheses of these block copolymers. These PPC-based block copolymer surfactants can be used for a wide variety of other industrial and technological applications, including their uses as drug encapsulants, surfactants, emulsifiers, detergents, wetting/foaming agents, viscosity modification agents, dispersants, etc. In some embodiments, the tri-block copolymer is prepared according to the procedures described in example 1. A synthesis scheme is shown in FIG. 1.

This invention demonstrates that the thermal degradation temperature of poly(propylene carbonate) (PPC) is reduced down to the biomedically relevant temperature range (i.e., 40-60° C.) by using a photoacid generator (PAG 290) as the catalyst for activating the random scission reaction of PPC in an aqueous environment. Specifically, this invention was demonstrated by confirming the generation of $CO_2$ in water by thermal degradation of the micelles formed by PPC-based amphiphilic block copolymers (namely, poly(poly(ethylene glycol) methyl ether methacrylate)-poly(propylene carbonate)-poly(poly(ethylene glycol) methyl ether methacrylate) or PPEGMA-PPC-PPEGMA triblock polymers) at desired low temperatures (<60° C.) under the influence of the micelle-encapsulated PAG 290. These results demonstrate the potential utility of PPC as a $CO_2$-generating agent in ultrasound imaging applications.

It is one object of the present invention that a photo-acid generator (PAG) is used for lowering the $CO_2$-generation temperature of polypropylene carbonate (PPC) in aqueous environments. Water compatible micelles and particles comprising PPC are designed to be soluble and stable in aqueous solutions. The structures are constructed with PAG that is included in the PPC. Such micelles/particles are biocompatible and can be used for biomedical applications. The PPC structures are designed such that the photo-generated acid does not significantly diffuse into the aqueous phase. This concept was tested as described herein by investigating the thermal degradation behavior of a bulk PPC material immersed in water, and of micelles formed in water by PPC-based amphiphilic block copolymers at desired low temperatures (<60° C.) under the influence of added PAG. Thus, it is another aspect of the present invention to demonstrate that the thermal degradation temperature of PPC can be reduced down to a biomedical relevant temperature range (i.e. 40-60° C.) in an aqueous environment. This property enables the use of PPC for cancer ultrasound imaging and for other medical applications.

Further, the influence of transition metal addition on the decomposition temperature of PPC was investigated by placing the polymer in contact with a surface of the transition metal (e.g. cobalt) both in the presence and in the absence of PAG.

The following examples are presented in order to more fully illustrate the preferred embodiments of the invention. They should in no way be construed, however, as limiting the broad scope of the invention.

EXAMPLES

Materials and Methods
Samples

Figure 2:
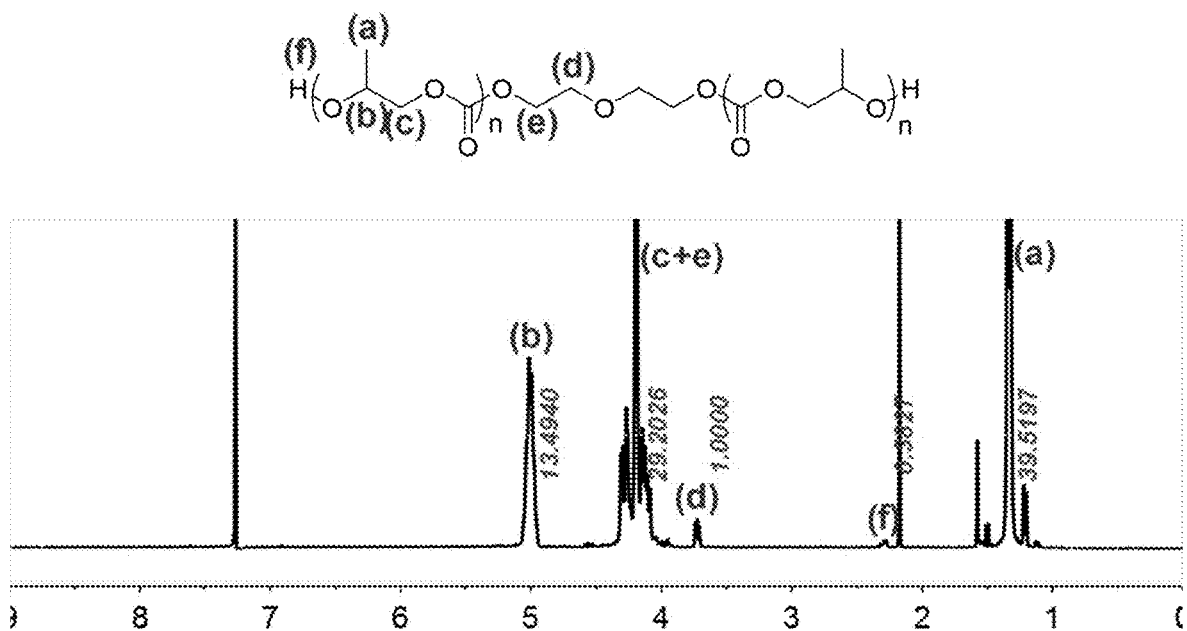
FIG. 2 depicts $^1$H NMR spectra of the dihydroxyl-terminated PPC homopolymer material (in $CDCl_3$).
Figure 3:
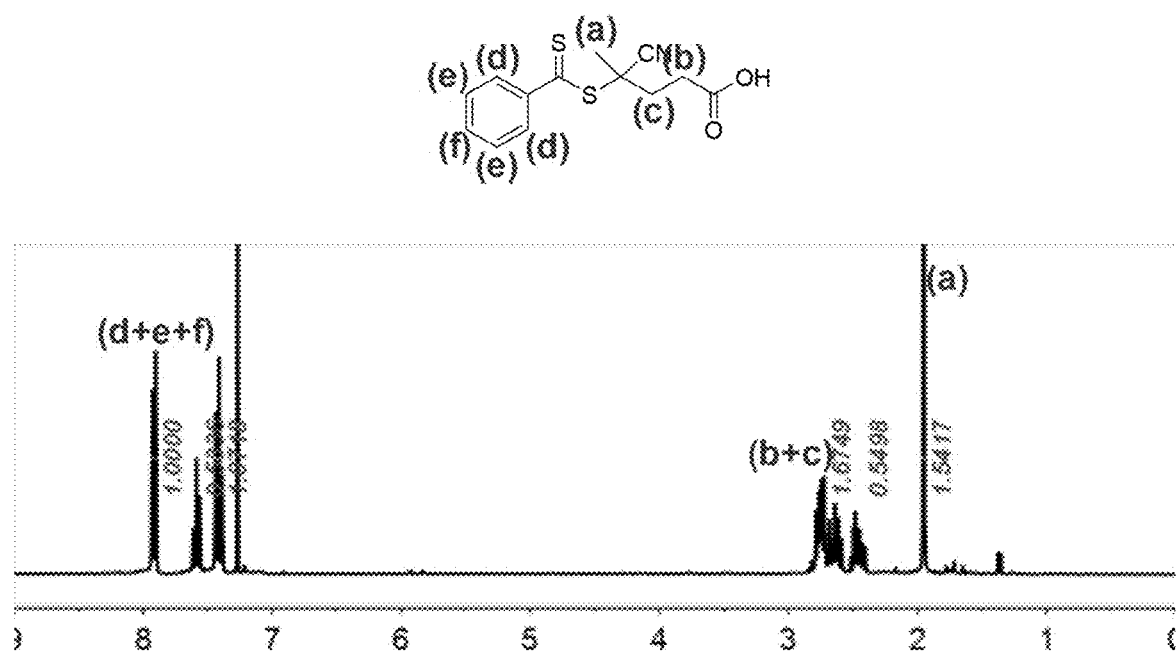
FIG. 3 depicts $^1$HNMR spectra of 4-cyano-4-(phenylcarbonothioylthio)pentanoic acid (CPCP) in $CDCl_3$.
Figure 7:
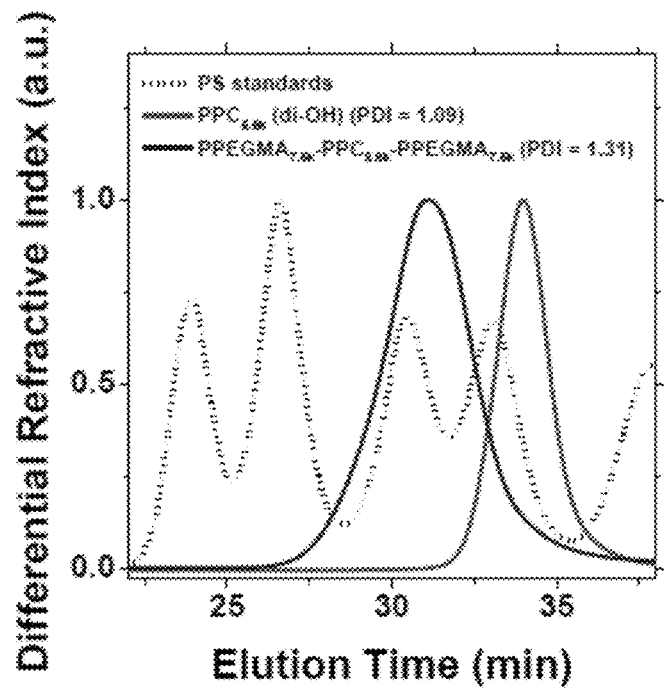
FIG. 7 depicts GPC traces for the dihydroxyl PPC homopolymer (PDI=1.09) and the PPEGMA-PPC-PPEGMA tri-block copolymer (PDI=1.31). Also shown for comparison are the GPC traces for polystyrene (PS) standards.

Several mono- and dihydroxyl-ended PPC homopolymers having different molecular weights (i.e., approximately, 2, 5, and 10 kg/mol) were provided by SK Innovation. These polymers were synthesized by chemists at SK Innovation via cobalt-salen-catalyzed copolymerization of $CO_2$ and propylene oxide using a published procedure. The molecular characteristics of these polymers were all re-characterized by proton nuclear magnetic resonance spectroscopy ($^1$H NMR) and gel permeation chromatography (GPC). The specific PPC material used in the present example was a dihydroxy PPC, and this polymer was determined to have a number-average molecular weight ($M_n$) of 5.6 kg/mol (by NMR in $CDCl_3$) and a polydispersity index (PDI) of 1.09 (by GPC with tetrahydrofuran (THF) mobile phase based on polystyrene standards). The NMR and GPC data for this polymer are shown in FIGS. 2 and 7.

The photoacid generator (PAG) material used in the examples was tris([4-([4-acetylphenyl]sulfanyl)phenyl])sulfanium tetrakis(pentafluorophenyl)borate (Irgacure® PAG 290, 96% purity, BASF); this material will be denoted as "PAG 290" herein.

Thermogravimetric analysis (TGA) samples were typically prepared by solvent casting. For instance, for preparation of PPC/cobalt composite samples, PPC was first dissolved in either y-butyrolactone (GBL, >99% purity, Sigma-Aldrich) or N,N-dimethylformamide (DMF, >99.8% purity, Sigma-Aldrich) to a concentration of 2.5 grams of PPC per milliliters of GBL (or DMF), and subsequently a required amount of cobalt powder (2 μm diameter, 99.8% purity, Sigma-Aldrich) was added to it. This mixture was then homogenized by vigorous stirring, dispensed onto a glass plate, and dried under vacuum at 60° C. overnight. The resulting PPC/cobalt film was carefully removed from the glass substrate and used for thermal degradation experiment.

To prepare PPC/PAG 290 mixtures, PPC and PAG 290 were first co-dissolved, typically at a weight ratio of 96 parts of PPC to 4 parts of PAG 290, in either GBL or DMF to a final PPC concentration of 2.5 grams of PPC per milliliter of GBL. The polymer solution was then placed on a glass slide and dried under vacuum at 60° C. overnight. For photoacid generation, the dried PPC/PAG 290 sample was exposed to UV light (typically for 60 minutes) using a UVP's B-100AP lamp (wavelength=365 nm, power density=20 mW/cm$^2$) mounted on an illumination environmental chamber designed in our laboratory for homogeneous illumination and efficient heat dissipation. The UV-exposed PPC/PAG 290 sample was carefully collected from the glass substrate and used for thermal degradation experiment.

Thermogravimetric Analysis (TGA)

TGA measurements were performed using a TA Instruments Q-500 Thermogravimetric Analyzer. During measurements, both the sample and balance areas were continuously purged with nitrogen at a flow rate of 50 ml/min. Samples were loaded in aluminum pans under nitrogen environment.

Visualization of Gas Formation

PPC (1.00 g) and PAG 290 (41.7 mg) were first mixed in GBL (0.40 ml). This polymer solution was then placed in a glass vial and dried under vacuum at 60° C. for 24 hours. For photoacid generation, the dried PPC/PAG 290 mixture was exposed to UV light (365 nm, 20 mW/cm$^2$, 60 minutes). About 7.0 ml of deionized water was added to the vial containing about 1.0 g of the UV-exposed PPC/PAG 290 mixture. Then, the vial was tightly capped and heated in an oil bath at 80° C. Photographs of the sample were taken at various time points.

Example 1

PPEGMA-PPC-PPEGMA Triblock Copolymer Synthesis

Poly(poly(ethylene glycol) methyl ether methacrylate)-poly(propylene carbonate)-poly(poly(ethylene glycol) methyl ether methacrylate) (PPEGMA-PPC-PPEGMA) triblock copolymers were synthesized by Reversible Addition-Fragmentation Chain-Transfer (RAFT) polymerization of PEGMA using dihydroxyl PPC ($M_n$=5.6 kg/mol) as the starting material, as schematically described in FIG. 1.

The first step of this process was to convert the OH ends of the dihydroxyl PPC to dithioester ends via esterification with 4-cyano-4-(phenylcarbonothioylthio)pentanoic acid (CPCP, >97% purity, Sigma-Aldrich) in anhydrous dichloromethane solvent (DCM, >99.8% purity, Sigma-Aldrich) under the catalytic influence of 4-dimethylaminopyridine (DMAP, >99% purity, Sigma-Aldrich) and N,N-dicyclohexylcarbodiimide (DCC, 99% purity, Sigma-Aldrich). Briefly, the dihydroxyl PPC (3.0 g, 0.55 mmol) and DCC (0.45 g, 2.2 mmol) were dissolved in anhydrous DCM (10 ml) in a round-bottom flask.

In a separate flask, CPCP (0.62 g, 2.2 mmol) and DMAP (54 mg, 0.44 mmol) were dissolved in anhydrous DCM (5 mL). The solution containing CPCP and DMAP (red colored) was added dropwise to the solution containing PPC and DCC at 0° C. The reaction mixture was then allowed to warm to room temperature over an hour, and the reaction was allowed to proceed for 24 hours. Afterwards, insoluble 1,3-dicyclohexylurea was removed by filtration. The CPCP-PPC-CPCP product was further purified by twice precipitation into ice-cold diethyl ether (~500 mL), and then dried under vacuum at room temperature for 48 hours.

The CPCP-PPC-CPCP material was used as the macro-initiator for the RAFT polymerization of the poly(ethylene glycol) methyl ether methacrylate monomer ($M_n$=500 g/mol, Sigma-Aldrich). This RAFT reaction was conducted in anhydrous THF solvent (>99.9% purity, Sigma-Aldrich) using 2,2'-azobis(2-methylpropionitrile) (AIBN, 99% purity, Sigma-Aldrich) as the primary radical source. Briefly, CPCP-PPC-CPCP (0.5 g, 8.3×10$^{2-}$ mmol), PEGMA (2.0 g, 3.0 mmol), AIBN (1.35 mg, 8.3×10$^{3-}$ mmol) and anhydrous THF (1.5 mL) were charged to a round-bottom flask. After purging with nitrogen at room temperature for 30 minutes under vigorous stirring, the reactor was heated to 70° C., and the polymerization was performed at that temperature for 24 hours. Afterwards, the polymerization mixture was quenched by placing the flask in an ice water bath and exposed to air for the termination of the reaction. Then, the polymer product was precipitated in ice-cold ether, which removed unreacted PEGMA from the block copolymer product. The resulting block copolymer product was dried in a vacuum oven at 40° C. overnight.

Micelle Solution Preparation

PPEGMA-PPC-PPEGMA micelles were prepared using the solvent exchange method as follows. PPEGMA-PPC-PPEGMA and PAG 290 were co-dissolved at a weight ratio of 92 percent PPC and 8 percent PAG 290 in either GBL or DMF to a PPC concentration of 10 mg/ml. This solution was loaded into a membrane dialysis tube (50 kg/mol molecular weight cutoff, SpectraPor). The solution was dialyzed against a large volume (~1 liter) of deionized water. The water was replaced with fresh water five times during a total 48-hour period. After the dialysis step, the final PPC concentration of the solution was adjusted to 5 mg/ml by adding an additional amount of deionized water.

Gas Chromatography/mass Spectroscopy (GC/MS)

GC-MS measurements were performed using an Agilent Technologies Headspace System (HSS) GC/MS Analyzer with a DB-5 ms Capillary HPLC Column (60 m length×0.32 mm inner diameter×0.25 m thickness). The injector temperature was set at 280° C. The oven temperature was programmed to increase from 40 to 200° C. at a rate of 20° C./min and hold at 200° C. for 5 minutes.

Example 2

Justification of the Approach to Lowering the PPC Degradation Temperature

Figure 17:
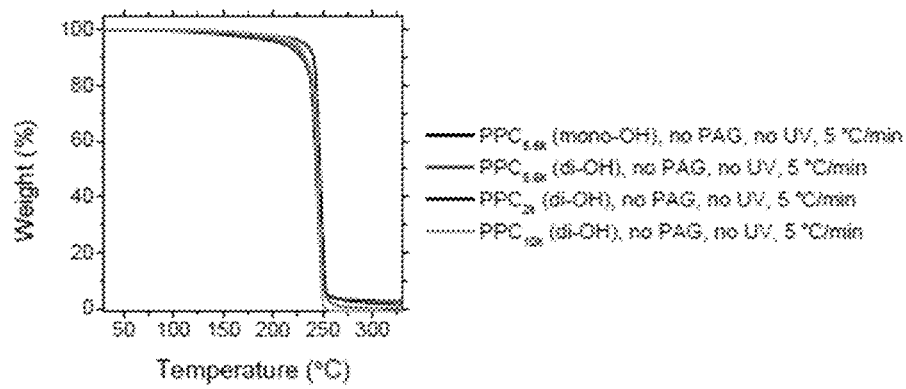
FIG. 17 depicts thermogravimetric analysis (TGA) weight loss profiles of a monohydroxyl PPC having a number-average molecular weight of 5.6 kg/mol, a dihydroxyl PPC having a number-average molecular weight of 5.6 kg/mol, a dihydroxyl PPC having a number-average molecular weight of 2.0 kg/mol, and a dihydroxyl PPC having a number-average molecular weight of 10.0 kg/mol. The TGA measurements were performed under continuous heating at a rate of 5° C./min in nitrogen environment.

PPC is an alternating copolymer of $CO_2$ and propylene oxide. PPC samples were prepared by a copolymerization reaction between $CO_2$ and propylene oxide catalyzed by a cobalt-salen catalyst using either a mono- or dihydroxyl compound as an initiator. The chemical structure of a PPC polymer synthesized using a di-initiator, diethylene glycol, is presented in FIG. 16(A); the $^1$H-NMR spectra are shown in FIG. 2. It has been suggested that the thermal decomposition of PPC can occur by two different mechanisms; at high temperatures (200-300° C.), the chains are believed to degrade mainly by random scission processes, leading to production of $CO_2$, whereas the degradation at lower temperatures involves more of a backbiting reaction with subsequent unzipping of the chain, which produces cyclic propylene carbonate (having an atmospheric boiling temperature of about 240° C.) as a main product (but not $CO_2$). Because the hydroxyl chain end group plays a role in the backbiting reaction, the degradation of hydroxyl end-capped PPC is known to be, in general, dependent upon the molecular weight of the polymer; a lower molecular weight PPC contains a higher amount of OH and thus degrades faster. However, as shown in FIG. 17, the TGA measurements did not detect any significant influence of molecular weight (in the range of 2 to 10 kg/mol) or OH end functional groups (i.e., mono- vs. dihydroxyl) on PPC degradation temperature. In the following, discussion will focus on the results obtained from the dihydroxyl PPC sample having a number-average molecular weight of 5.6 kg/mol (denoted as "PPC5.6k (di-OH)").

Figure 8:
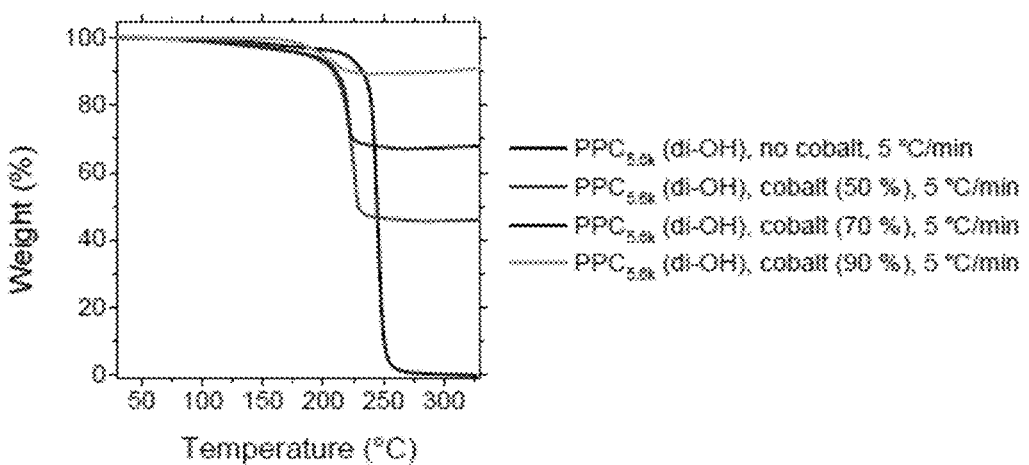
FIG. 8 depicts constant-heating TGA weight loss profiles of pure PPC, PPC containing 50 wt. % cobalt powder, PPC containing 70 wt. % cobalt powder, and PPC containing 90 wt. % cobalt powder. The TGA measurements were performed under nitrogen purging conditions at a heating rate of 5° C./min.

Two methods were tested for lowering the thermal decomposition temperature of PPC. The first was to expose PPC to the surface of a transition metal such as cobalt. The logic was that the activation energy of the decomposition reaction might become significantly reduced in the presence of a transition metal, given that the metal also lowers the activation energy of the original polymerization reaction. To evaluate the feasibility of this approach, TGA measurements were performed on PPC/cobalt composites with varying compositions (i.e., containing 0, 50, 70 and 90% by weight of cobalt). The samples were prepared by casting a homogenized solution containing specific amounts of PPC and cobalt powder in GBL on a glass substrate and drying it under vacuum (at 60° C. for 24 hours). As shown in FIG. 8, the effect of cobalt was found to be mediocre; even at the highest loading of 90%, cobalt is able to lower the PPC degradation temperature by only about 40° C. (based on the temperatures at 50% PPC weight loss). Since the amount of the effect of cobalt was not sufficient, an alternative approach of using photoacid generator (PAG) materials was employed (as discussed in the next subsection).

Example 3

PPC Degradation Parameters

Figure 18:
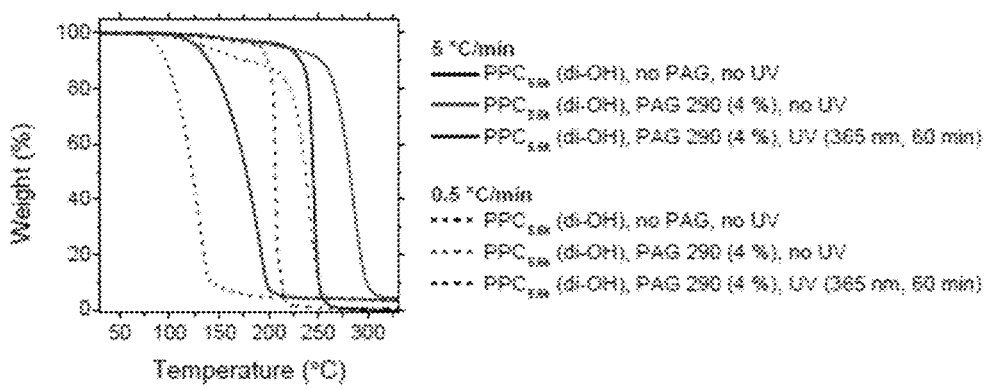
FIG. 18 depicts constant-heating TGA weight loss profiles of pure PPC, the UV-unexposed PPC containing 4 wt. % PAG 290, and the UV-exposed PPC containing 4 wt. % PAG 290. UV irradiation was performed using a 365 nm lamp (power density=20 mW/cm$^2$) for a duration of 60 minutes. The TGA measurements were performed under nitrogen purging conditions at two different heating rates (5 and 0.5° C./min).

Initially, four candidate PAG materials were chosen for testing: tris(4-tert-butylphenyl)sulfonium perfluoro-1-butanesulfonate from Sigma-Aldrich, BASF Irgacure PAG 290, BASF GSID26-1, and BASF CGI 1907. Among these, the Irgacure PAG 290 material was found to be most effective in lowering the degradation temperature of PPC (data not shown). Therefore, all subsequent studies reported in this investigation were performed with this specific PAG material; hereafter, this compound will be denoted as "PAG 290". PAG 290 is a salt between a sulfonium cation and a tetraphenyl borate anion, and its exact chemical structure is displayed in FIG. 16(B). Typically, PPC/PAG 290 mixtures were prepared by casting a solution containing PPC and PAG 290 (at a weight ratio of 96:4) in GBL onto a glass plate and drying it under vacuum (at 60° C. for 24 hours). Also, in a typical experiment, acids were generated within the polymer matrix by exposing the material to 365 nm UV radiation for 60 minutes using a UV illumination setup described in a previous publication; this photoacid generation process accompanied a change in sample color from transparent to orange. As can be seen from the TGA data presented in FIG. 18, without UV irradiation, added PAG 290 itself, in fact, caused a significant increase of PPC degradation temperature, i.e., by more than 30 degrees. However, the acids generated by UV irradiation of PAG 290 were indeed found to significantly decrease the degradation temperature of PPC; at a heating rate of 5° C./min, the temperature at 50% weight loss of PPC was seen to be reduced by 67° C. (i.e., from 244° C. for the pristine PPC to 177° C. for the polymer with added PAG 290 after UV exposure), and at a reduced heating rate of 0.5° C./min, the change was even greater (the half decomposition temperature changed from 206 to 123° C. after treatments with PAG 290 and UV irradiation). The heating rate dependent degradation behavior of PPC has also previously been reported by other investigators. Also, it is noted that in the absence of added PAG 290, exposure of PPC to UV radiation did not produce any change in the thermal degradation profile of the polymer from the unexposed situation. What is most remarkable is that under the influence of the UV-activated PAG 290, the PPC was seen to start decomposing at temperatures close to about 70° C. when it was heated at a slow rate of 0.5° C./min, which supports that the thermal degradation temperature of PPC can indeed be reduced down to a range relevant to its clinical use by using PAG 290 as the catalyst for activating the decomposition reaction of PPC.

Figure 9:
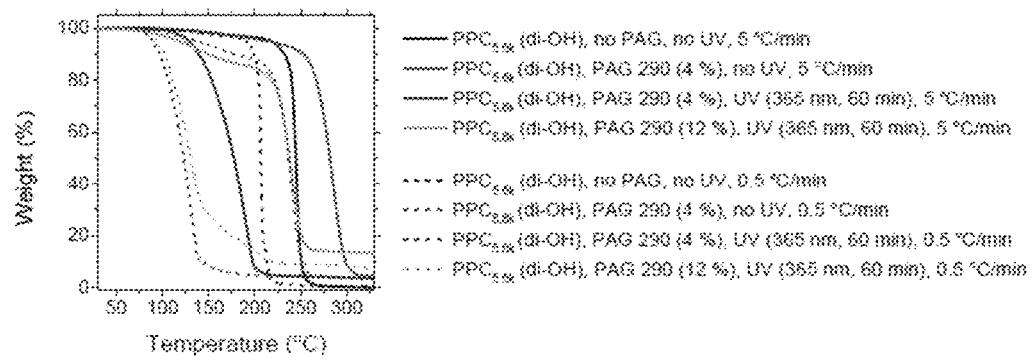
FIG. 9 depicts constant-heating TGA weight loss profiles of pure PPC, the UV-unexposed PPC containing 4 wt. % PAG 290, the UV-exposed PPC containing 4 wt. % PAG 290, and the UV-exposed PPC containing 12 wt. % PAG 290. UV irradiation was performed using a 365 nm lamp (power density=20 mW/cm$^2$) for a duration of 60 minutes. The TGA measurements were performed under nitrogen purging conditions at two different heating rates (5 and 0.5° C./min).
Figure 10:
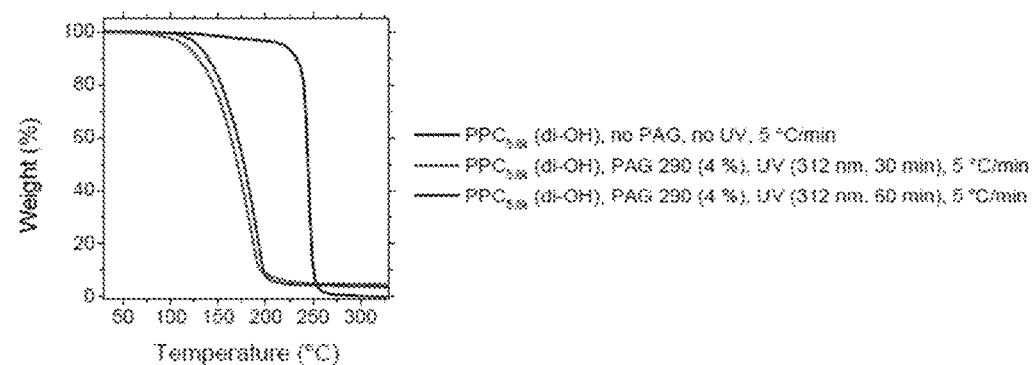
FIG. 10 depicts constant-heating TGA weight loss profiles of pure PPC, the 30-minute-UV-exposed PPC containing 4 wt. % PAG 290, and the 60-minute-UV-exposed PPC containing 4 wt. % PAG 290. UV irradiation was performed using a 312 nm wavelength lamp. The TGA measurements were performed under nitrogen purging conditions at a heating rate of 5° C./min.
Figure 11:
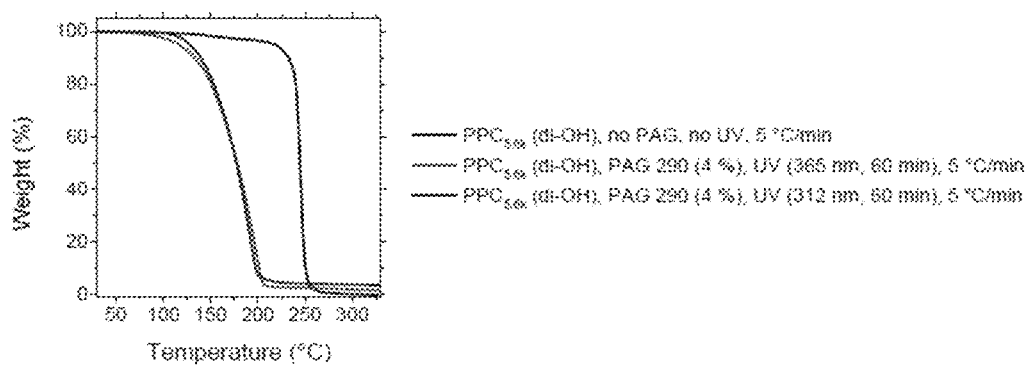
FIG. 11 depicts constant-heating TGA weight loss profiles of pure PPC, and two different UV-exposed PPC samples containing 4 wt. % PAG 290. UV irradiation was performed using two different wavelengths (365 and 312 nm) for the same duration of time (60 minutes). The TGA measurements were performed under nitrogen purging conditions at a heating rate of 5° C./min.

As shown in FIG. 9, increasing the PAG 290 concentration from 4 to 12% (by weight) increased the half degradation temperature of PPC. This is perhaps an indication that at the higher PAG 290 concentration the PPC/PAG 290 mixture becomes phase-separated, resulting in an inhomogeneous distribution of the PAG compounds; this speculation is supported by the observation that the PPC/PAG 290 mixture became turbid when the PAG 290 concentration was increased; note that even the PPC/PAG 290 sample containing 4% PAG 290 is typically slightly translucent. It was also found that the UV irradiation time (30 vs. 60 minutes) or wavelength (365 vs. 312 nm) does not influence the degradation temperature of PPC (FIGS. 10 and 11).

Figure 19:
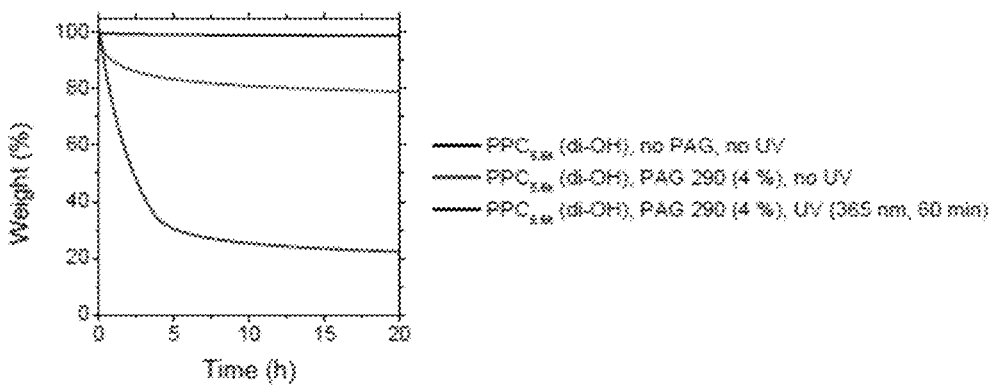
FIG. 19 depicts isothermal TGA weight loss profiles of pure PPC, the UV-unexposed PPC containing 4 wt. % PAG 290, and the UV-exposed PPC containing 4 wt. % PAG 290. UV irradiation was performed using a 365 nm lamp (power density=20 mW/cm$^2$) for a duration of 60 minutes. The TGA measurements were performed under nitrogen purging conditions at a constant temperature of 80° C.

In order to demonstrate the generation of $CO_2$ by thermal degradation of PPC at desired low temperatures, the weight of the UV-exposed PPC/PAG 290 mixture was measured over time at a constant temperature of 80° C. As shown in FIG. 19, the 50% decomposition time of the UV-exposed PPC/PAG 290 sample was 2.5 hours, whereas the pristine PPC material did not show any loss of weight over the 20 hour measurement period. The UV-unexposed PPC/PAG 290 control was found to have lost about 20% of its original weight after 20 hours of incubation at 80° C.

Figure 20:
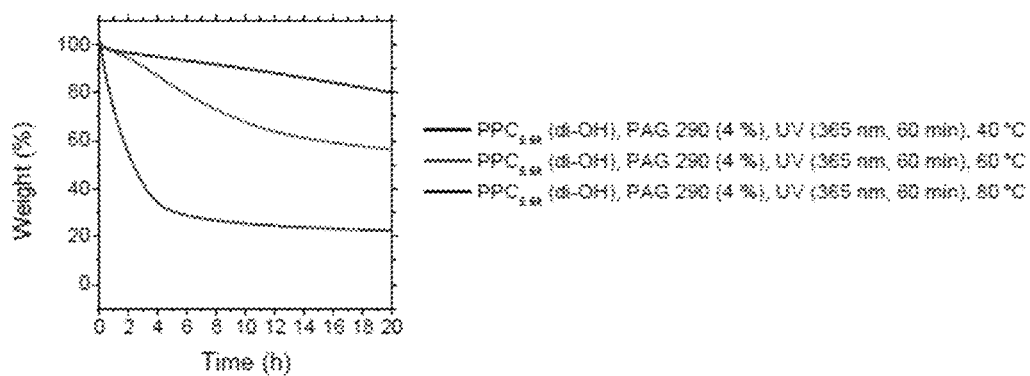
FIG. 20 depicts isothermal TGA weight loss profiles of the UV-exposed PPC containing 4 wt. % PAG 290 obtained at three different temperature conditions, 40, 60, and 80° C. UV irradiation was performed using a 365 nm lamp (power density=20 mW/cm$^2$) for a duration of 60 minutes. The TGA measurements were performed under nitrogen purging conditions.

Similar tests were also performed at lower temperatures (60 and 40° C.). As shown in FIG. 20, the UV-activated PPC/PAG 290 sample exhibited 40 and 20 percent loss of weight after 20 hours of heating at these low temperatures, i.e., 60 and 40° C., respectively, suggesting that the $CO_2$ generation from PPC is indeed possible at temperatures even close to the body's normal temperature by using a photoacid generator such as PAG 290. It should also be noted that the PPC weight loss observed at these low-temperature conditions clearly indicates that the thermal decomposition of PPC in the presence of the UV-activated PAG 290 occurs by the random scission reaction and thus produces CO2, because the other type of degradation reaction (i.e., the backbiting mechanism) would have produced a non-volatile compound, cyclic propylene carbonate, as the main reaction product.

Figure 12:
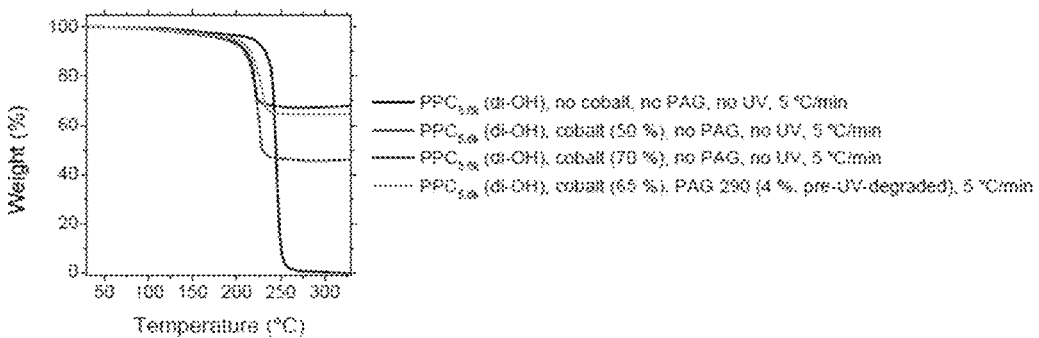
FIG. 12 depicts constant-heating TGA weight loss profiles of pure PPC, PPC containing 50 wt. % cobalt power, PPC containing 70 wt. % cobalt powder, and PPC containing 65 wt. % cobalt power and 4 wt. % pre-UV-exposed PAG 290. UV irradiation was performed using a 365 nm lamp (power density=20 mW/cm$^2$) for a duration of 60 minutes. The TGA measurements were performed under nitrogen purging conditions at a heating rate of 5° C./min.
Figure 13:
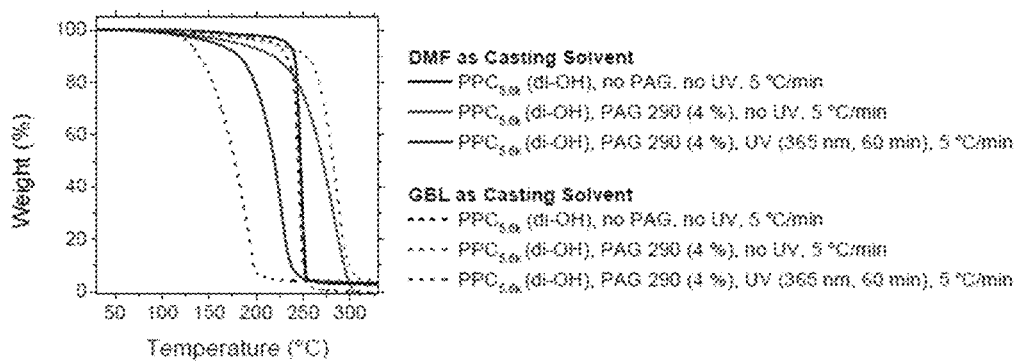
FIG. 13 depicts constant-heating TGA weight loss profiles of pure PPC, the UV-unexposed PPC containing 4 wt. % PAG 290, and the UV-exposed PPC containing 4 wt. % PAG 290. The PPC/PAG 290 mixtures were prepared by solvent exchange using either (A) GBL or (B) DMF as the initial co-dissolution solvent. UV irradiation was performed using a 365 nm lamp (power density=20 mW/cm$^2$) for a duration of 60 minutes. The TGA measurements were performed under nitrogen purging conditions at a heating rate of 5° C./min.
Figure 14:
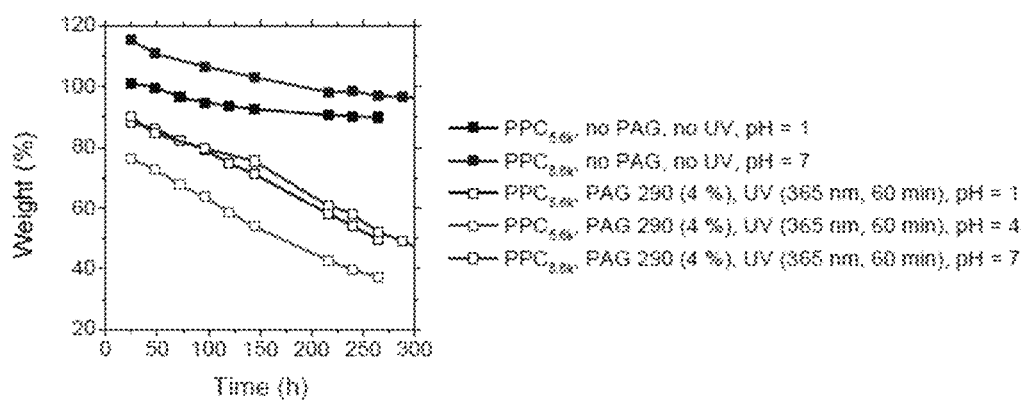
FIG. 14 depicts weights of the pure PPC control and the UV-unexposed and UV-exposed PPC/PAG 290 mixtures measured during drying after 20 hours of heating at 80° C. in water under several different pH conditions (pH 1, pH 4, and pH 7). UV irradiation was performed using a 365 nm lamp (power density=20 mW/cm$^2$) for a duration of 60 minutes. The drying was performed in a vacuum oven at room temperature. The x-axis represents drying time.

Further, it was tested whether the combined use of PAG 290 and cobalt powder would further lower the $CO_2$ generation temperature of PPC. It was found that the addition of the UV-activated PAG 290 to the PPC/cobalt composite does not affect the degradation temperature of PPC relative to the PPC/cobalt composite with no added PAG 290 (FIG. 12). It was suspected that the acid compound generated from PAG 290 has an affinity to cobalt; the acid molecules perhaps adsorb to the surface of cobalt particles, and in such situation, both components will lose their catalytic function.

The TGA data presented to this point were obtained from samples prepared using GBL as the casting solvent. In order to examine whether the choice of casting solvent affects the thermal degradation properties of the PPC/PAG 290 mixtures, the same tests were repeated for a different casting solvent, DMF. Figure S13 displays the results. In the pure PPC situation, the choice of casting solvent (between GBL vs. DMF) seems to have no significant effect on the TGA profile; this result also suggests that there is no significant amount of residual solvent present in the solvent-cast sample, because otherwise the two different solvents would have produced clearly different alterations in the TGA weight-loss pattern (note that at atmospheric pressure, GBL boils at 204° C., while DMF at 153° C., plenty of separation from GBL). However, when the casting solvent is changed from GBL to DMF, the 50 percent weight loss temperature of the UV-unexposed PPC/PAG 290 mixture decreased from 282 to 271° C., whereas the 50 percent loss temperature of the UV-activated PPC/PAG 290 mixture increased from 177 to 219° C.; that is, the effect of PAG 290 becomes diminished when DMF is used as the casting solvent. It is suspected that when cast using DMF, the PPC and PAG 290 mixture becomes less uniformly mixed. Unless noted otherwise, all experiments reported were performed using GBL as the casting solvent.

Example 4

Degradation of PPC in Water

Figure 21:
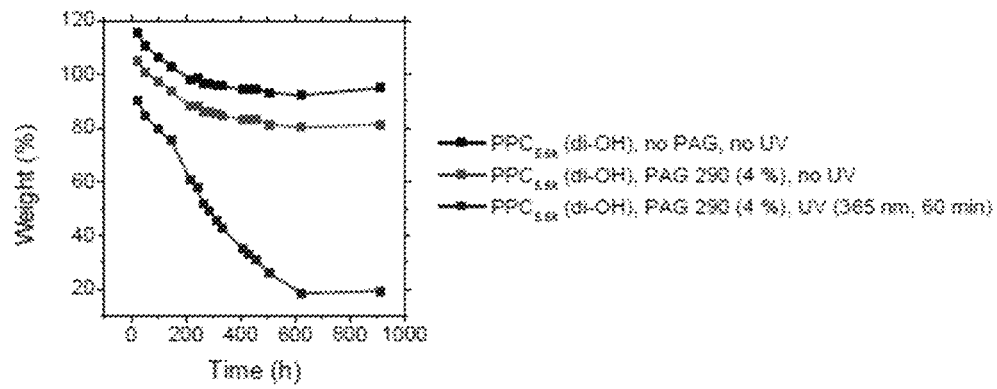
FIG. 21 depicts weights of the pure PPC control and the UV-unexposed and UV-exposed PPC/PAG 290 mixtures measured during drying after 20 hours of heating at 80° C. in water. UV irradiation was performed using a 365 nm lamp (power density=20 mW/cm$^2$) for a duration of 60 minutes. The drying was performed in a vacuum oven at room temperature. The x-axis represents drying time.

PPC degradation data obtained under dried conditions have been discussed herein above. In order to confirm that the degradation temperature of PPC can be similarly reduced in an aqueous environment by using PAG 290, the same set of samples (i.e., the UV-exposed and UV-unexposed PPC/PAG 290 mixtures, and the pure PPC control) were first heated in water at 80° C. for 20 hours, and then dried under vacuum at room temperature, and over the course of drying, the weights of these samples were recorded as a function of time. The resulting sample weight vs. drying time data are graphed in FIG. 21. As shown in the figure, in general it took about 600 hours (i.e., 25 days) to completely remove volatile mass from the initially wet samples; it is believed that the volatile component is just water, because the non-degraded pure PPC control that recovered about 92% of its original weight after 25 days of drying also showed almost the same time scale for drying as those other degraded PPC/PAG 290 mixture samples. After 25 days of drying, the UV-exposed PPC/PAG 290 mixture showed about 80% weight loss, and the UV-unexposed PPC/PAG 290 mixture also showed about 20% weight loss. These results are exactly in agreement with the TGA measurements performed under dried conditions (FIG. 19), suggesting that PAG 290 indeed also works in aqueous solution.

Figure 22:
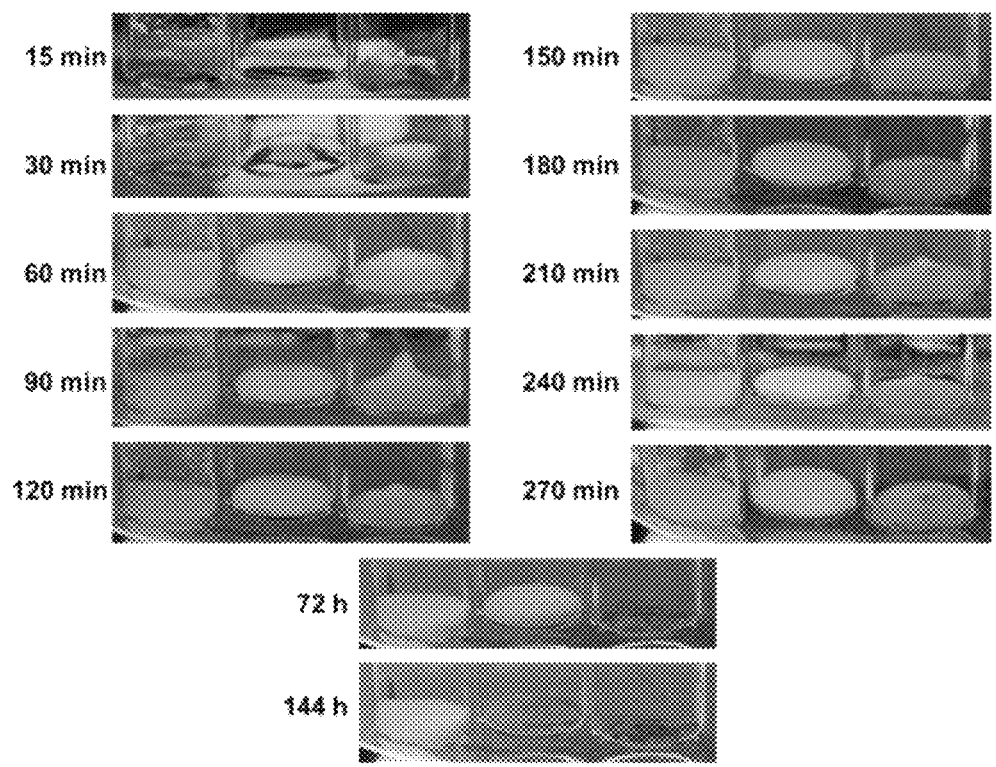
FIG. 22 depicts time-series photographs of one gram samples of pure PPC (left), the UV-unexposed PPC containing 4 wt. % PAG 290 (middle), and the UV-exposed PPC containing 4 wt. % PAG 290 (right) placed in water at 80° C. UV irradiation was performed using a 365 nm lamp (power density=20 mW/cm$^2$) for a duration of 60 minutes.
Figure 23:
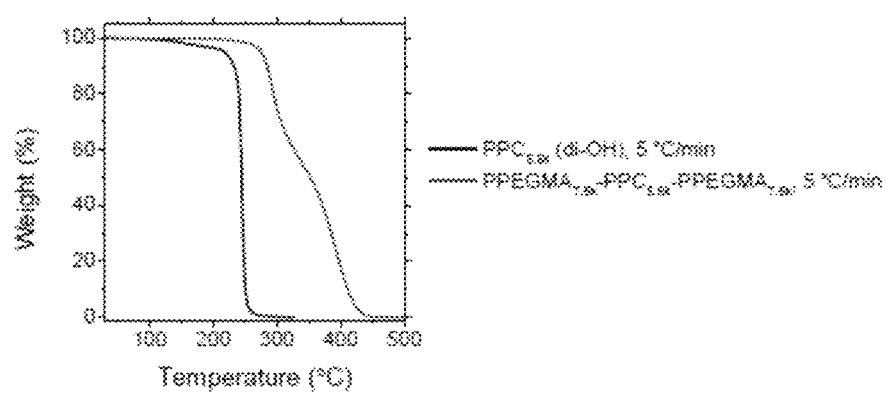
FIG. 23 depicts constant-heating TGA weight loss profiles of the dihydroxyl PPC homopolymer and the PPEGMA-PPC-PPEGMA triblock polymer. The measurements were performed under nitrogen purging conditions at a heating rate of 5° C./min.
Figure 25:
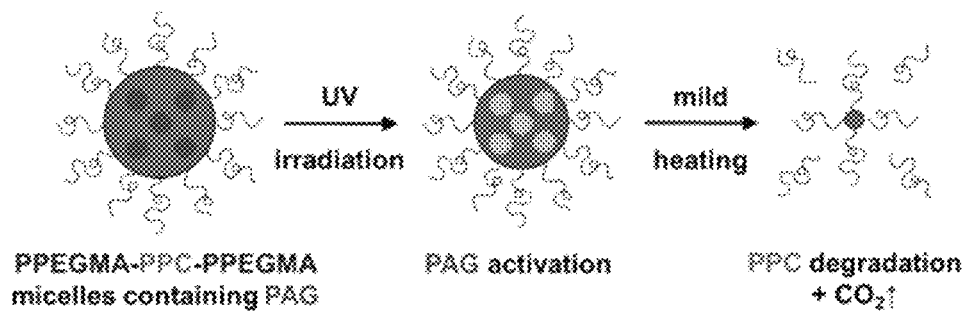
FIG. 25 depicts the scheme of $CO_2$-producing polymer micelles.
Figure 26:
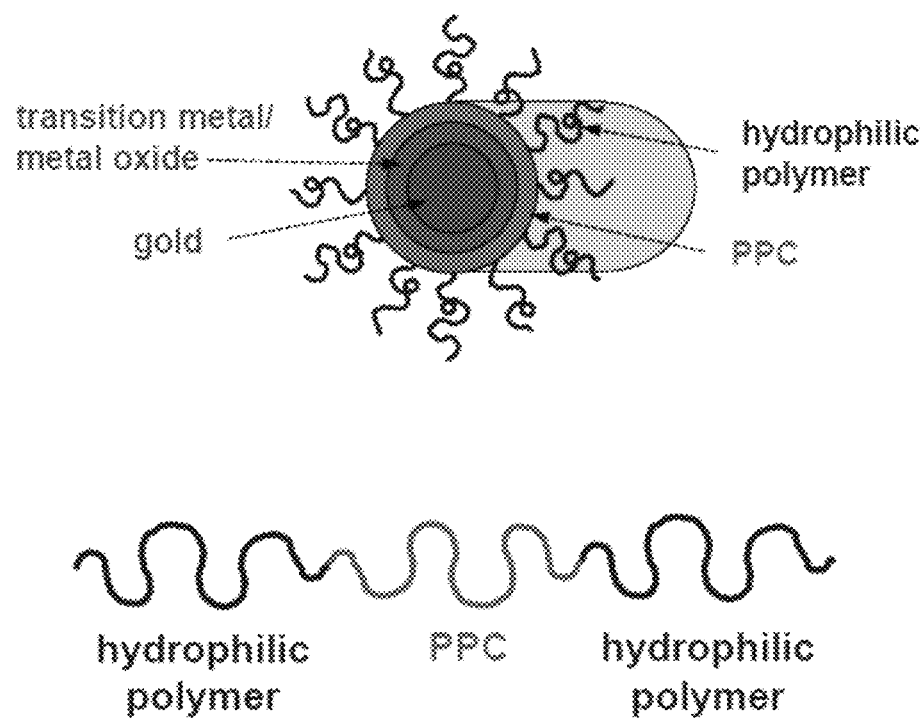
FIG. 26 demonstrates the biomedical applications of PPC, e.g., for cancer imaging/treatment: Lower the degradation temperature; and develop PPC-based amphiphilic block copolymers that are water-dispersible.
Figure 29:
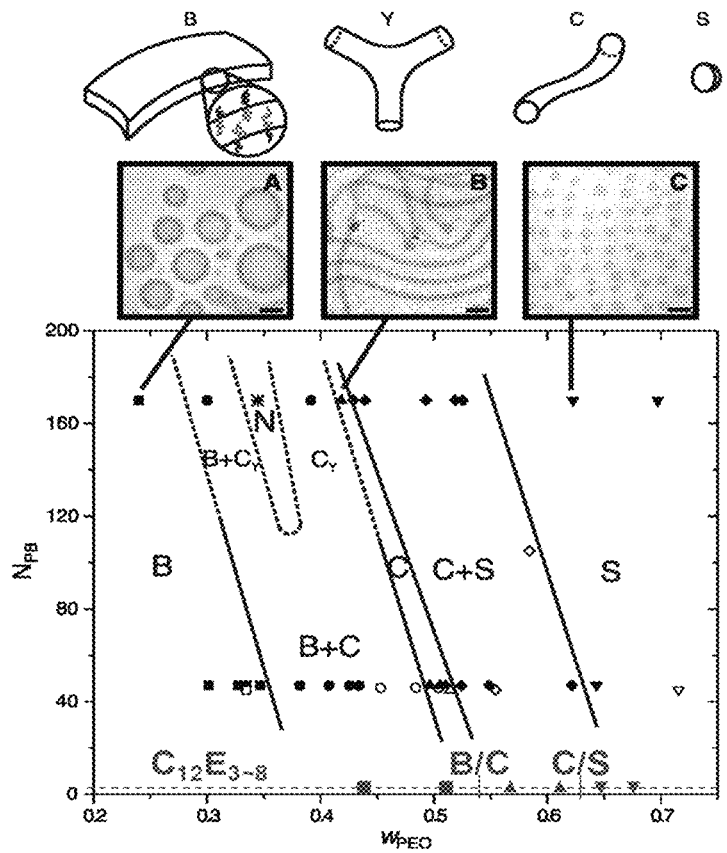
FIG. 29 shows micelle geometry vs. molecular composition
Figure 30:
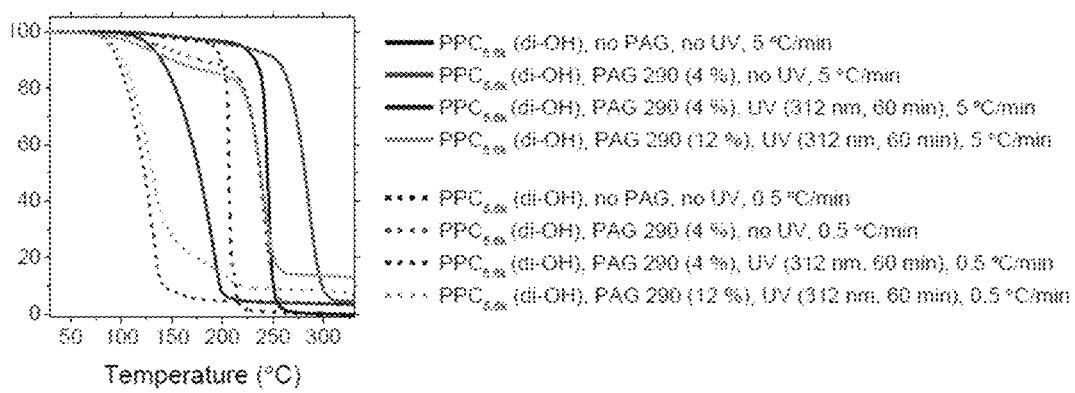
FIG. 30 shows the effect of PAG concentration on thermal degradation of PPC, 4 wt % vs. 12 wt %
Figure 31:
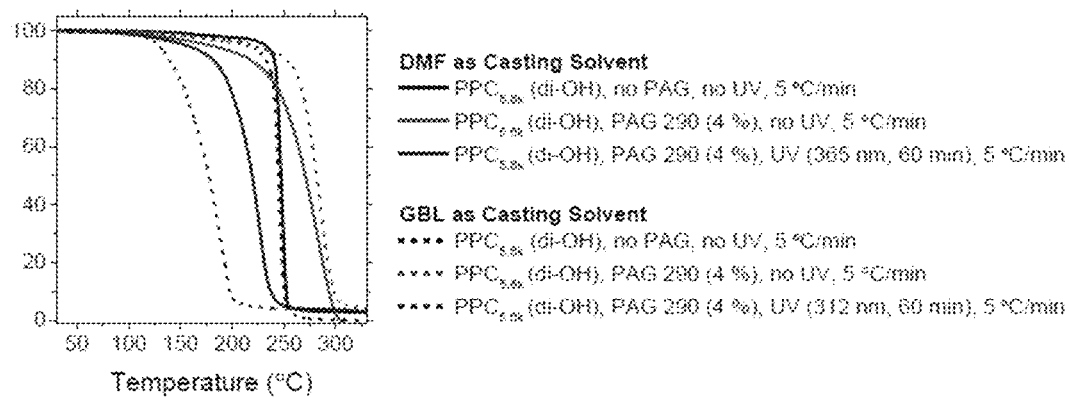
FIG. 31 shows the effect of casting solvent on time-dependent thermal degradation of PPC data shown for DMF as the solvent
Figure 32:
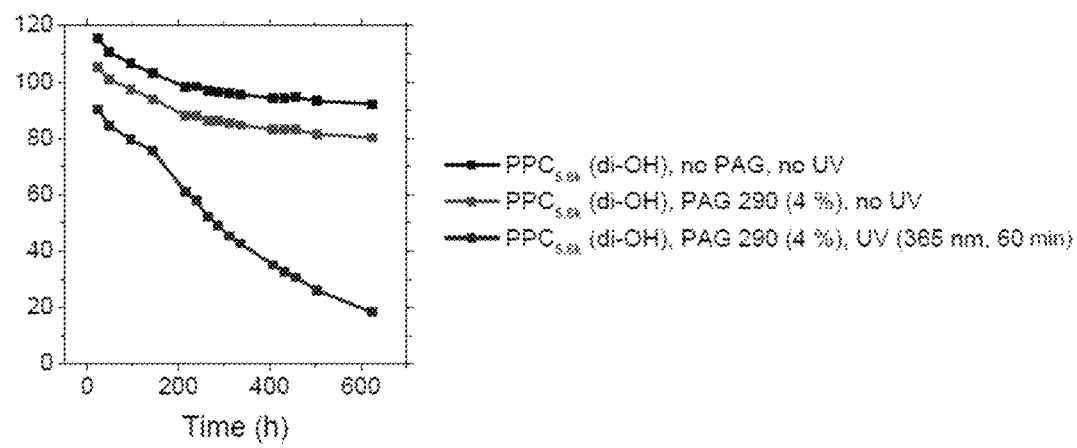
FIG. 32 shows the thermal degradation of PPC in water. Samples were heated in water at 80° C. for 20 hours and dried under vacuum at room temperature. The x-axis means drying time.
Figure 33:
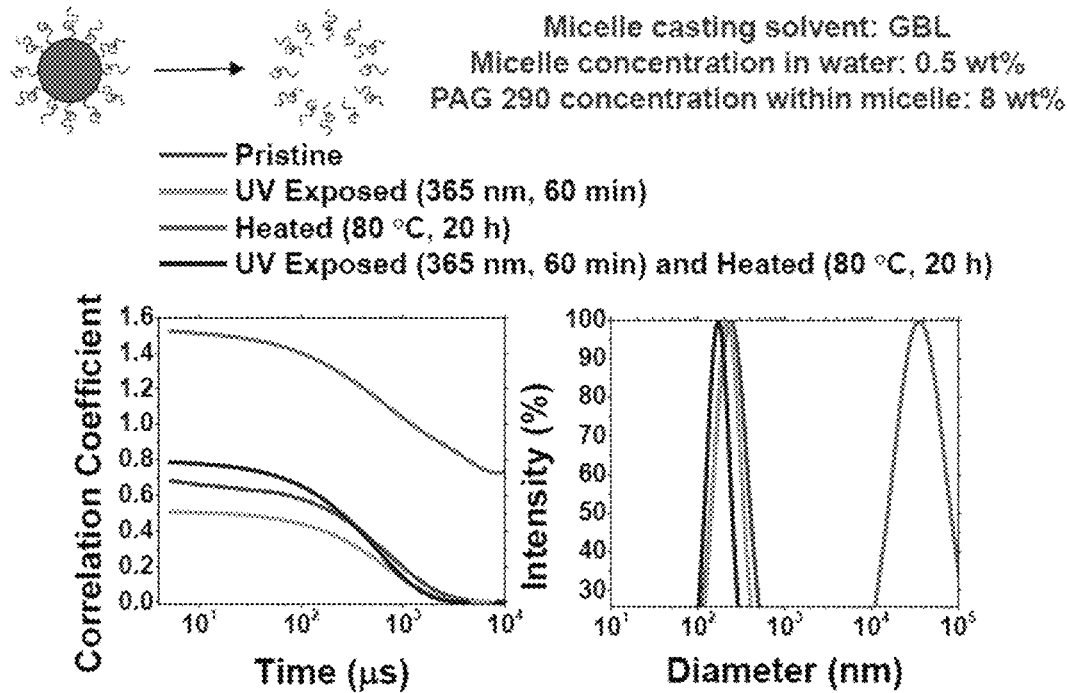
FIG. 33 shows DLS data demonstrating thermal degradation of PPEGMA-PPC-PPEGMA micelles in water.
Figure 34:
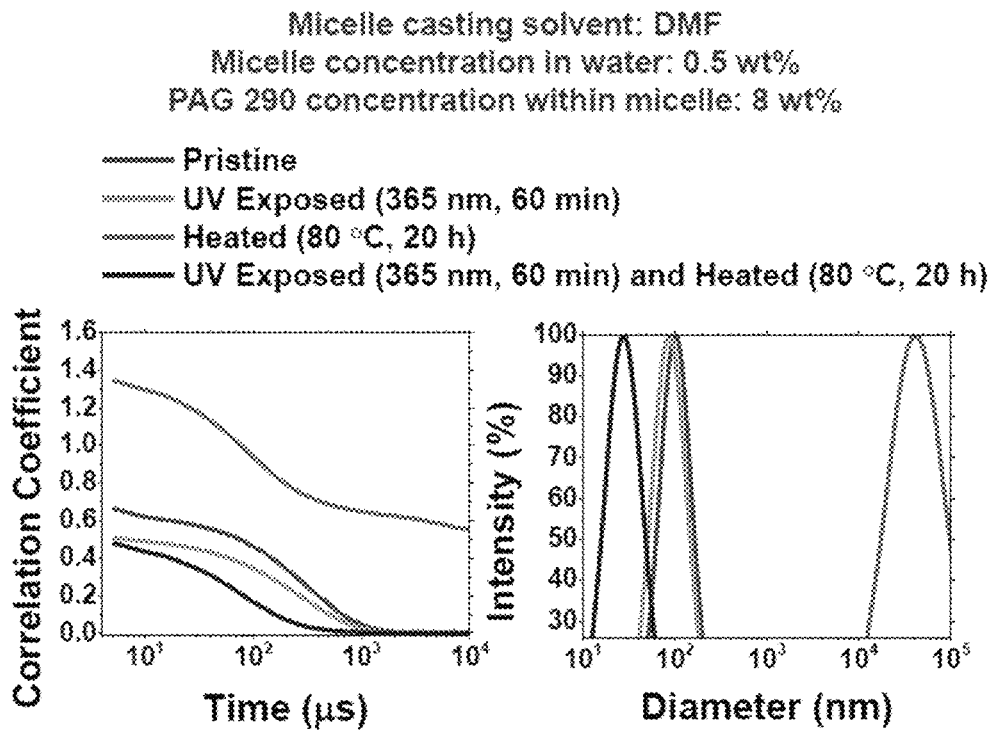
FIG. 34 shows DLS data demonstrating thermal degradation of PPEGMA-PPC-PPEGMA micelles in water.
Figure 40:
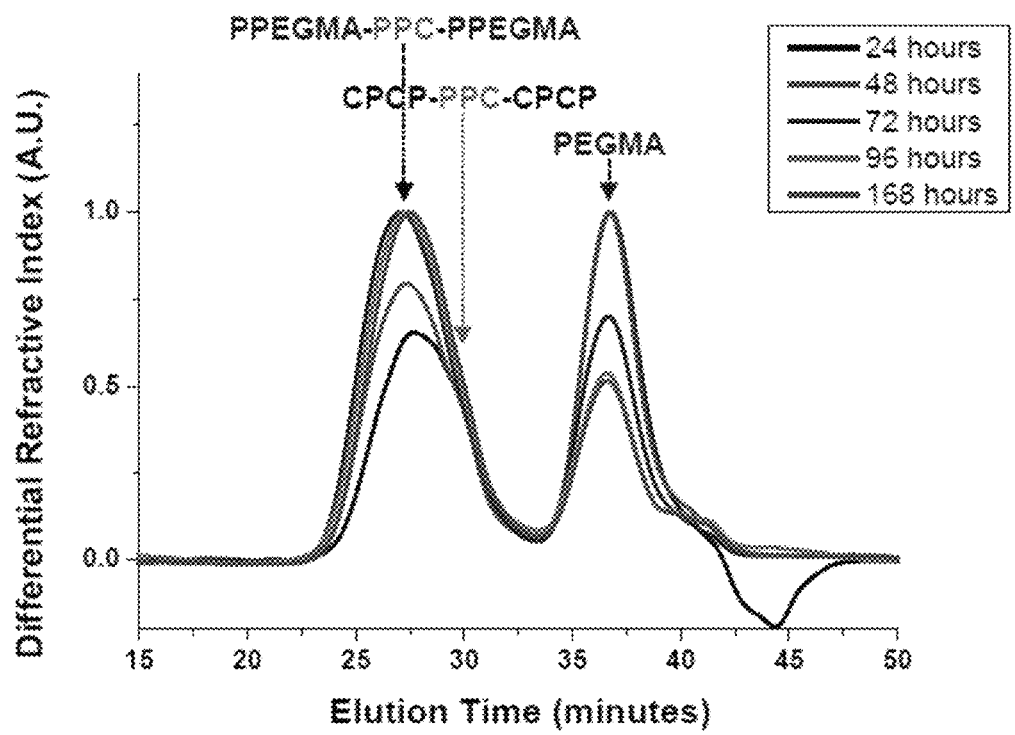
FIG. 40 shows representative GPC traces and the effect of reaction time.
Figure 41:
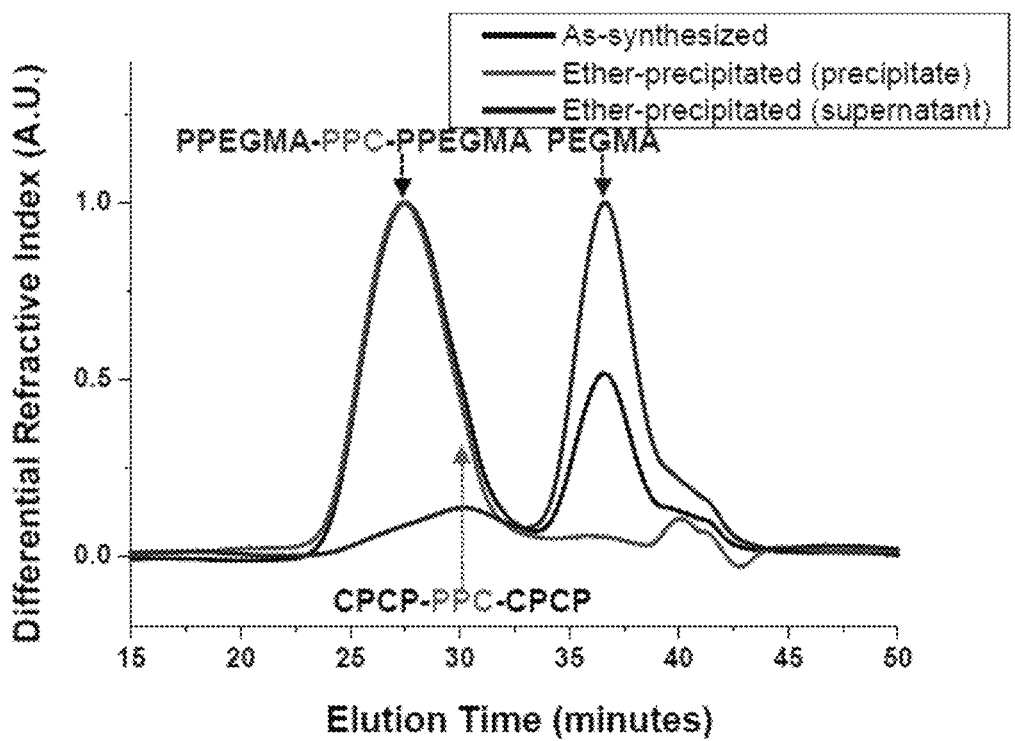
FIG. 41 shows representative GPC traces to remove unreacted PPEGMA. Purified mono-modal product: PPC: PPEGMA=50:50, PDI=1.52.
Figure 42:
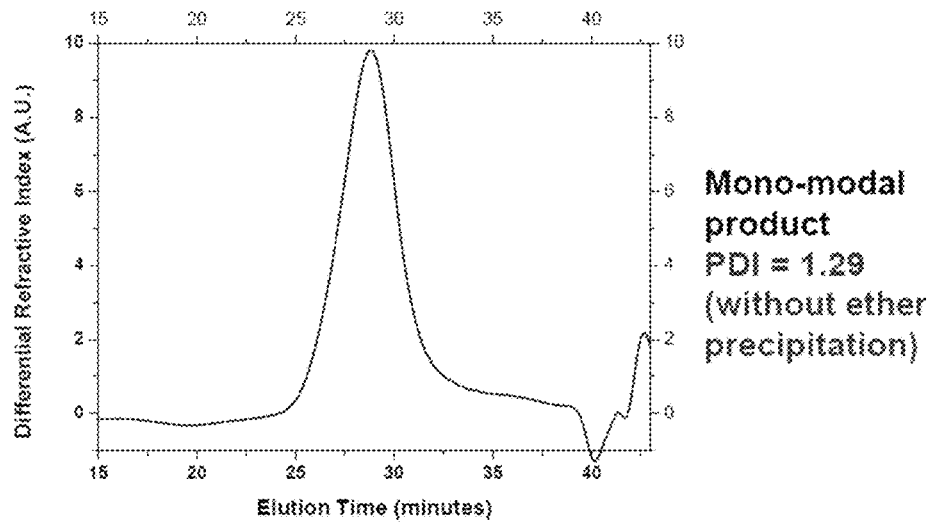
FIG. 42 shows a representative GPC trace: modified synthesis procedure; remove inhibitor from PEGMA monomer using $Al_2O_3+MgSO_4$. Polymerized for 48 hours. Monomodal product PDI=1.29 (without ether precipitation)
Figure 43:
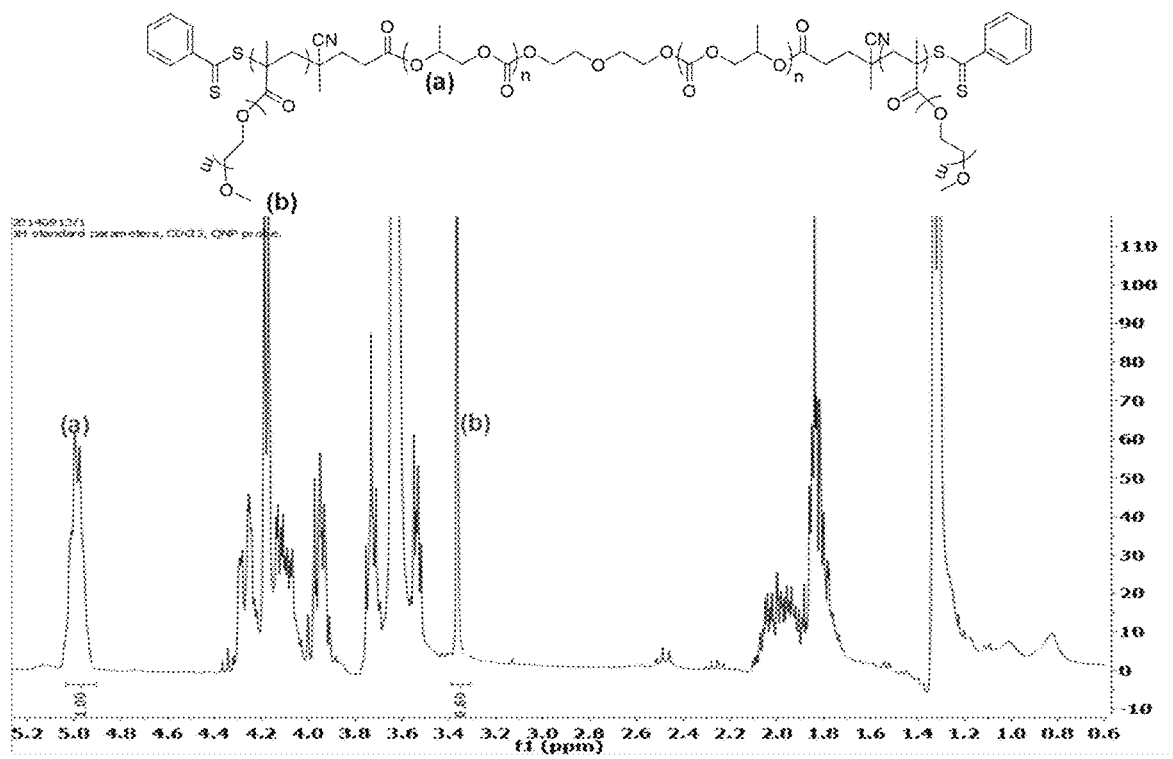
FIG. 43 shows representative 1H NMR spectra; modified synthesis procedure; remove inhibitor from PEGMA monomer using $Al_2O_3+MgSO_4$. Polymerized for 48 hours. Monomodal product PPC:PPEGMA=51:49 (target composition achieved at complete conversion).
Figure 46:
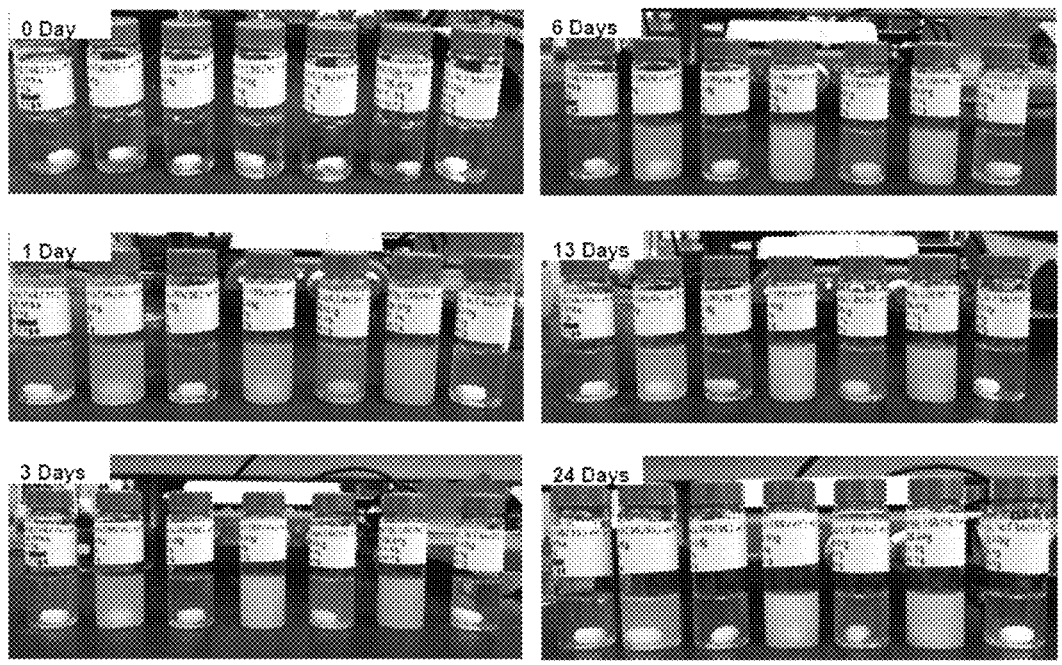
FIG. 46 shows images of polymer samples following direct hydration at 25° C. under magnetic stirring. The samples correspond to the samples shown in the table of FIG. 45.
Figure 47:
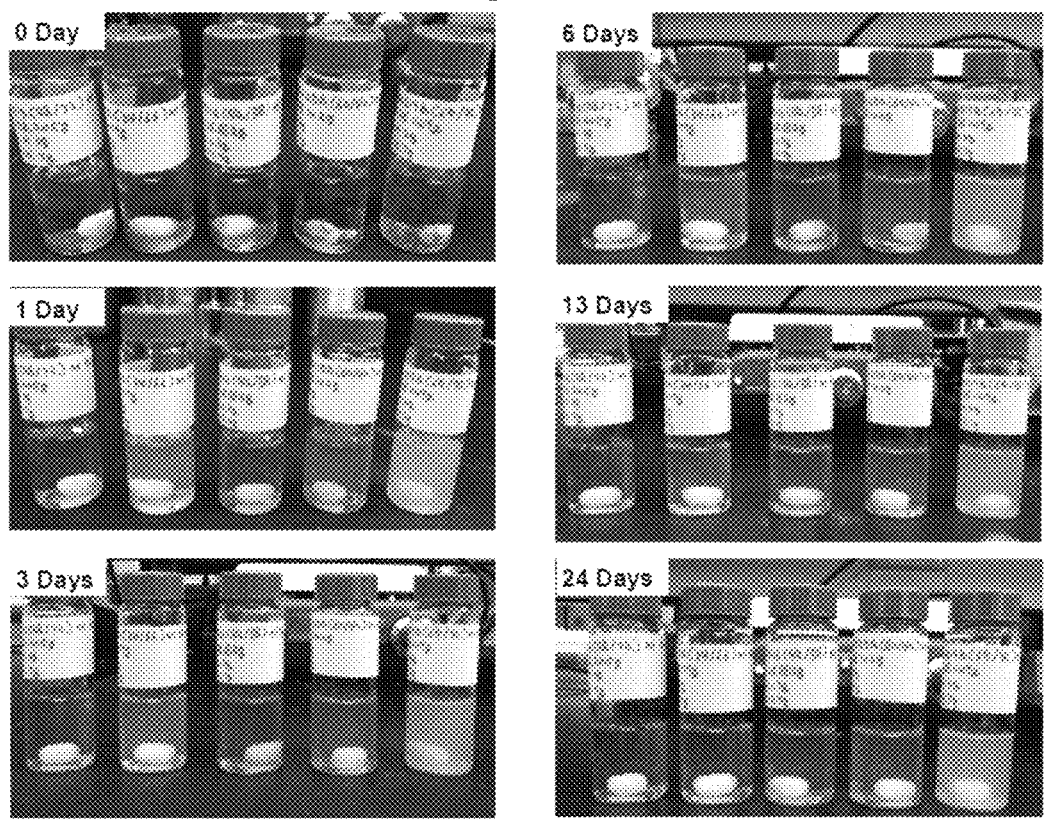
FIG. 47 shows images of polymer samples following direct hydration at 50° C. under magnetic stirring. The samples correspond to the samples shown in the table of FIG. 45.
Figures 48, 49:
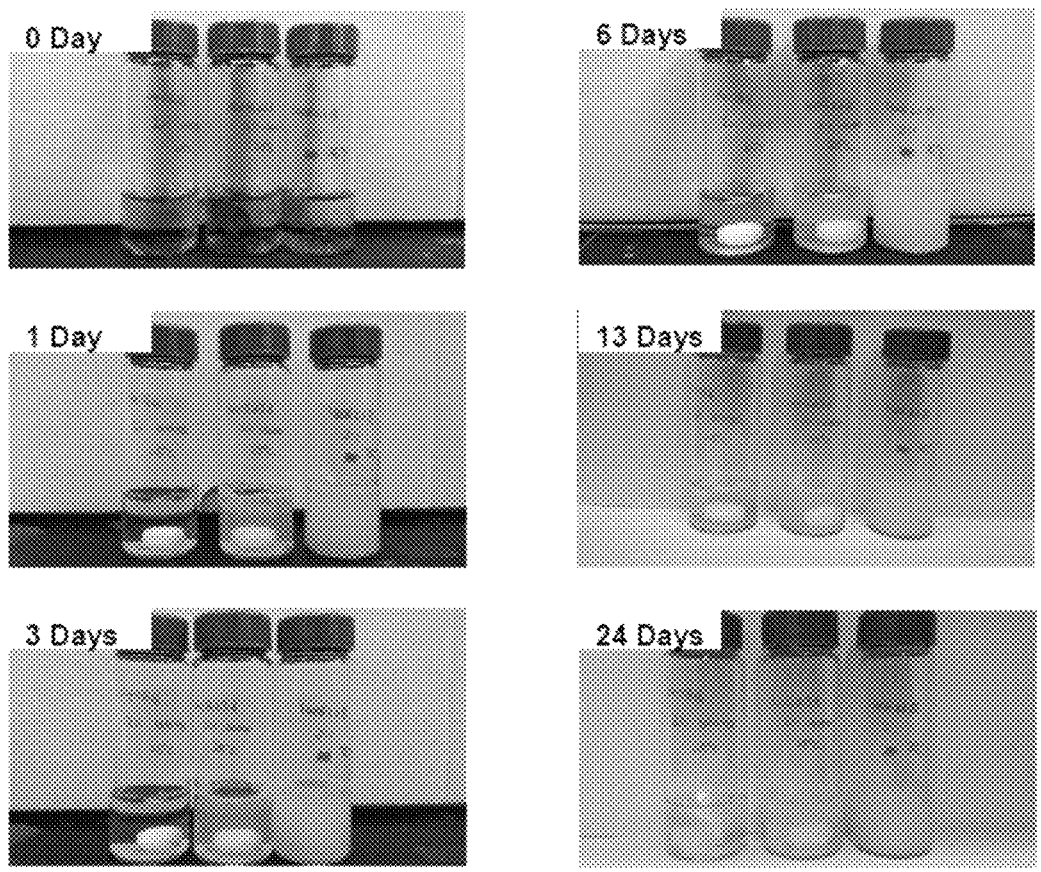
FIG. 48 shows the hydrodynamic diameters (nm) of particles formed in water by PPEGMA-PPC-PPEGMA polymers (2.0 wt. %) via direct hydration.
FIG. 49 shows images of polymer samples following direct hydration at 25° C. under magnetic stirring. The samples correspond to the samples shown in the table of FIG. 48.
Figure 50:
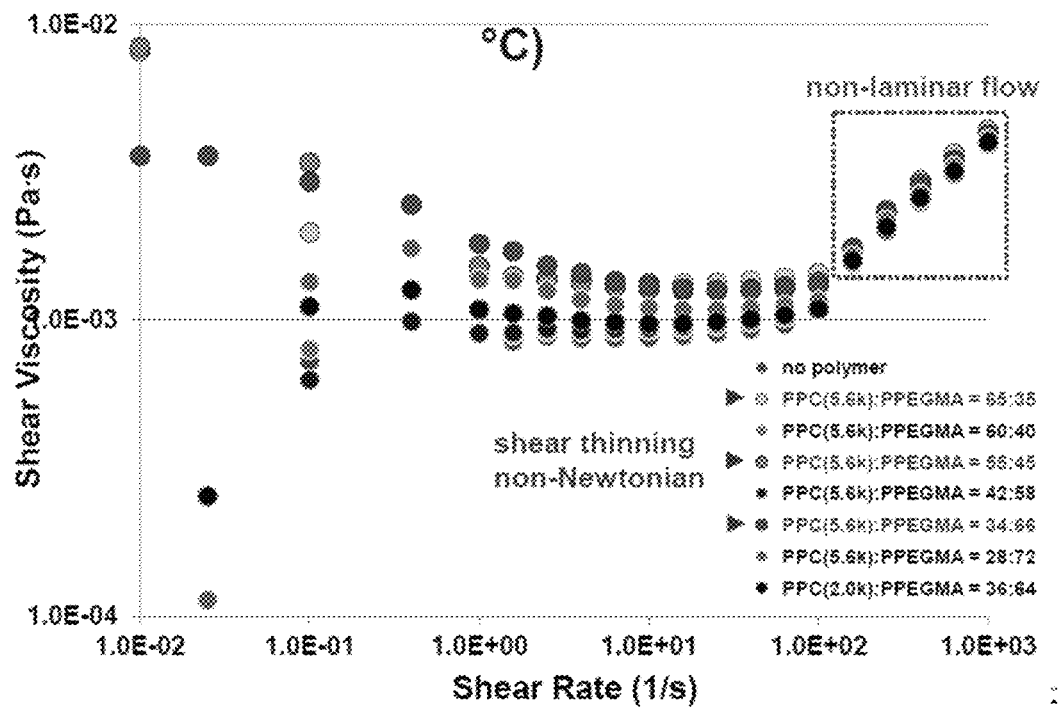
FIG. 50 shows steady shear viscosities of 1.0 wt. % PPEGMA-PPC-PPEGMA solutions in water as a function of shear rate (polymers dissolved via direct hydration at 25° C.
Figure 51:
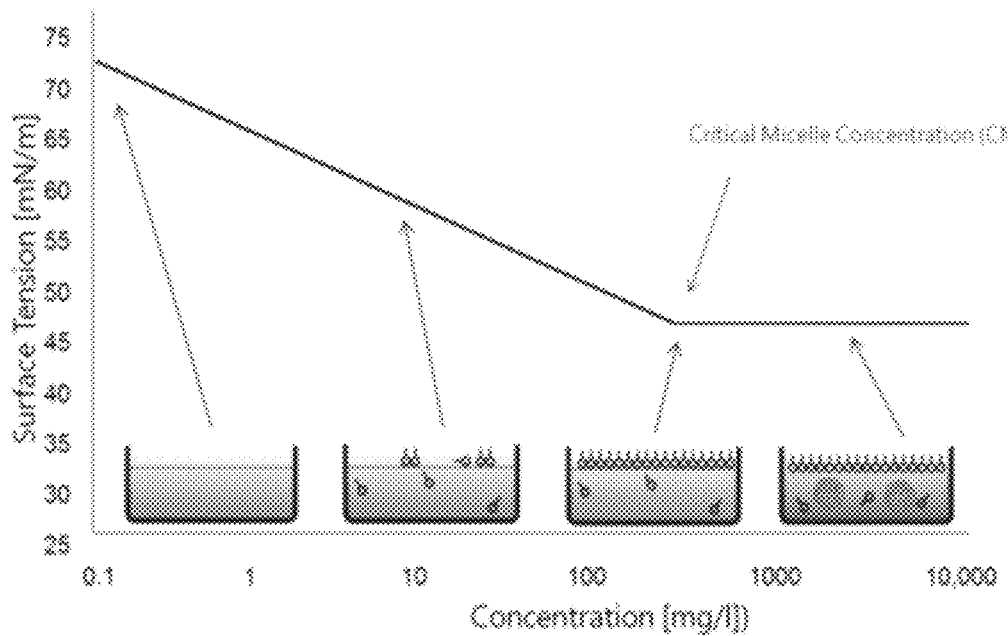
FIG. 51 depicts a scheme showing the critical micellization concentration (CMC) of a surfactant by surface tension measurements.
Figure 52:
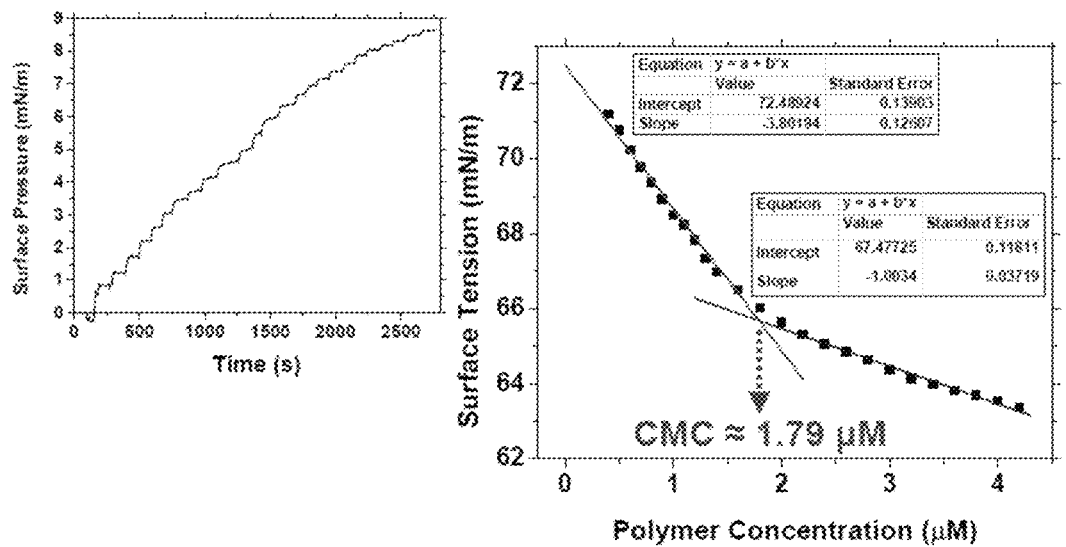
FIG. 52 depicts a plot showing surface tension vs. polymer concentration: 140425A (fractionated PPC: PPEGMA=60:40 by weight, Mn=9.4 kg/mol, spread 25° C.-dissolved 41-nm micelles on water).
Figure 53:
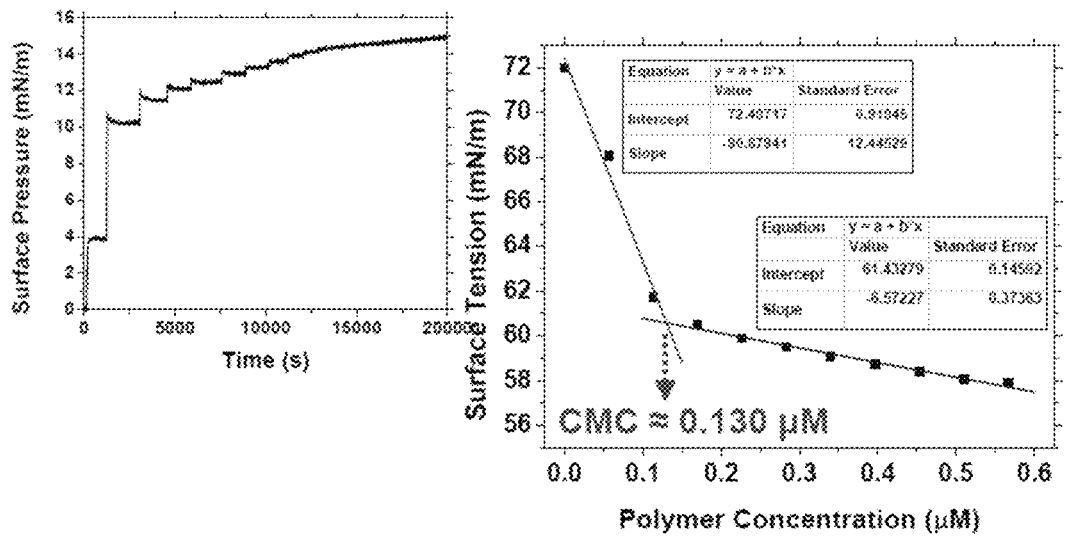
FIG. 53 depicts a plot showing surface tension vs. polymer concentration: 140519A (fractionated PPC: PPEGMA=34:66 by weight, Mn=16.4 kg/mol, spread 25° C.-dissolved 151-nm micelles on water surface).
Figure 54:
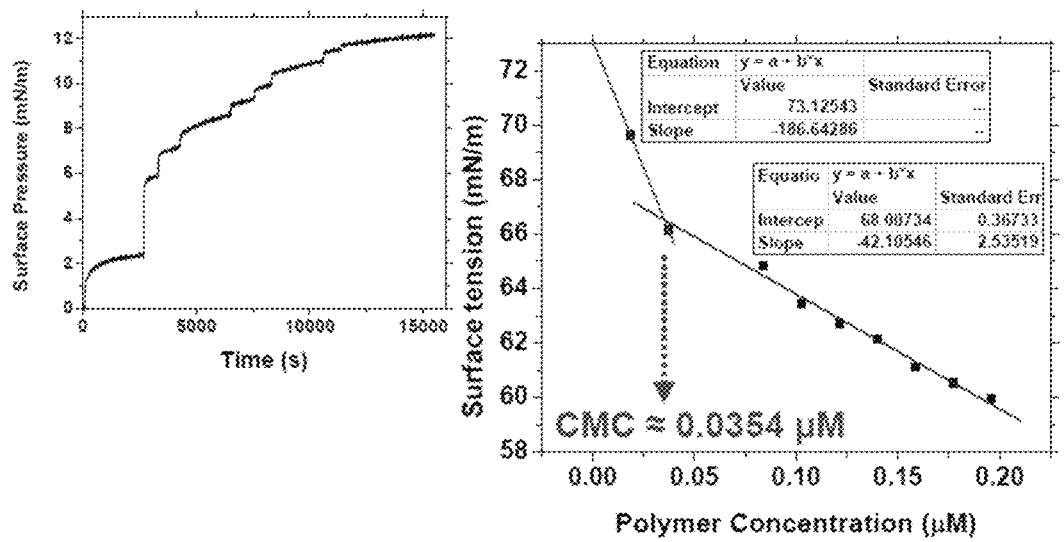
FIG. 54 depicts a plot showing surface tension vs. polymer concentration: 140418A (fractionated PPC: PPEGMA=28:72 by weight, Mn=20.1 kg/mol, spread 25° C.-dissolved 39-nm micelles on water surface).
Figure 55:
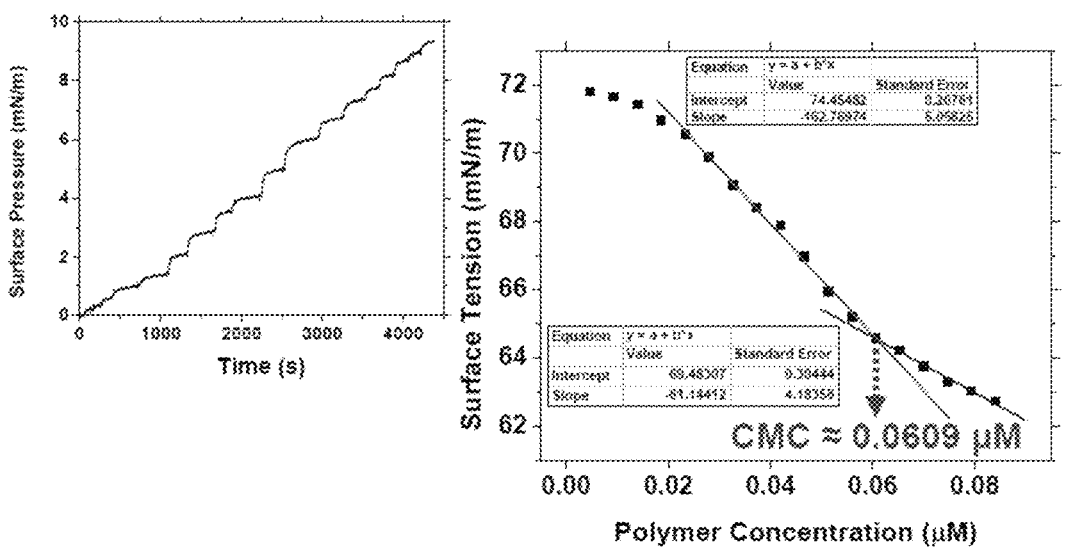
FIG. 55 depicts a plot showing surface tension vs. polymer concentration: 1404816 (Mono-Modal, PPC: PPEGMA=28:72 by weight, Mn=20.1 kg/mol, spread 25° C.-dissolved 27-nm micelles on water surface).
Figure 56:
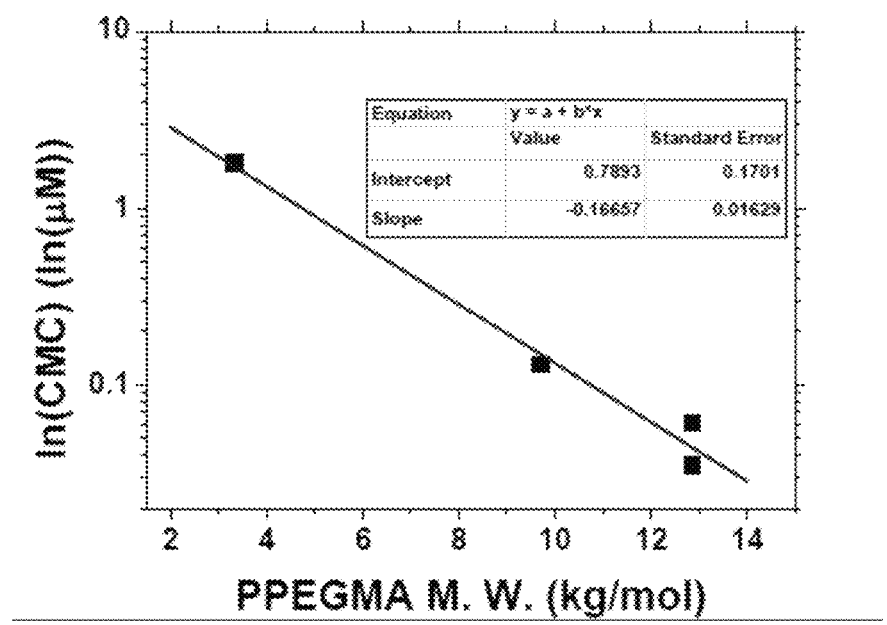
FIG. 56 depicts CMC diameter vs. PPEGMA MW (kg/mol).
Figure 57:
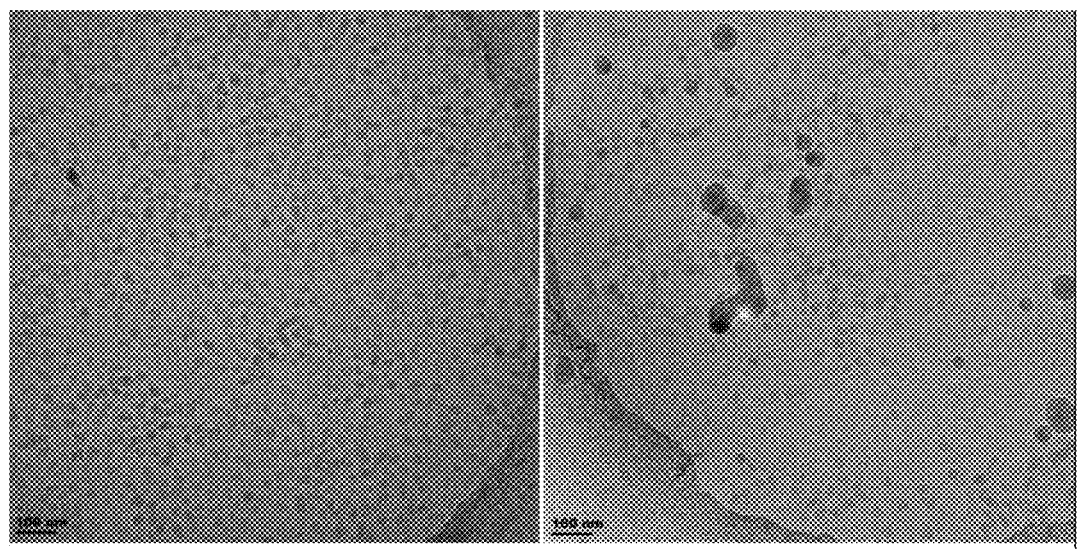
FIG. 57 depicts Cryo TEM image of sample 140519B (fractionated, PPC:PPEGMA=65:35 by weight, Mn=8.6 kg/mol, 25° C.-dissolved/diluted to 0.5 wt. %, 788 nm Diameter Particles, Shear Thinning). The image shows aggregates of spherical micelles.
Figure 58:
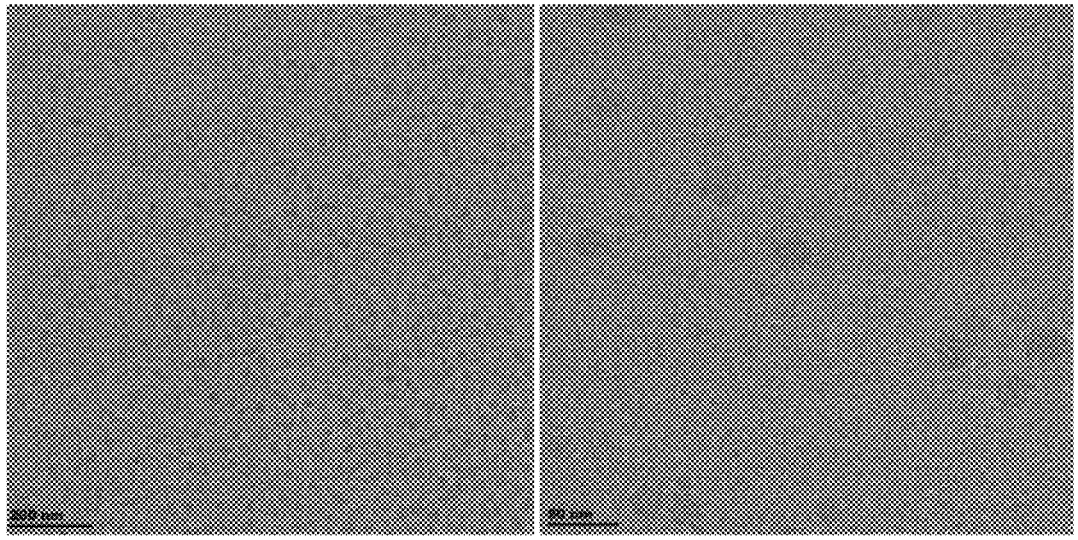
FIG. 58 depicts a Cryo TEM image of sample 140425A (fractionated, PPC:PPEGMA=60:40 by weight, Mn=9.4 kg/mol, 25° C.-dissolved/diluted to 0.5 wt. %, 41 nm diameter micelles, Newtonian). The image shows well-dispersed spherical micelles.
Figure 59:
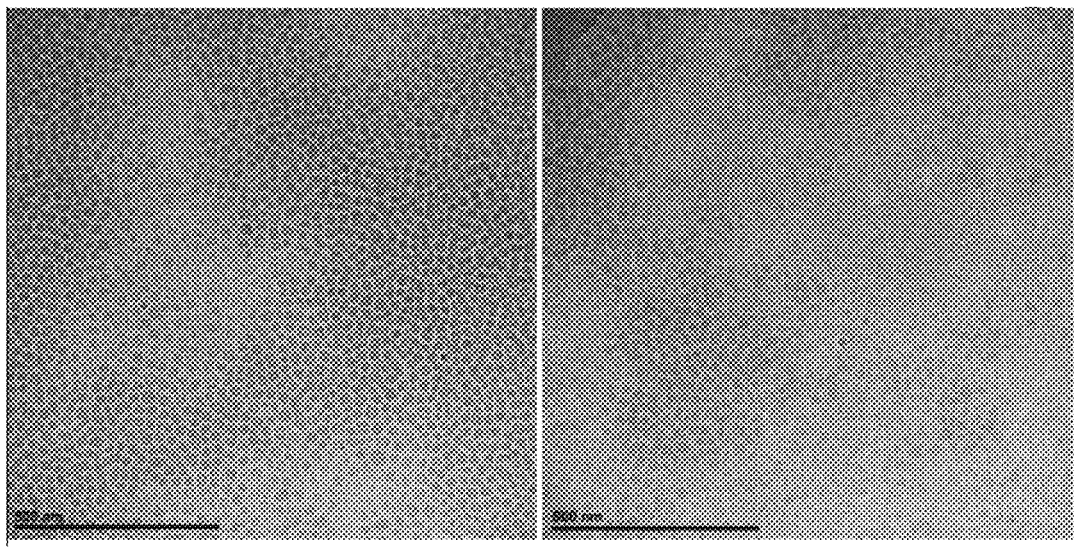
FIG. 59 shows a Cryo TEM image of sample 140217 (fractionated, PPC:PPEGMA=55:45 by weight, Mn=10.2 kg/mol, 25° C.-dissolved/diluted to 0.5 wt. %, 745 nm Diameter Particles, Shear Thinning). The image shows aggregates of spherical particles.
Figure 60:
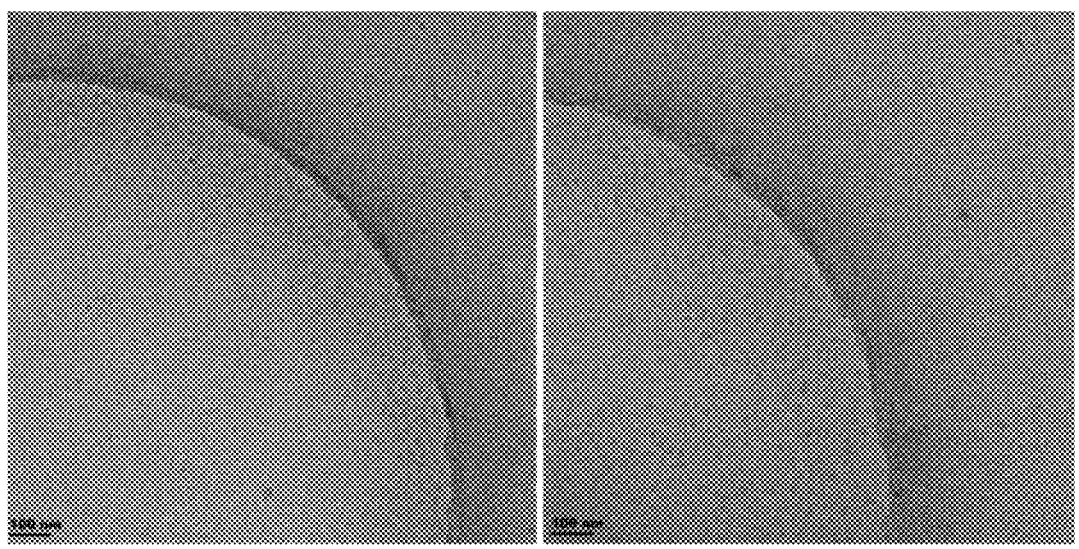
FIG. 60 shows a Cryo TEM image of sample 140416 (fractionated, PPC:PPEGMA=42:58 by weight, Mn=13.4 kg/mol, 25° C.-dissolved/diluted to 0.5 wt. %, 34 nm diameter micelles, Newtonian). The image shows well-dispersed spherical micelles.
Figure 61:
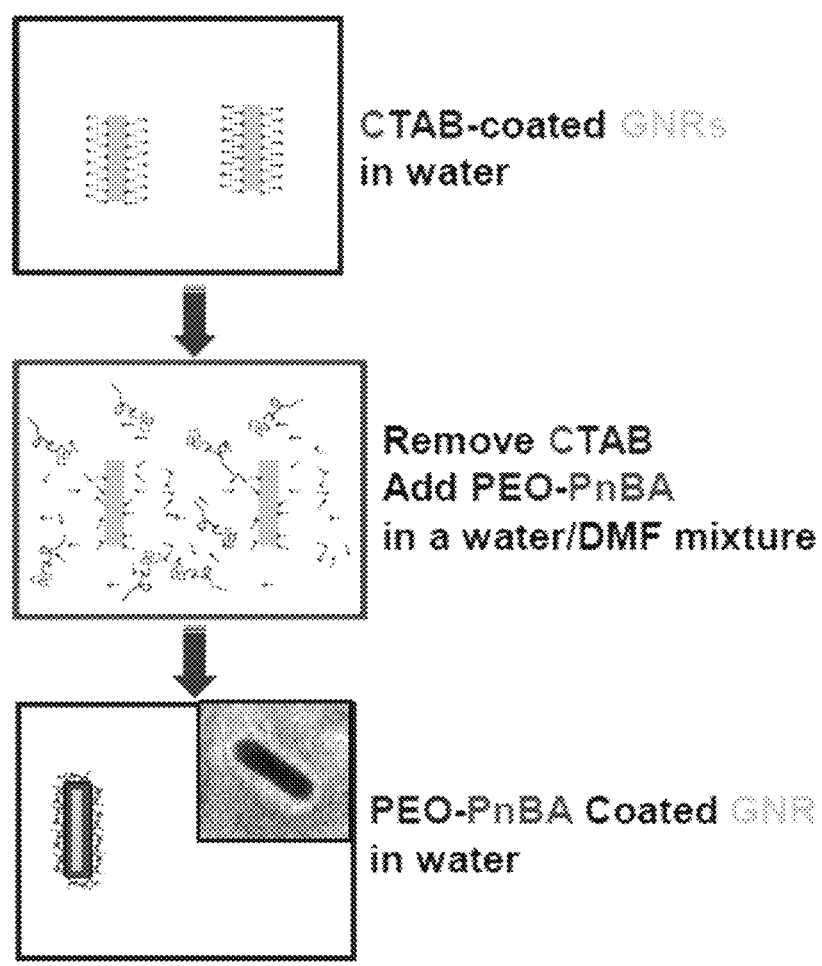
FIG. 61 depicts a scheme showing the encapsulation of gold nanorods (GNRs) into block copolymer micelles.
Figure 62:
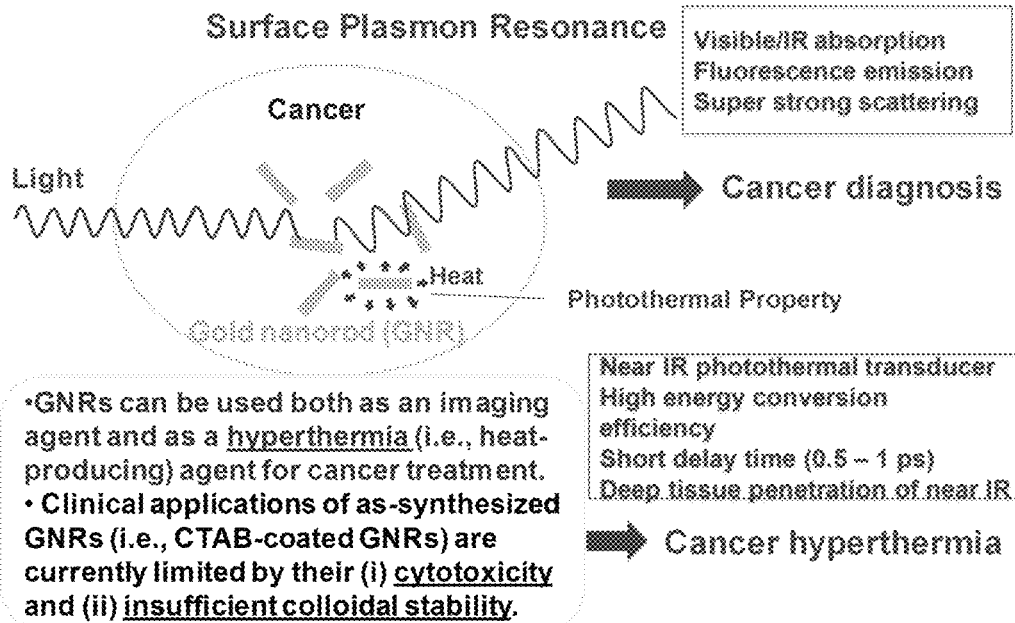
FIG. 62 depicts possible routes for biomedical applications of gold nanorods.
Figure 63:
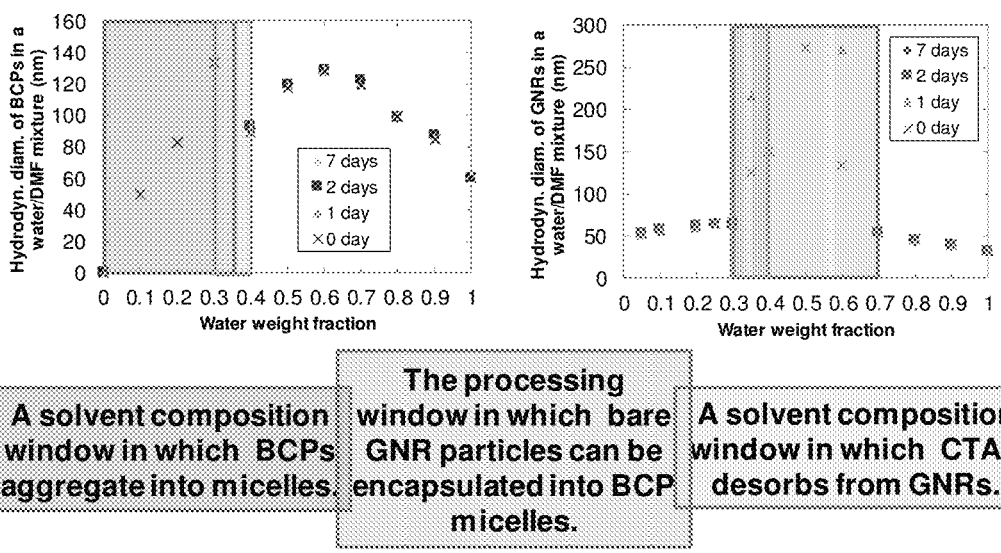
FIG. 63 depicts data for a novel self-assembly processing technique for encapsulation of GNRs in BCP micelles via a solvent exchange process.
Figure 64:
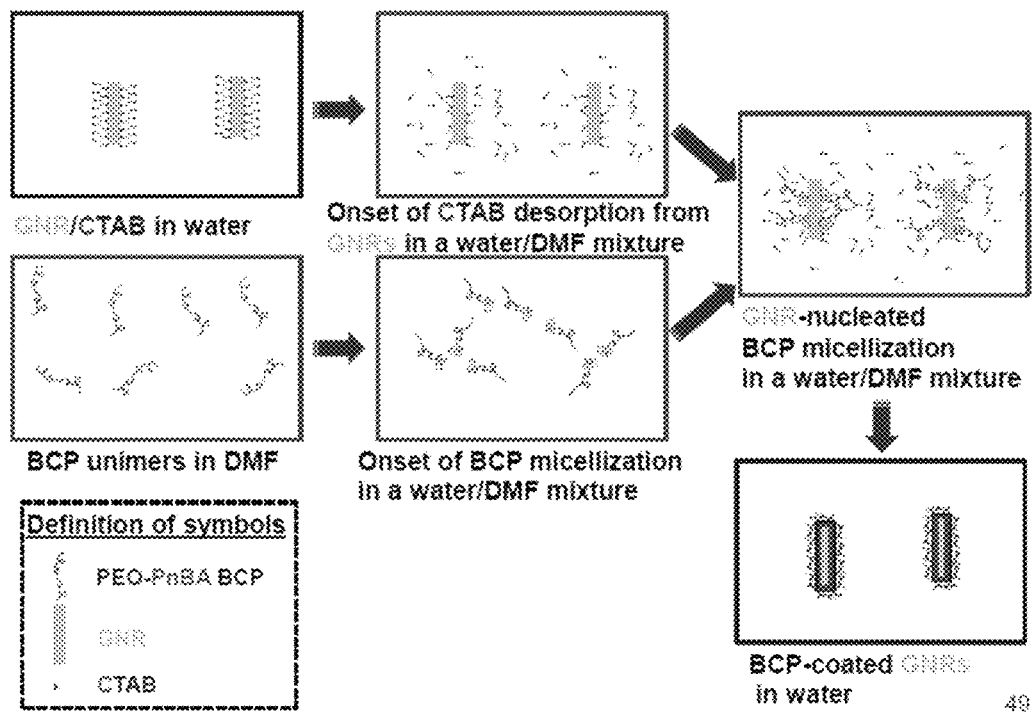
FIG. 64 depicts procedures for encapsulation of GNRs into BCP micelles.
Figure 65:
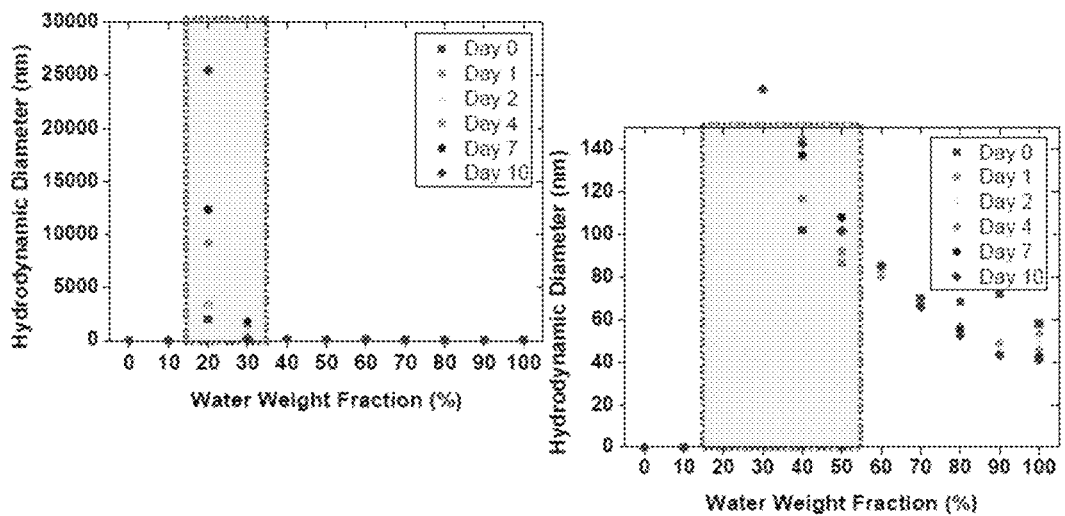
FIG. 65 depicts the hydrodynamic diameter of PPEGMA-PPC-PPEGMA micelles in water/DMF mixtures: 140425A (fractionated, PPC:PPEGMA=60:40 by weight, Mn=9.4 kg/mol, polymer conc.=0.1 wt. %).
Figure 66:
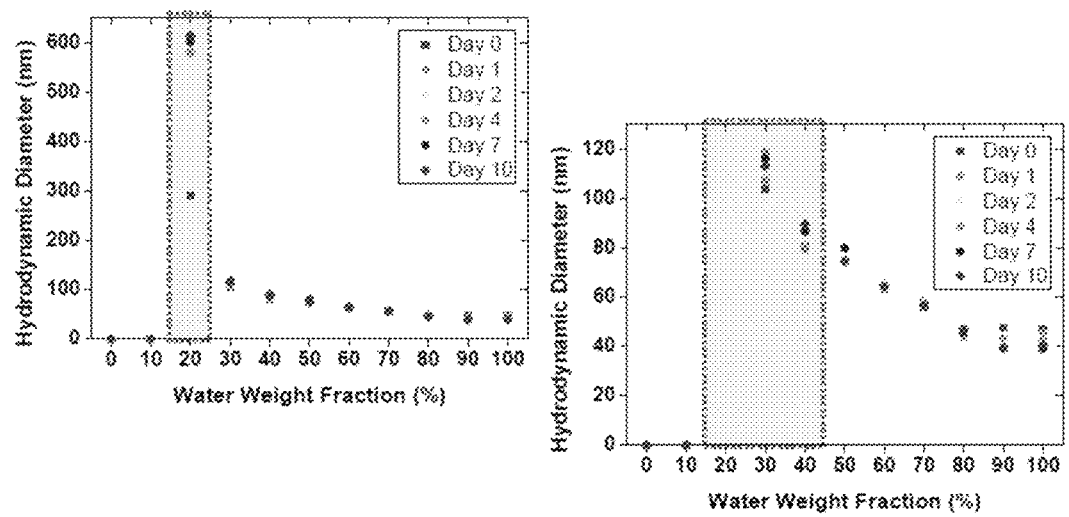
FIG. 66 depicts a hydrodynamic diameter of PPEGMA-PPC-PPEGMA micelles in water/DMF mixtures: 140823A (mono-modal, PPC:PPEGMA=52:48 by weight, Mn=11.6 kg/mol, polymer conc.=0.1 wt. %).
Figure 67:
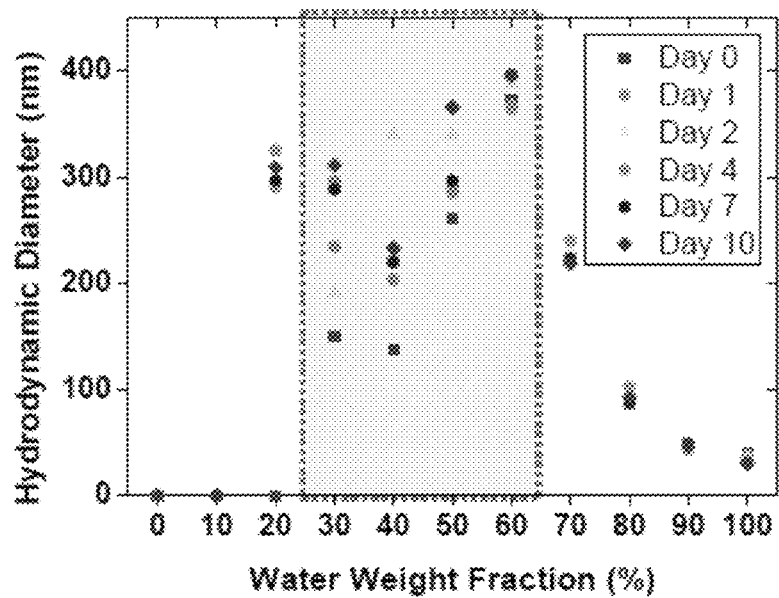
FIG. 67 depicts a hydrodynamic diameter of PPEGMA-PPC-PPEGMA micelles in water/DMF mixtures: 140816 (mono-modal, PPC:PPEGMA=28:72 by weight, Mn=20.1 kg/mol, polymer conc.=0.1 wt. %).
Figure 68:
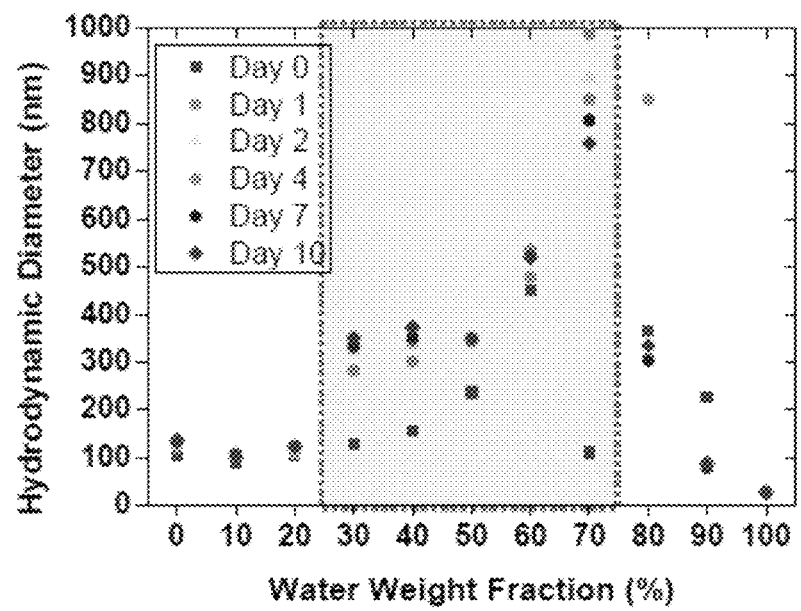
FIG. 68 depicts a hydrodynamic diameter of GNRs in water/DMF mixtures: (as-synthesized GNRs, GNR conc.=10 µg/ml, contains relatively high con. of CTAB≈3.2 wt. % (87 mM)).
Figure 69:
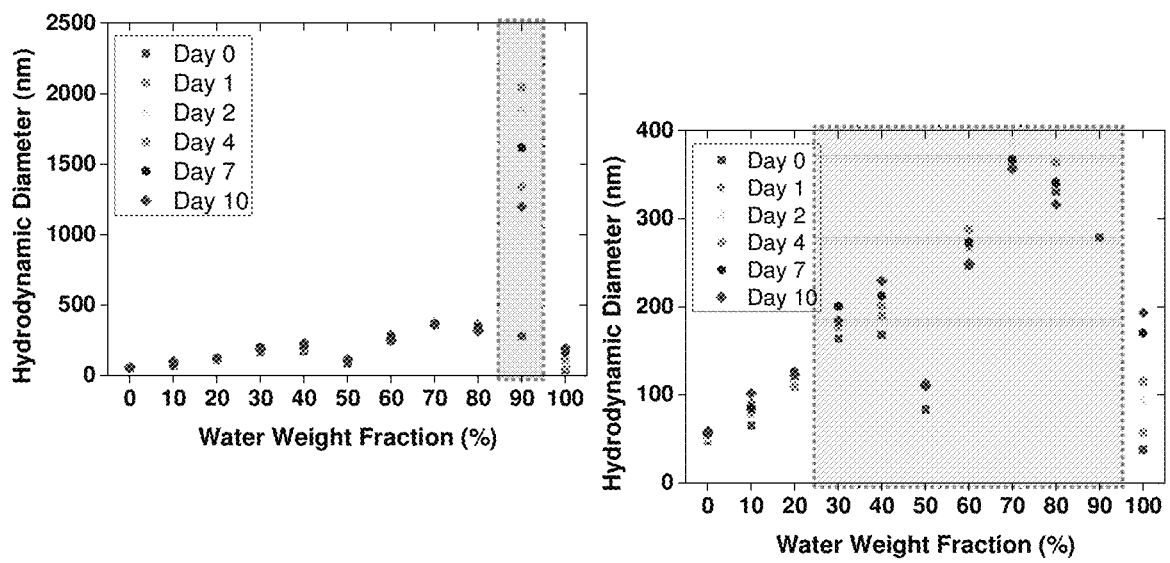
FIG. 69 depicts a hydrodynamic diameter of GNRs in water/DMF mixtures: (GNRs purified by precipitation at 0° C., GNR conc.=10 µg/mL, contains relatively medium con. of CTAB).
Figure 72:
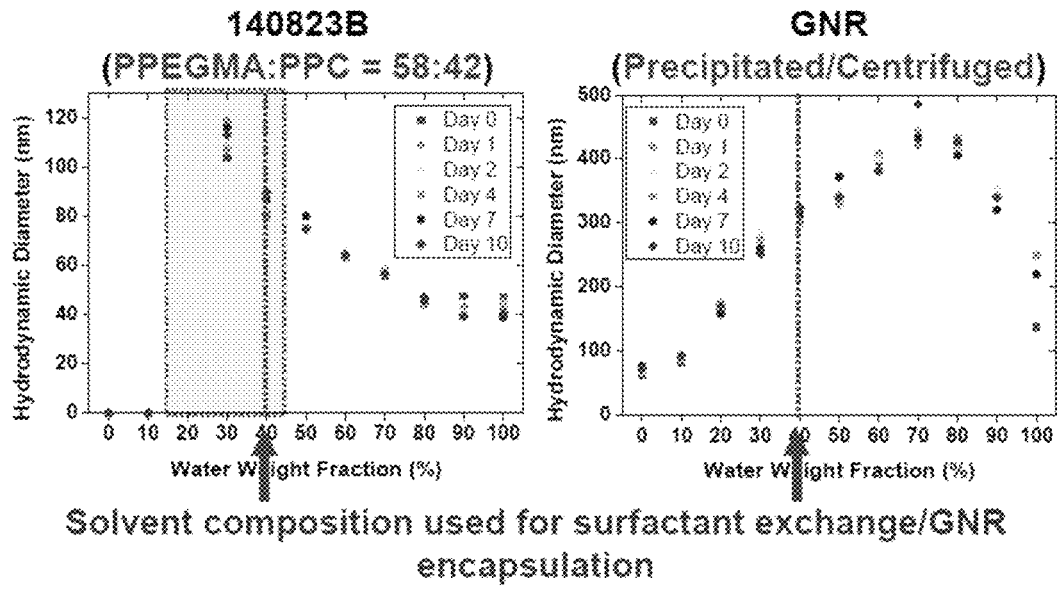
FIG. 72 depicts a summary of encapsulation condition.
Figure 73:
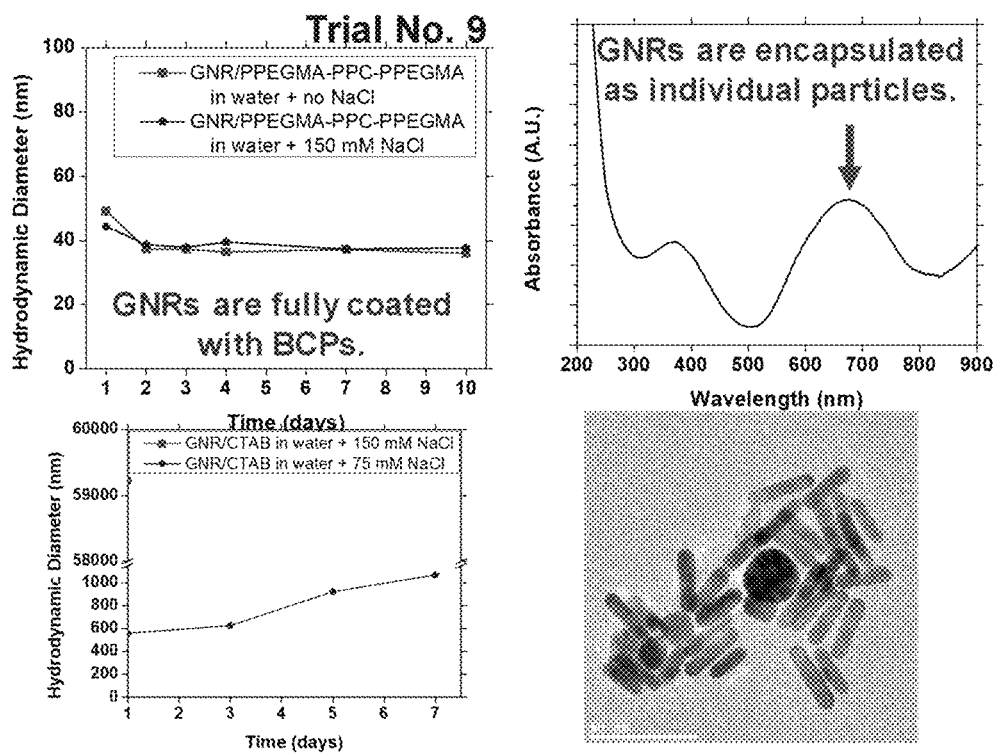
FIG. 73 shows data for GNR's coated by BCP's.
Figure 74:
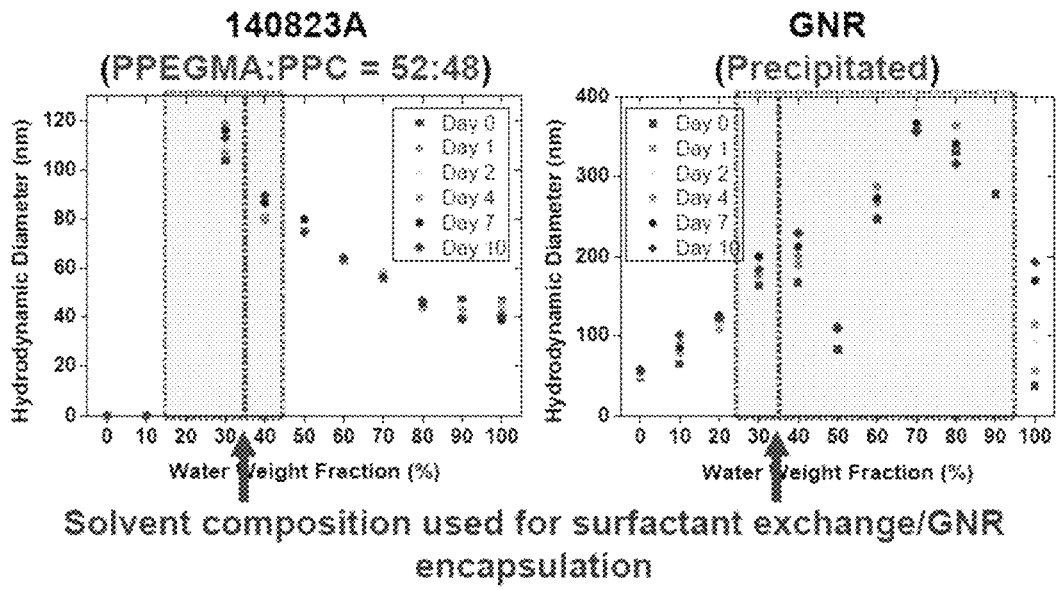
FIG. 74 depicts a summary of encapsulation condition used.
Figure 75:
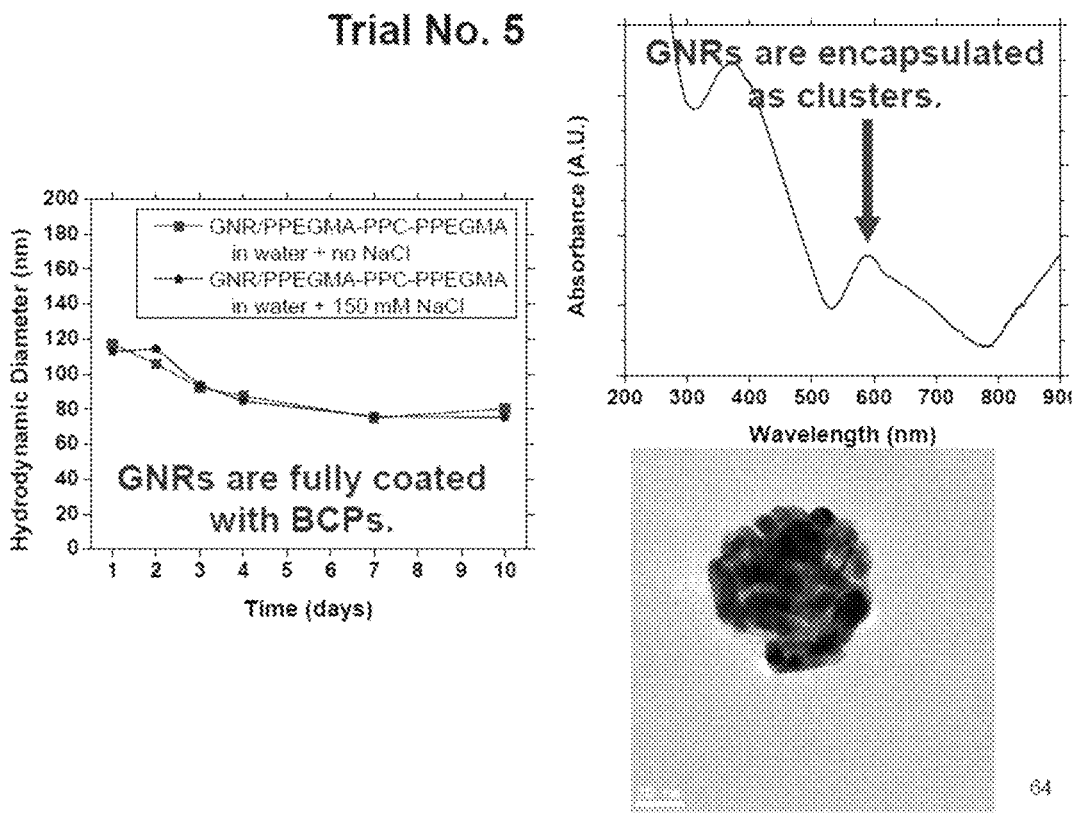
FIG. 75 shows data for GNR's coated by BCP's.
Figure 76:
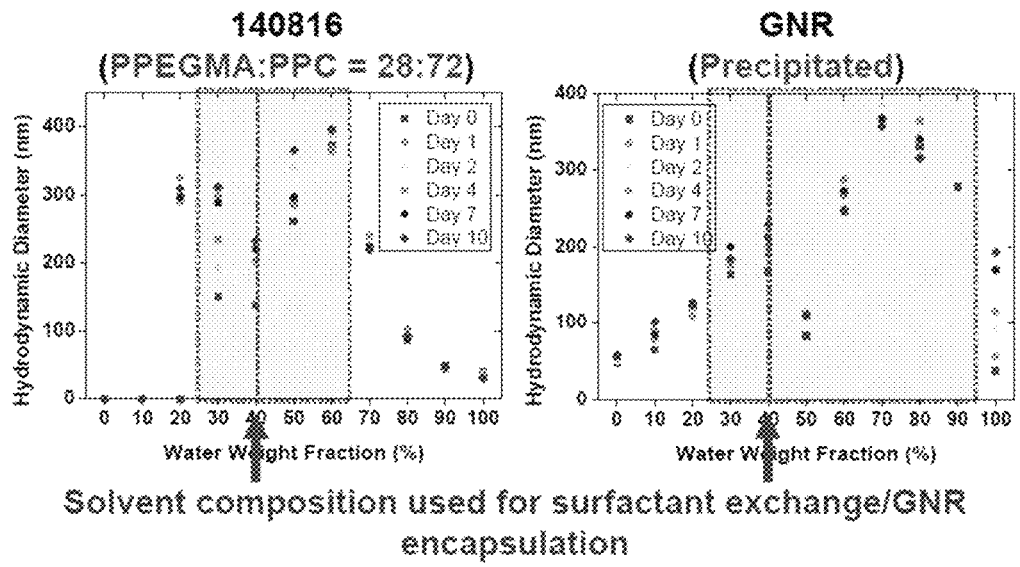
FIG. 76 depicts a summary of encapsulation condition used.
Figure 77:
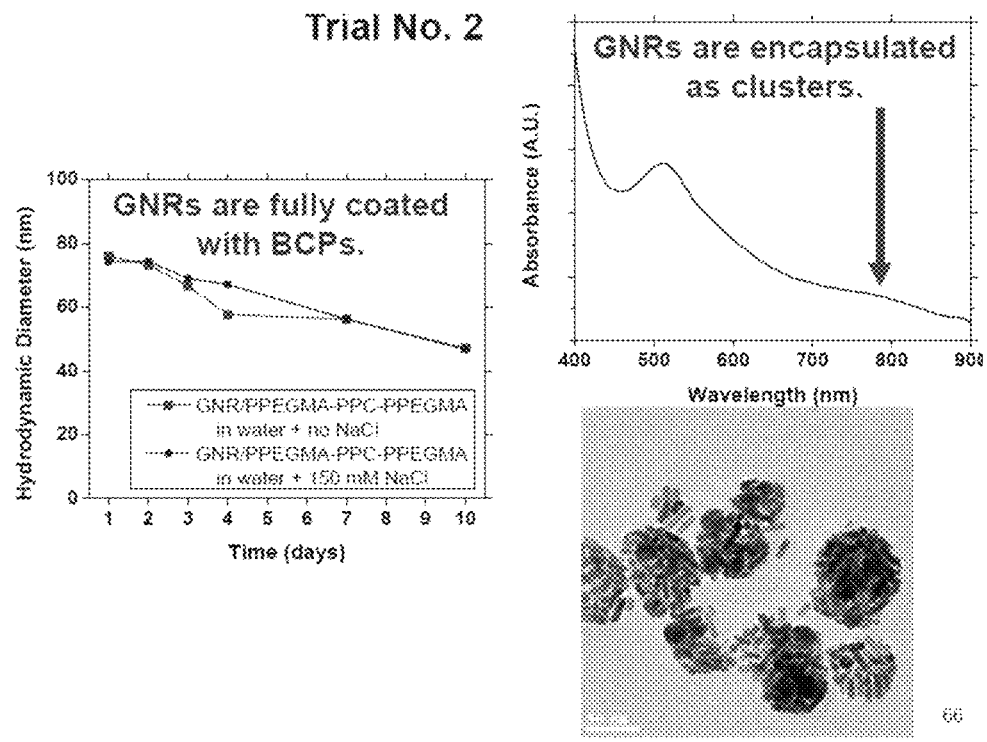
FIG. 77 depicts data for GNR's coated by BCP's.
Figure 78:
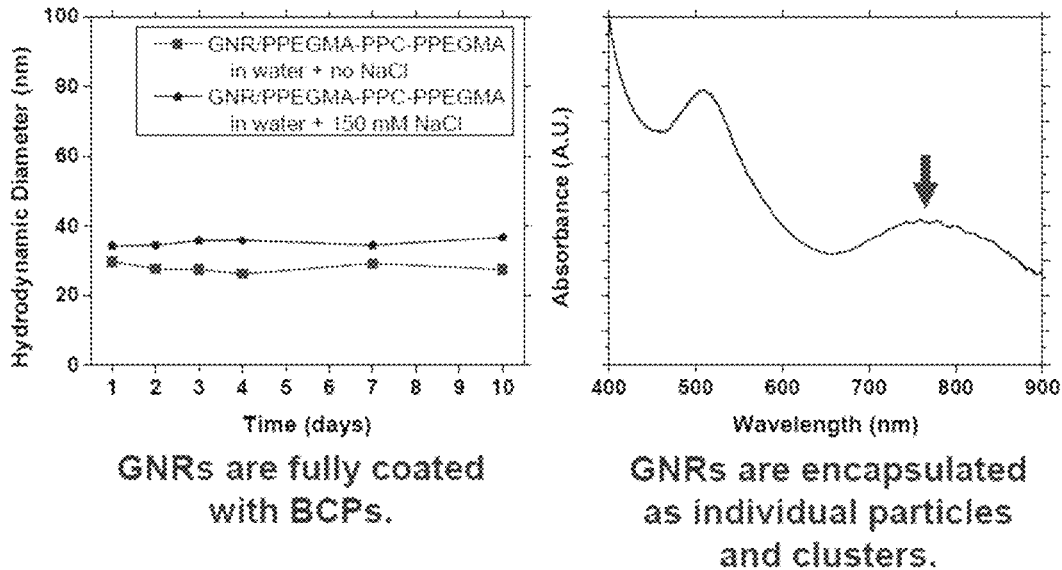
FIG. 78 depicts data for GNR's coated by BCP's for sample 140815 (PPEGMA:PPC=28:72)+GNR (as-synthesized).
Figure 79:
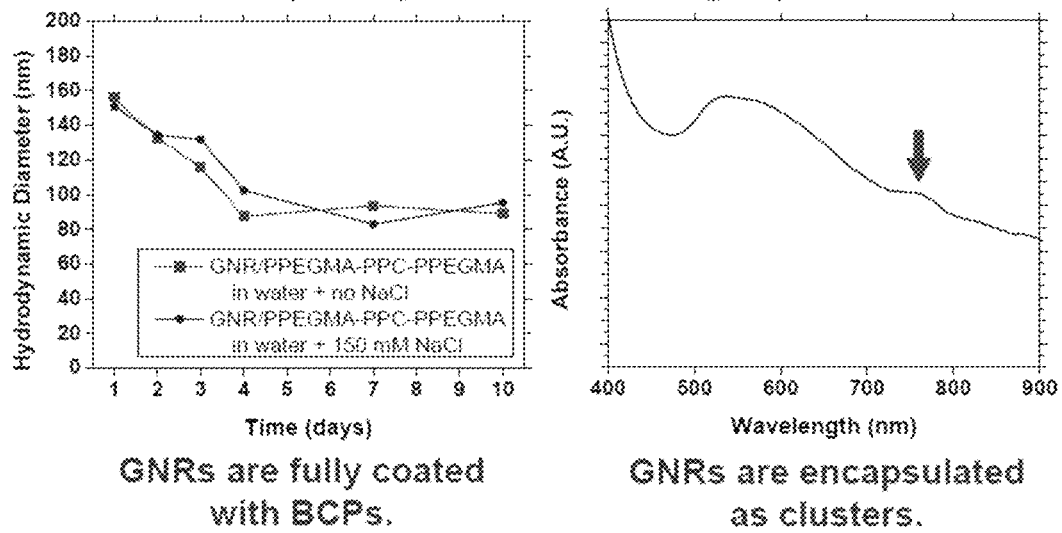
FIG. 79 depicts data for GNR's coated by BCP's for sample 140815 (PPEGMA:PPC=28:72)+GNR (precipitated/centrifuged).
Figure 80:
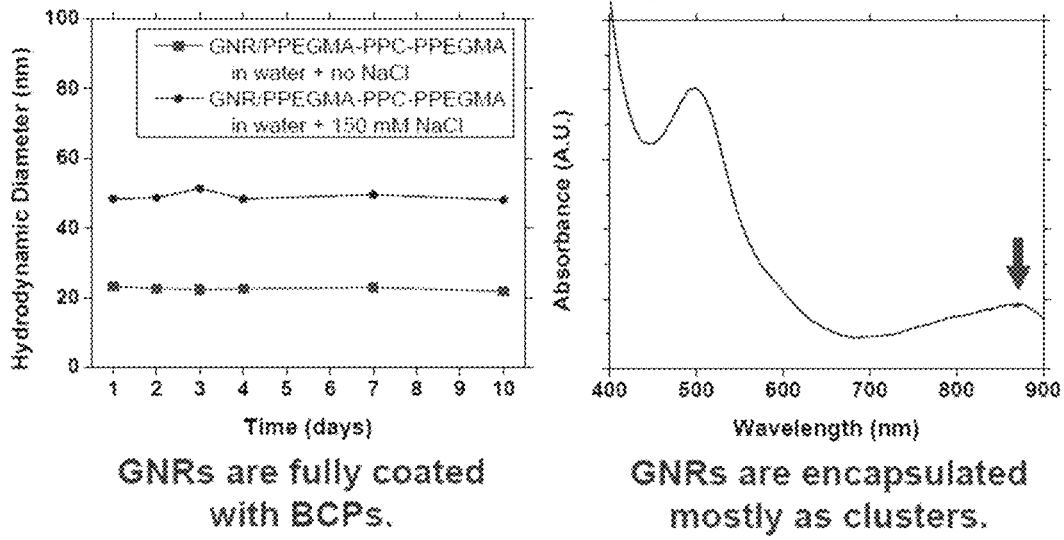
FIG. 80 depicts data for GNR's coated by BCP's for sample 140823A (PPEGMA:PPC=52:48)+GNR (as-synthesized).
Figure 81:
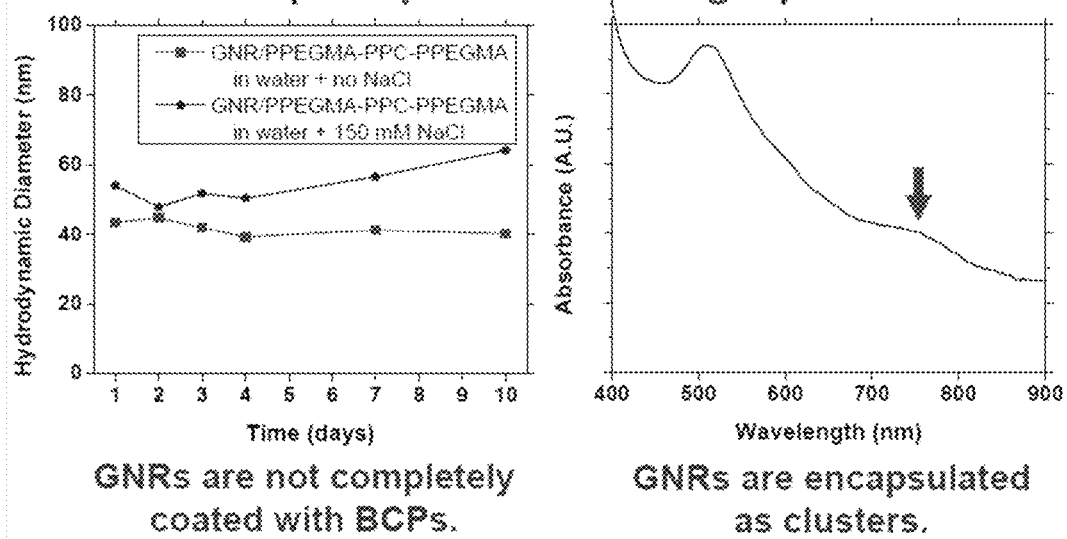
FIG. 81 depicts data for GNR's coated by BCP's for sample 140823A (PPEGMA:PPC=52:48)+GNR (precipitated/centrifuged).
Figure 82:
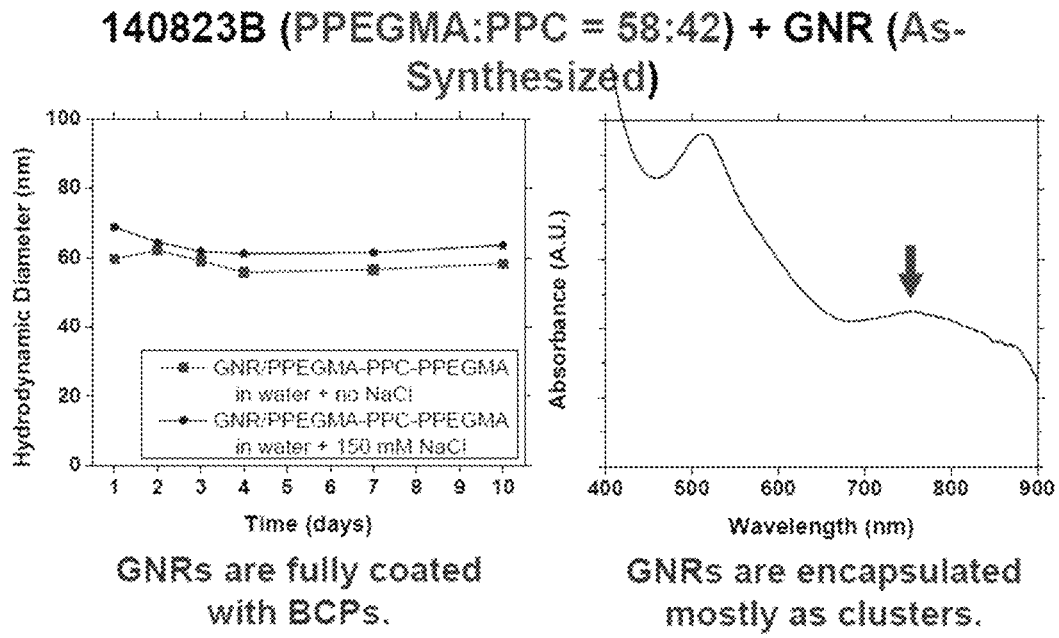
FIG. 82 depicts data for GNR's coated by BCP's for sample 140823B (PPEGMA:PPC=58:42)+GNR (as-synthesized).
Figure 83:
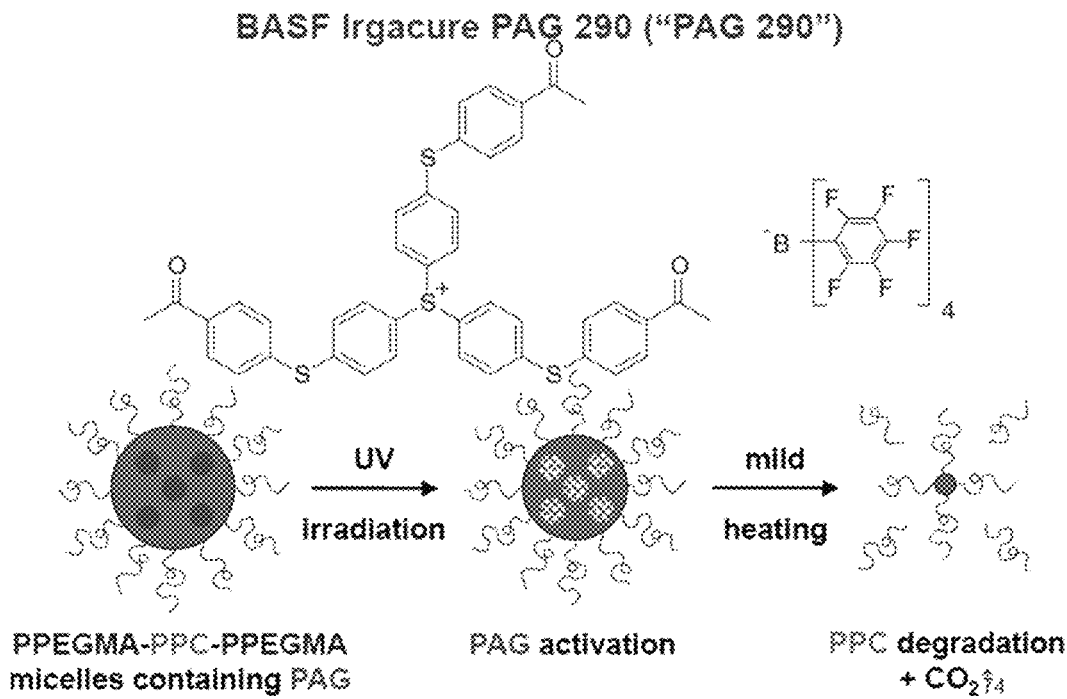
FIG. 83 depicts one PAG structure and a scheme for a polymeric micelle degradation process.
Figure 84:
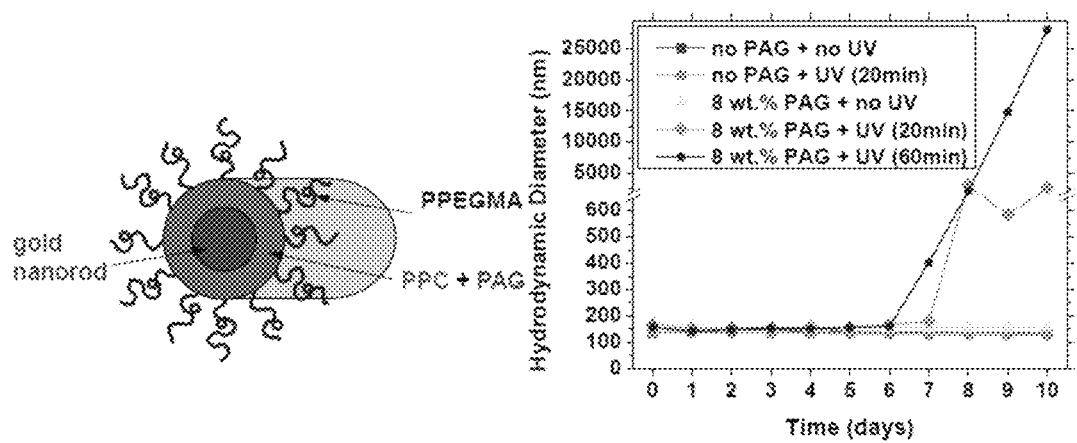
FIG. 84 depicts DLS Data for PAG-containing PPEGMA-PPC-PPEGMA BCP-encapsulated GNRs heated at 70° C. Under the influence of the UV-activated PAG 290, GNR-Encapsulating PPEGMA-PPC-PPEGMA micelles decompose at 70° C. (producing $CO_2$).

It was visually confirmed the generation of gas bubbles from the UV-exposed PPC/PAG 290 mixture in water. For this purpose, about one-gram amounts of the UV-exposed and UV-unexposed PPC/PAG 290 mixtures and the pure PPC material were placed in separate glass vials, and then about 7 ml of distilled water was added to each vial. The vials were then heated at 80° C., and photographed at various times as shown in FIG. 22. Notably, gas bubbles were continuously produced over the initial 4-hour period in the UV-exposed PPC/PAG 290 mixture; the bubbles caused a foaming of the polymer. No foaming was observed in the UV-unexposed PPC/PAG 290 mixture and in the pure PPC control. It is also notable that by the time 72 hours had elapsed, most of the mass in the UV-exposed PPC/PAG 290 sample was seen to have disappeared.

Example 5

Degradation of the PPEGMA-PPC-PPEGMA Micelles

In real ultrasound imaging applications, PPC would have to be formulated in the form of stable nanoparticles that are dispersed in aqueous media. Micelles formed by PPC-based amphiphilic block copolymers are the most appropriate method of achieving this PPC nanoparticle formulation. For this purpose, PPC-based amphiphilic block copolymers were synthesized. Specifically, these copolymers are "A-B-A"-type triblock copolymers, containing the PPC segment at the center block location ("B"), and water-soluble poly(poly (ethylene glycol) methyl ether methacrylate) (PPEGMA) as the outer ("A") block component (FIG. 16(C)); thus, this triblock copolymer will be hereafter denoted as "PPEGMA-PPC-PPEGMA". PPEGMA-PPC-PPEGMA samples were prepared by Reversible Addition-Fragmentation Chain-Transfer (RAFT) polymerization of PEGMA using dihydroxyl end-functional PPC (Mn=5.6 kg/mol) as the starting material, as schematically described in FIG. 16.

Figure 4:
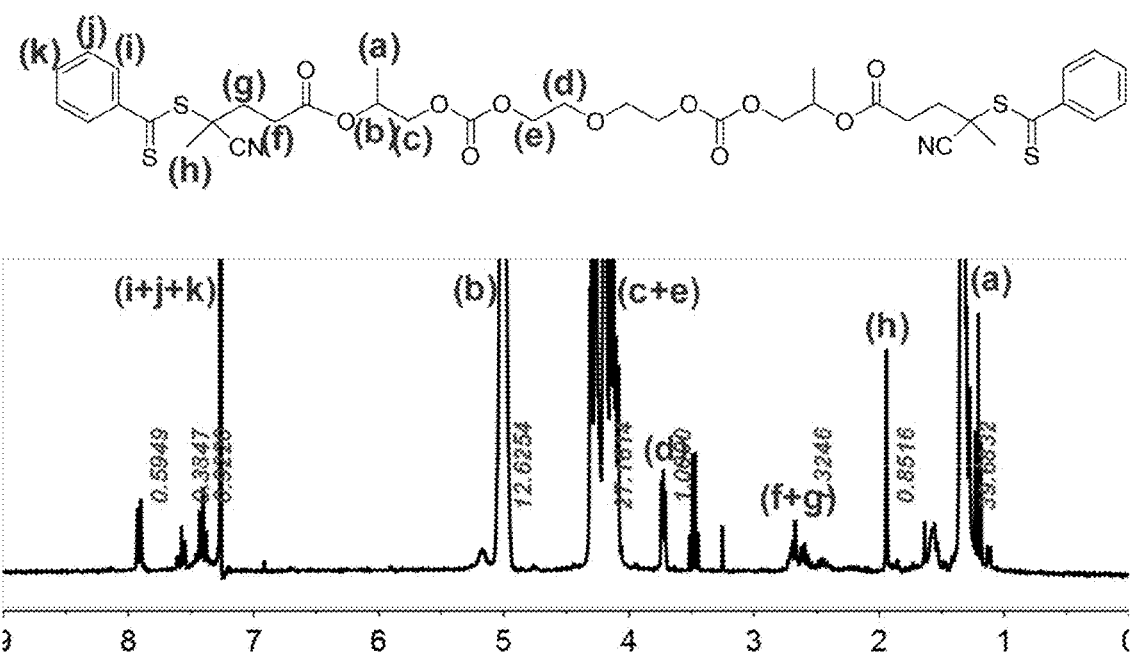
FIG. 4 depicts $^1$H NMR spectra of the CPCP-PPC-CPCP RAFT macroinitiator in $CDCl_3$.
Figure 5:
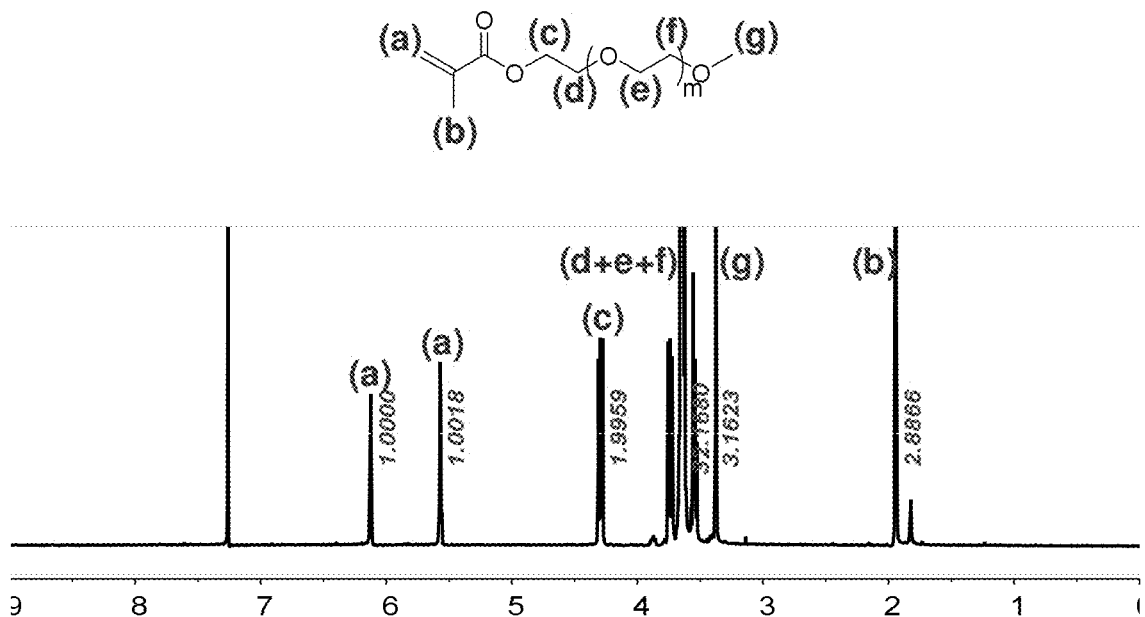
FIG. 5 depicts $^1$H NMR spectra of PEGMA in $CDCl_3$.
Figure 6:
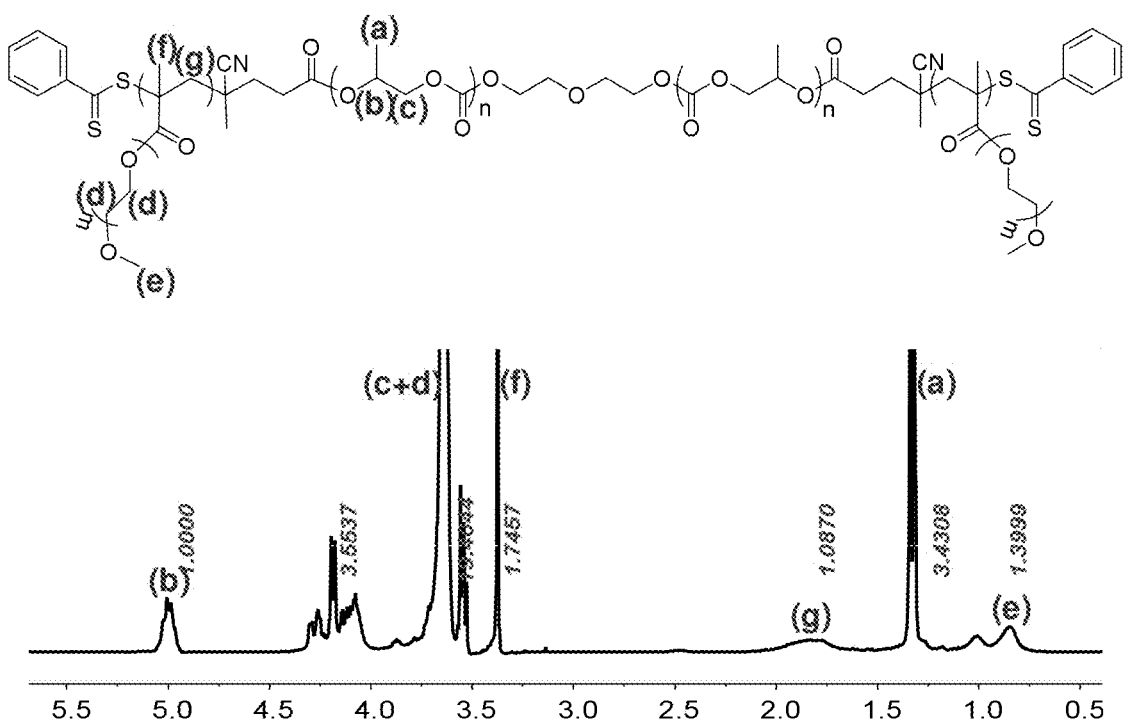
FIG. 6 depicts $^1$H NMR spectra of the PPEGMA-PPC-PPEGMA tri-block copolymer material (in CDCl3).

The OH ends of the dihydroxyl PPC were converted to dithioester ends via esterification with CPCP. The attachment of CPCP was confirmed by $^1$H NMR in $CDCl_3$ (FIG. 4); from the peak areas for CPCP (S=2.3-2.7 ppm) and PPC (S=3.7 ppm), the end conversion efficiency was estimated to be about 66%. The RAFT polymerization of the PEGMA monomer was performed in THF at 70° C. using AIBN as the radical generator. The GPC trace of the polymerization intermediate was seen to gradually shift to lower elution volumes with time, which supports the "living" nature of the RAFT process (data now shown). After 24 hours, the reaction was terminated by placing the reactor in an ice slush, and at that point the monomer conversion was about 98%. The final PPEGMA-PPC-PPEGMA product had a polydispersity of 1.31 (determined from the GPC data shown in FIG. 7). The $^1$H NMR spectra of the triblock polymer in CDCl$_3$ are presented in FIG. 6; from the areas under the PPC peak at S=5.1 ppm and the PPEGMA peak at S=3.4 ppm, the combined (number-average) molecular weight of the PPEGMA outer blocks was calculated as 15.0 kg/mol. This PPEGMA molecular weight value gives a weight fraction of PPEGMA of about 72%; this polymer is thus expected to form spherical micelles in water.

The PPEGMA-PPC-PPEGMA polymer was found to dissolve readily in water and form stable micelles with a diameter of about 150 nm (determined by DLS). When micellization was induced by solvent exchange in the presence of PAG 290 (initially co-dissolved in either GBL or DMF), PAG 290-containing polymer micelles were formed. The choice of the co-solvent (i.e., GBL vs. DMF) influenced micelle size; the micelles prepared using GBL had an average hydrodynamic diameter of 239 nm, whereas the use of DMF produced 102 nm-sized micelles; DLS data are shown in FIG. 24. This result is consistent with the previous observation that the higher the miscibility of the co-solvent with water, the smaller the resulting micelle size; DMF has a higher solubility in water than GBL.

Exposing the PAG 290-containing PPEGMA-PPC-PPEGMA micelles to UV light generally caused a slight decrease in the micelle size; the diameter of the micelles prepared using GBL decreased (from 239 nm) to 220 nm after UV exposure, whereas the diameter of the micelles prepared using DMF decreased (from 102 nm) to 87 nm after UV exposure. When these UV-activated micelles were heated at 80° C. for 20 hours, their sizes further decreased significantly; the diameter of the micelles prepared using GBL decreased to 172 nm, and the micelles prepared using DMF to 28 nm (FIG. 24), which clearly demonstrates the thermal degradation of the PPEGMA-PPC-PPEGMA micelles in water. As also shown in the figure, the UV-unexposed micelles underwent aggregation (i.e., their sizes increased to the order of tens of micrometers) when subjected to the same heating influence.

Example 6

Chemical Analysis of the Gas-Phase Degradation Products

GC/MS analysis of the gas-phase products of the PAG 290-catalyzed PPC degradation reaction was performed. For completeness, a set of four samples were prepared: the (i) UV-exposed and (ii) UV-unexposed PPC/PAG 290 mixtures (both prepared using GBL as the casting solvent), and (iii) GBL-cast and (iv) non-cast pure PPC controls. These samples were heated at 80° C. for 20 hours in a closed chamber filled with air at atmospheric pressure. After this heating, a fixed volume of gas was collected from each sample and injected into the GC/MS for analysis. As summarized in Table 1 (plots of the GC/MS data also presented in FIG. 15), the results confirm that under the influence of the UV-activated PAG 290, PPC indeed decomposes at 80° C. producing CO$_2$ as the main gas-phase reaction product. In the non-PAG 290 or non-UV-treated situations, the CO$_2$ generation was seen to be much less (i.e., by more than 30 folds) than what was observed with the UV-exposed PPC/PAG 290 mixture. The same tests were also repeated for hydrated samples. As can be seen from the results summarized in Table 1, the results were qualitatively identical to those obtained under dried degradation conditions.

Table 1 shows a summary of the results from the gas chromatography/mass spectroscopy (GC/MS) analysis of the gas-phase degradation products of the (1) UV-exposed and (2) UV-unexposed PPC/PAG 2290 mixture s (both pre pared using GBL as the casting sp lvrnt), and (3) GBL-cast and (4) non-cast pure PPC controls. The thermal degradation reactions were performed under either (A) dried or (El) hydrated conditions by heating the samples a$^c$ 80° C. for 20 hours in a closed chamber filled with air at atmospheric pressure. Concentration values represent relative abundances in arbitrary units.

TABLE 1

| Sample ID | CO2 |  |  |  |  |  |
|---|---|---|---|---|---|---|
| A-1 | 644744329 | 417677068.6 | 4469308.8 | 52235847.6 | 11957704 | 77337412 |
| A-2 | 20625961.5 | 127649655 | <1E+07 | <1E+07 | <1E+07 | <1E+07 |
| A-3 | 20579621.9 | 433945879.4 | <1E+07 | <1E+07 | <1E+07 | <1E+07 |
| A-4 | 12997100.2 | 1671571749 | <1E+07 | <1E+07 | <1E+07 | <1E+07 |
| B-1 | 683450991 | 135045451.8 | 24856342 | 210857425 | <1E+07 | <1E+07 |
| B-2 | 27091835.3 | 188812947.3 | <1E+07 | <1E+07 | <1E+07 | <1E+07 |
| B-3 | 32313687.3 | 176020502.7 | <1E+07 | <1E+07 | <1E+07 | <1E+07 |
| B-4 | 115244550 | 2166528260 | <1E+07 | <1E+07 | <1E+07 | <1E+07 |

| Sample ID | 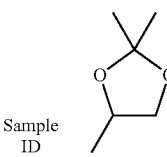 | 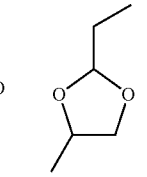 | 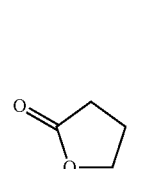 | 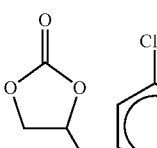 | |
|---|---|---|---|---|---|
| A-1 | 108410318 | 3094522513 | 72133859.7 | <1E+07 | <1E+07 |
| A-2 | <1E+07 | <1E+07 | 528415447 | <1E+07 | <1E+07 |
| A-3 | <1E+07 | <1E+07 | 140092154 | <1E+07 | <1E+07 |
| A-4 | <1E+07 | <1E+07 | 13964715.4 | <1E+07 | <1E+07 |
| B-1 | <1E+07 | <1E+07 | 106874101 | 80118421 | 9360820 |

TABLE 1-continued

| | | | | | |
|---|---|---|---|---|---|
| B-2 | <1E+07 | <1E+07 | 20158754.9 | <1E+07 | 5074222 |
| B-3 | <1E+07 | <1E+07 | 24914672.3 | <1E+07 | <1E+07 |
| B-4 | <1E+07 | <1E+07 | 528415447 | <1E+07 | <1E+07 |

What is claimed is:

1. A block copolymer comprising a poly(ethylene glycol) methyl ether methacrylate (PPEGMA) polymer segment A and a poly(propylene carbonate) (PPC) segment B.

2. The block copolymer of claim 1, wherein said block copolymer is a di-block copolymer in the form of A-B, a tri-block copolymer in the form of A-B-A, or a combination thereof.

3. The block copolymer of claim 1, wherein said block copolymer is a multi-block copolymer comprising at least segments A and B as component blocks.

* * * * *